US011583565B2

(12) United States Patent
Yoon et al.

(10) Patent No.: US 11,583,565 B2
(45) Date of Patent: Feb. 21, 2023

(54) **COMPOSITIONS AND METHODS FOR INHIBITING THE PROLIFERATION OF PATHOGENIC *ESCHERICHIA COLI***

(71) Applicant: iNtRON Biotechnology, Inc., Seongnam-si (KR)

(72) Inventors: Seong Jun Yoon, Seoul (KR); Jee Soo Son, Seoul (KR); In Hwang Kim, Gyeonggi-do (KR); Hyoung Rok Paik, Incheon (KR); Hyun Joo Im, Gyeonggi-do (KR); Ji Young Park, Gyeonggi-do (KR); Hyun Jin Yu, Incheon (KR); Ji Yeong Seo, Gyeonggi-do (KR); Soo Youn Jun, Seoul (KR); Sang Hyeon Kang, Seoul (KR)

(73) Assignee: iNtRON Biotechnology, Inc., Seongnam-si (KR)

( * ) Notice: Subject to any disclaimer, the term of this patent is extended or adjusted under 35 U.S.C. 154(b) by 284 days.

(21) Appl. No.: 16/840,334

(22) Filed: Apr. 4, 2020

(65) Prior Publication Data

US 2021/0308198 A1 Oct. 7, 2021

(51) Int. Cl.

*A61K 35/76* (2015.01)
*A61K 45/06* (2006.01)
*A61P 31/04* (2006.01)

(52) U.S. Cl.

CPC .............. *A61K 35/76* (2013.01); *A61K 45/06* (2013.01); *A61P 31/04* (2018.01); *C12N 2795/10121* (2013.01); *C12N 2795/10132* (2013.01)

(58) Field of Classification Search

CPC ................................ A61K 35/76; A61P 31/04
See application file for complete search history.

(56) References Cited

U.S. PATENT DOCUMENTS

2017/0035817 A1* 2/2017 Shin ........................ A61P 31/04

FOREIGN PATENT DOCUMENTS

WO WO-2019051603 A1 * 3/2019 ............. A23K 10/16

OTHER PUBLICATIONS

Jurczak-Kurek A. et al., "Biodiversity of bacteriophages: morphological and biological properties of a large group of phages isolated from urban sewage", Scientific Reports, vol. 6, article No. 34338, pp. 1-17. (Year: 2016).*

Wang, J. et al., "Therapeutic effectiveness of bacteriophages in the rescue of mice with extended spectrum β-lactamase-producing *Escherichia coli* bacteremia", International Journal of Molecular Medicine, vol. 17(2), pp. 347-355. (Year: 2006).*

* cited by examiner

*Primary Examiner* — Michelle F. Paguio Frising
*Assistant Examiner* — Grant C Currens
(74) *Attorney, Agent, or Firm* — SIMI Law Group, PC

(57) ABSTRACT

A composition for preventing or treating an infection or disease caused by a pathogenic *Escherichia coli* includes a Myoviridae bacteriophage having an ability to lyse the pathogenic *Escherichia coli* and a pharmaceutically acceptable carrier. A method for preventing or treating an infection or disease caused by a pathogenic *Escherichia coli* includes administering to a subject a Myoviridae bacteriophage and lysing the pathogenic *Escherichia coli* by the Myoviridae bacteriophage.

7 Claims, 4 Drawing Sheets

Specification includes a Sequence Listing.

50 nm

SEQUENCE LISTING

```
<160> NUMBER OF SEQ ID NOS: 1

<210> SEQ ID NO 1
```

<211> LENGTH: 152531
<212> TYPE: DNA
<213> ORGANISM: Myoviridae bacteriophage

<400> SEQUENCE: 1

```
agcacgttct cttaaacgta aataaaatca gaaaaatctt gatttgttgg tcgatttgtt     60
gtaagaattg tctgaataat aatcattctc atctatttta taggtagcct gttatgggcg    120
gcacctttac accgtagtaa tcatatgttt aggttgttaa gtgattgatt gataaaggat    180
tgtttgaaaa gtgatggtta agttaggccc gaccttacag cagggcaaaa catcgcctaa    240
gttattgaat acgaatgata atgataatta ttctcattga tatttgagga ttccggctcg    300
cagaagtgga ggggccgaaa aattcgcgtt cagcactcct gacgtatgcg ccataaatcc    360
ttgctaccaa aggcttttct tctcttgccg aagagatatt cttgccgata aatcgcagga    420
acaaggggag gttcaaagaa ccgtccccgt agatattttg ccgagtaata tttgaccaaa    480
gggggtgtca aaaataacag gtatatatag aataattgat agggaatacc aatgataaat    540
gaattgtaat tgccgaggat tgatcgtatg atgttcctcg ttgagagtta cgatgtttgt    600
catgaaacca agagaggaga ttatcatgca agagagtaaa aatgttccgt tgagtagtga    660
tacacttctg ctgttctata agaattggat ggctcaccgt aatgagttgg cgaacacagc    720
gaatggcttg tgcgtatgtt taggcaattt tgcatgggaa gtattgtatc cgaagcatgg    780
tgcagatgtg gatcagttct gggagatgcg tgaagcttta ggtgatgaaa tgatgataca    840
gtttatctat gcagggttgt ctaaaagcac acctttcaat actaacttct tcgaatacga    900
ggaagaatgt gaaaacagaa aatgtcatct caaccaacta cgtgtgcaat gggtgaaaga    960
ccggattcag gattgtgaag gaggtaaata tgaaaagtaa tattccgttg agcagtgcaa   1020
cattgcttcg cttctacaaa gcatggatgg caaaccatcc tgaaatggat cgcacgacga   1080
atggactgtg taattgtctg gaagcatatg tgggaagtta caatccttca actgaaagat   1140
ggcgtgccaa catgttgggc agtctgaaat atgaaatgag gaaacagttt gaatgtgcaa   1200
aactggacta caattttccg ttcaactgtg gttatgggga ttatgcatta gagtgtgacg   1260
ctaataagag tcatgaaaac ccacgccgta ttcagtgggt gcaagatcgc attgaagatg   1320
caaataatgc ttgcattgaa taaaaatgtc tgtatagtgg tttgcatacc gcgcataaca   1380
gatagccaat gaggagattg aaatgtcaaa tatgaaaact gtatccttgt atttagctaa   1440
cacggatcgt gtgcacaccc ttgctaatgc aagtcgtgta ctcgtgcagt tccgaaactt   1500
tgcaccgtcc gttgtgacag gtagtgaaac ctgcgttatc gatttcatta atgagtattt   1560
tcaaggtaat cccgcaggtc gccattttgt taagactcta aaggatgcgg agcaggaaca   1620
atgattcttc cagtagataa tgagatagct atgaatgttc tggatacaga atacttctat   1680
aatcactact ctgagacaga gtggatgaac acgcaaactc tgaaagagaa gacgcaatct   1740
ctgattaagt gtgatcgcta cttgcaacgt gcagaagaag ataatatcat gttagcatct   1800
cgtgcacgac gcgcttccat ctttaataaa atggtagcat tatggggagg tagaaaatga   1860
gcgaaaaacc agtgagagct tccacaatat tggaagcata cctgcaatgt gttgtagatt   1920
acgtcaagag aaactccagc ctactggacg tctaccgtgc agatgacggc gatgttggta   1980
ttgtttatgt gaaacacatt ttatccgaga cacgttatga ggtgttccgt gcaagtatgt   2040
tagggtgtga tcgtgttcgt gtgaactact tggacccgaa ttatcgccat gctcttgaag   2100
atattgaaga ttatcttcct cgctgcccga caggtaatgt aaaagtggca gaagaagcac   2160
cacaaggtgt tgattatcgt gtagccttgt ggaaaaaggc acgtcaacta caagtgctga   2220
```

-continued

```
atgagatgaa agaggagttg gagcaggaac tgctcaacga cttcgataaa tctccagaag   2280
aggctttagc gtggttgcgt gaagtagaac aataatttaa cataagagga gacactaatg   2340
tttaaaccag gtaatatata tcgtttcaga caaggcactt accaagagtt gtttcaatca   2400
ctctctaaac gattagctga agcgatcggg gagttttggt ttgaagtagt caaaacagac   2460
gcttacggga atgtcctgtc tcttatcatc ttcgtagaag ataagaagct gttctgggat   2520
cagggagtag gcgaggctca aatggatcgc ttccttattg gacacgatca gatcggatat   2580
ttctttgatg gaggcccgtt gttaatggta ggcttaccgc cgctggcacc gcagccaggc   2640
aaggaggttt ccgcgcacga cgatcgtcct gatgcggata ttgtgcctaa aaagtttgca   2700
gttattgttg actacgtggt agtgcatact gtatcatctt tttcagaggc acaagaaaga   2760
gccacgaaag cgaagaaaga gagtccaggg aagcttgtag agatttatac tctgcgtagc   2820
acagcgaaac tcgtaagtaa tgtgatattt gactaagagg agactattat gtttattcaa   2880
gggcattcct ataaattcaa aaatacaaaa gagtataatg cgttccgtga agctgtcaat   2940
ctgaaccgta agatttcaga tctgctgggt ccaaaacact tcctggtgtt ggagacaaca   3000
gaaaaagggg atgtggttaa gttccaaaca tttgaagggc atgtctttga agctaatgca   3060
ggtgctttcg ttgattgtgg tatgctgctg tccaaacatg agttaaagca ttttaacgat   3120
atcacttggt ttgactctta tgttgaggca gaggttggtt tgccaccaga accaaaggaa   3180
gagccagtac aagagccttc tcaagagagt ccagaagata aaaaatatct tgtaatggtg   3240
gatcttgttc ttgtgggcgt tgccggaaat atccgagatg cggaagatct ggcacaatcc   3300
tataaagaag ataacgctaa agccgtggtc gagatttaca atcgctacag cacggcacaa   3360
gttaaagttt attttgaata aatagcttga catagggatc acgttggtag ataatcgttg   3420
catacacaaa tgagaggaga aatgaaatga gcaaaacatt gaaagaattc taccgtgcgt   3480
atgcaacatg gcttgacttt ggcgcgccaa actttaaacc atttagccgc gcgtcaggtt   3540
tgtgcactaa cctttacaac tttagtaaaa atcatgatgt tatcaatgag atgaaatttc   3600
aattcgatgc cgctggactc gacccgaact atcctttcgg tggtgaagat gattacgtag   3660
accgtagtgt cgcacggcag caacatctta accctaagcg tatcaaatgg gtaaaagaac   3720
acactgaata atcaataaga ggagagataa aatgaatttg accgaacagt tgcgcagtat   3780
tgccaaagaa gcttccatcg gttttcctat tgaagaggtt attgagacgt gtttttcaga   3840
agcacgggcg ggaaactacc aacgggattt cacgccctct gattttggct tctgtaatcg   3900
tcctctttcc caggatggga tcgccagaca gcgcgagtta atgaatatgg tggtaacagc   3960
actccgtgag cgtggacttg tggtttatat tgaattagac agaaaccatc aagcttatca   4020
atgcatcact gttgattggt cggaggtgaa ataatgaagg gtaacaagat gaaagttaag   4080
aaagtgccga gcgcatacac tttgtggctt gcgcgagcgt taaaccagac gatcaaagat   4140
cctaagaagc caatgaagag cggaaagaag tttatgtcta aaggcaaaaa aacttttggc   4200
ttcactcgta tggctgttaa gatgaaaagg ctggggtata aaccaaacta tactcgttac   4260
ccttctgaat ataactggtt cgactaaaag gagaaagcaa tggcaggttt aaagttggag   4320
atgttgacaa agcaagaatt tgttcccgaa catggtgaaa cttacattgc tttcttgatc   4380
agtgattttt atgctgattt agaatacgtt gaactggaat gtgagttcca ttaccaaatg   4440
atcgacgcag aaactggcta ttgcctttct acttccgcag tgtataatgg ggataacggt   4500
attcctttta acacagcaat gcgttgggaa ggaaagaatc gcttcaagat cctcacagaa   4560
```

```
aaagaaaaag aggaatacaa gcaccacaag gaggaggatc aacgcttctg gtgggagaaa   4620

tcttggttcc tgtccgatcg ccgtaatctc cagatccatc cagaagaact ggatgaaatg   4680

tccatcggga ttatgaagaa gaaagacttc atgttccagg tgagagaagc taataagttc   4740

cgtgttgcaa ctaaagagga gaacaaaaca tgaaaacatc tattcgcgta aaacatgatc   4800

cgaacaccag ttacccatac gcgtatgttg aacgtcatca agggaactat tacaccataa   4860

cacgtaaagt accaactgat acagggttta actttgatgt tattgcactg gatgatcaag   4920

gtgttgataa tctggtgaac gcattaatcg cattgaagga agcatgatat gagaatccga   4980

ctaattgaaa atggggatac catcttcgaa acccgtaaag ggagagatcac agagattcca   5040

gaagaaagat caacaatcct tgtggatggt gttttgaaat attgctgtag tgtctacaaa   5100

tcttacgaga aggatcagta tggcgatcca gaaatctggt ttgtaggtga tgtgtattaa   5160

ggagagaaaa tgatcggaca tttctgtaag gtgaaagata tctccctctt tgagggagac   5220

gttgttaagt ttgattgttt caccttggtt tttgaaagat ttttaggtgg agacatggtg   5280

atcttcaagg tagaagggac tgttgacaat tacacagctt acgggctgca ttctgaagtt   5340

tattttcacg gttatgtgaa aagacctctt gtaactaaga tgtgggagga gtatcatata   5400

gacattacag acaaacgtgg tgttttctgg aacgttgaat aagaggagag aacaatggag   5460

agtaagaacg cattcgataa aggctacgca cagggttata aatttggcat gttttgccgc   5520

cacaatcctt acgatcccaa taaacatcct gaaaagtttc aagagtggga agaagggttt   5580

tctcaaggct atcaagataa ggggtggtta tgaaaacatt agaaggatat tacaaggcat   5640

acgcggattg gttagataag ggtgctccgc cttaccgacc tttctcccgt ggtgtagggt   5700

tatgtagcaa tcttcgatat tacactggcg ctgataatat cttgatactt actcgtttag   5760

agcgtcagct tgccgatcag ttcgaagatg cgggactctc tgctgcctat cctttcggag   5820

aagaagcttt tgatttatgt ttggaccaaa acaacatgca ccttgatcct aatcgtattg   5880

cttgggtaag aagccactta gaaaaaggag aaaaccaatg aaaacattag cttactatga   5940

aaacctacgt gatgcttaca tgagcctctc aaatccatcg gtcactgcac aacttttaat   6000

tgaaactctg gaagacctga tcgctcttta tcaggaacct acgaaggatt tgccattgtt   6060

tctcggcgtt cctgtagatt tgccgccagg ttggaggatt ctgatcgatg atattaaggt   6120

tatccggttg attgataact atgatctgat tcgtggggtc attcaccctt gtattcaggg   6180

cggttacaat ataaattggg ataaagaata tctggatcat cgtcaagacc aggcagaggc   6240

tatcaaattt ttgatggaga acattaaacg atgaaaacat tacgagagtt ctatcaagct   6300

tacgcagatt gggtggacgc gggagcgcca gacggcaatc ctttccgccg tgaatggggt   6360

ttatgcacta atctctactt cttcggttat tgtgatgatg atttgctgta tgaaatgtca   6420

aaacagtttg aagctgcggg gttggaccca gaactcccgt tcaataaaga ttgggatgat   6480

tacgcgagag agtataagga agatggttct catctcaatg ctgtccgtat ccaatgggta   6540

agggatcatc tcaaatgatt atagaaatta aactggagta cgccggagcg gtagctttag   6600

ttgcacaaat gcttgacgca aagatcaacg aagtgtatat taatgcttgg agtgtggaga   6660

tagacgtgtc tatggacaat aaagccaacc gtctattggt tgcggaatgt gaactaagag   6720

gtttacttta taaaggagaa ccctcatgaa gattaaagtt atcgatgtta caggctacgt   6780

aggttttgaa aatgttcaac ttccttttat tgttgaagcg cacctttca gcgatgatct   6840

gcaaacattc ttcgtttccc aagaagagat ggctaaagtg gaaggttgtg agatcctgga   6900

ggatgatgtt tgggaaggtt gtgactatgt attcttctct tgggatgtag aagtgatcga   6960
```

-continued

```
ggaataagaa atgtcttact ttacaagagt tgtttcgttg tgtaaaaagc aatatgagag   7020

tgattacggg cttttcgatg ttcctctgga cctaacagag tattgttcgt gtgggaataa   7080

gttgaaagaa gctttgattt acgcagaagg gagtgataat cttgttaaag tgaaagtgtg   7140

caggaagtgt cattcgattc ttcctgcttc tatgaataag tgagaatgta atatgataga   7200

aactattatt ttcgttgtcc tgattattat tttaggtttc ttaatgtatg aataggaggt   7260

ttaaatgagt aaagtgaagc actacggtgt aaaccccaac gacgcttggc ttatgtgttc   7320

ggatgatccg acagaaggga catatgtgaa gtatgaagat tatgaaaccc tgtcgaaggc   7380

agtgatcgca ctgttaacag atatccgctc ccgttatcca ggacaagatt tcacttgtcc   7440

acatattcag cttcttgccc ttctggtaga aggtgagaaa gaagtggaag atggcttcaa   7500

gcgtgtagag tatcaaggtg aaactttaga tgtgcctgaa tttgttaatt atattgcaac   7560

agattcaagt ggtgatcgtt atggttacag ccataagcca gagattcctg actggattac   7620

cgcttggcgt acttccgtta gtaccggaga ctattacttt cttggtgtgg gtagtagtaa   7680

agattggcgt ttctctttga cagaggttta atcagatgga agagatattg ccagcagcat   7740

atcgtttgaa tgatgaacgt atttgggagt ggaccgacgt ttcttgtttt taccccgaaa   7800

tagttcagta ctggcgagca aaagggtgtg ttgtagttat caatccttgt ggaccagtag   7860

atgaagattg cctctacttg gatggaaagt ggcatagcta ttgtcgctgg ccttttgagt   7920

ggatgcttaa cgaagatctc ccagagggtt gggagtatcc aaaagcaaag gagagaaaga   7980

atgtcttacg gaaataaaac ccgtttattc catgtagtac gtttcctgga tacaaagaaa   8040

gaataccttc tgcctttcat caccgaaccg gatcaagaag tgtttcgcct tactgaagat   8100

ggtgattttg ccactaccag tttggtaagt tatatgatta acgaagctat tgatgagggg   8160

cgagcaatct ctgtaggttt tgctacgctc tctttgtctg taatttctaa tgaggaggta   8220

gaatgagcaa ggtattcgct gtttactgta gtctctctaa gcattccttt gttaccactg   8280

gtaaaactta cgaggctgaa tgggaggcca aggaaggaga ggtattccga tttacttgtg   8340

acgatgggga ctatgcgtgg gatacattga aagatagtaa actggggcgt tggtctattg   8400

tgggagagaa agaagaacct ttcattcttg ttcctgctga cacttctgtg aactgggaag   8460

tgtctaaagc tgaacaagac caagctaccc ttctccgtag tctggaacat gccgttgaac   8520

aatggaaaga agcacagtgc aactacgata gctctcgtaa acacaaccgt gtgcttgaag   8580

cacgtataga attactggct cttagtttgc gtagccttat tctcgctatt gagcgaggac   8640

tttccaatcc tgatgggttc ccaatcagcg atgtagaaca cgaagtgtat ctggcacggg   8700

gtgcctatta tcatattaaa caagaatctg tagaaggaga gaaatgatgg aagaaaaact   8760

ggaacgtatc atcgatttag ccatgtctat cggctacgat gattgttttc tccagatcct   8820

tggagaatca gagaaagatt acgactcttg ggtgaaagag ttggaagaac tcaaaacttc   8880

cttgattgct gactttgctg aagcagagga taaagcagat cgttacaact atctgtgtcg   8940

gtaaagcttg acagacgctt actgtatggt atgcttacaa catcaaaaca acgaggagag   9000

aaaaatgact aaacttttat gtgtatcatc ttcggttccg tatttcactg ttggtaagca   9060

ataccctgtg acaaatacag acgaggatgt ggactactac tggatcaata ctgatgacgg   9120

aacagattgt gttattgagt tgagaatgcg ctgcgccact tttgaggtgg taactgaaaa   9180

cgtgatgcgt cttttcgaga tccgttatac aaaagataac ggcagtatta aaacttatca   9240

gatcccagcc ctttctatct acgacgcatg tgtacgttta ggtcagattt acggggacga   9300
```

-continued

```
taaatactac cgtgacgatg tgtccattca tgtggtagag gtggtgtaac atgaataaag    9360
atcggtttct ttctttagtc gcggaagcgc cttttgatgt tcttggggtg agattatgga    9420
aagacagaaa ctatgggtta gatgttcaaa catattctct ttggttggtt ggggagcaca    9480
gcttagatga aagcttgtgc atgggtatgg atactctttc cctctgttta aagtttagaa    9540
gcttagaacg cgcaaacaaa gagcaagaaa aactaacgag gtggctaaat gaaaacaagt    9600
gaagagttga tgaagtttta caaaaagtat cttgcctgga tcgaagatgg tgccccttac    9660
ggtagaccct ttctgccaaa ttgtggtttg tgtgccaact tgttcgatta tgtgcacaga    9720
gacaattaca accccattat aacaaccttg tcagatgaaa tgcacgcgca gttccactat    9780
aaagggttga gtcaagaact ccctttcaat gagaactatg atgcatatgt tttagagtca    9840
gatgcagatg cctgtcacct gaacgtggac aggattaatt gggtgaaaga tcgtattgca    9900
gaggagaatg aatagtggct gcttataatt ggtatgaact tgaagctgtt tgtcagtttt    9960
atgatggaat atttttgcgt gatccgattt gtcaagattt gagtcatcgt gcaagtgcat   10020
tagcaaaccg tgttaaaata aatggttggg acgcagatca ggaaaaagaa ttggaattcc   10080
ttttggaagc aacccgtatc ttccgtaaag tattccctca atggtttgag atggaggaat   10140
aagcatgtgg attgtccgtc ttaagtatga tggcaagttt ccgtgggaga aagatgtttg   10200
tgcctgtgat tcggcagcac atgccaaagc agcgggtcag gcagtagttg acatgtataa   10260
caacacttcc gttgatccag aaatggcagg tgttacaatg agcatgttca cttactattc   10320
ttttgaggtt tactatcatg aaggagagtg gaaatgagcg aagaactatt aacattttac   10380
cgcacgtatt tggcatggtt ggaagctggt gctcctgaag gtaaaccgtt cacccgttgc   10440
acaggtttgt gcacgaacct ctatgatttt tacgatatgg gggaaagcga acgatacgaa   10500
cctgtactgg atgaaatgca tgagcagttc taccacaaag atttggttat ggtgttgcct   10560
ttcaacagta attttggaaa gtacacctta gaagcggaaa aaagccgttg tcatttgaat   10620
gtggatcgtg tgaactgggt aaaagaacgt gtagcagaag aaataattgg ttgacagaag   10680
gatctgtctt tgtcataatc atctcatcga aacagagagg agaaaatcat gaaacagttt   10740
atctgcaccc gttccaccaa cagcgatatc cagaaaggca aggttatcaa aggggaactc   10800
ttccacgcaa atggtaagaa atacattttg ctgaaggact ctttcaacgg ggaacttcca   10860
cgtagcacct tcttcaacta caacacaacg tttgctttag agggagatgt ttgggactgg   10920
gctgaacttc atcctttctg tgaagaagag cagacagaag atcaggaagg gtttgtggga   10980
agtttacgtg ataaactacg tagtaaagca ctgcaagcaa attcccattt tactgaaatg   11040
gtagactgtg ttctgctgga gattgaagat tatgcagaac agggaaaatt ccaaaaatat   11100
tttgaacctt cgagttttgg tttgtgtaac agcccttctt cttacgaaga gatagataaa   11160
cagaaagaag gggtgaatgt agtagccaca atgttgcgtg caaaaggttt agatgtaaca   11220
ttgacaacag cggaatatag cgtttttggg gttatcaaac acatcatcat tagttggaac   11280
taagaggaga taaaaatgca aatcgaagag tctgaagaag aacttatgtt catgggtttg   11340
aatatgtatc gtgtagatta catcatgtgt ggtgtggaat actctatccg agtggggggg   11400
cttcgtccaa gtttcaggct cctttccgag cagggcttat cttagggact tgtcttgcaa   11460
acattgatga tgtgcagatc cagagagtag tgctggaagc agaaaacatt tgacagagag   11520
tgtcacacat attatagtga ttgcatcaac aacaagagga gagagaacat gcaagtagaa   11580
gaattagaag tgatcctgaa agcggctgtt gagaaaggtg caatcgctaa gtatgagcgt   11640
cagaaacaga agcacgacac gcatttcgct cgtgagtttt acatcacagg tgtagacggc   11700
```

```
acagaagtga cgctggaatg gtatgtaaac attatgacct tgcatatcgg tagtttcgag  11760
atgtgggtga agaatgtggg gatctctgat acccaccctg gcttccgcgt gagtctggat  11820
ttcacctctt acgaaggtga tcgctgtgcc cgtattggtc gtcgcaattc atttcaaggc  11880
taactggagg gtttatgaaa aaggcattac tgatcgcatt gtttctggtg actcctgctg  11940
ttatggcaga cactgtgccg aaagttaacg gcttctcgga ctcaaaagtt gtaaccaagg  12000
atcgctttgt ccaaactggc atgactgggg ctttagatta catcatcaca gacacaaaga  12060
cagggtgcca gtttgctatc gtctataatg gcggggtcat ctctttgggt tgcttttcgg  12120
agtttaagaa atgaaaaaca ttcgtgtgaa gtttcttgcc tctaagttta ttaatgtccg  12180
agactatttg accataggtc ggatctacaa tgccaaagta gcagatgaga actgtttcat  12240
tgtcgtggat gatgaaggat ctgaactcta ttgtttgttc gagaattgca gctatggcgt  12300
atggcaggtt atgtcggaag aagccgaaaa gaaagagagt ggaatgtgta tcccagaagg  12360
gtatgtcttg gtcccgaaag agcctacccc agaaatgttg gaggcagcga aggactggac  12420
ggggctaacc cgaacagccg aagttgtcta taagtcgatg atcgcggctt cgccgcttat  12480
ggagaaagga gatgacaaat gaaatcaagc attatgttgt tggaattcta tgagtggtgg  12540
ttggatcaag ctatgagtca aaatccaccc gaaaacatcc aagcttgtgg tttatgtcac  12600
gcagtagagg tgtattgtgg ggaagaccaa gatttgtatc ttaccctttt tgatgaaatg  12660
acagagcagt ttgaagcgga aggcttggaa tggaactatc ctttctatgg cgagtgggat  12720
ctttcaggtt ggattccttg ttattggatt gagaagaagt ctggcaccca gcacaagaac  12780
ttccaccgtc ttgcttgggt ctatgaccgt ctggaggagg tgcagcatgg cgaagaagaa  12840
taagatggga gttagtaagg gtggggaacc ccattatccc catccgtttg accccaagaa  12900
caaggcaacg attcatcgtc aatggattga gacacgtatg acaaagtgtc cgatcccagc  12960
agcggagcaa tataacaaaa agtatacagc ggagttcata gaatacactt tcatcaataa  13020
taaaggtaaa gaggtttacg ttgaagaaat ggttctgtgg atcaaatggg aggatgcatg  13080
agttttcaaa ctttctttaa gctgttattg atgttggtct ttttgggatt tctgatcctc  13140
cttgctgatg tggtatcaga cgtgcagaat gagcagatag cccttaaaga acaatgtatc  13200
gtttggaaac aggaaaaaga tgccaataaa ttccttgaca atagctgctt caagtttgta  13260
aaatggaatc ctgataacga ttgaggagtt gatcatgaaa aagtttgttg tttacagccg  13320
tttgtccaaa cagaagaaag gcgaagccca gtatggtatg cagagtcagg aaaacgatat  13380
ccgttacttc ttggagtctg tgccggaggc tgaagtgatc ggagagtttt ctgaatttta  13440
ttcaggtaaa ggtgactgga aacaacgtaa agaacttgtc aaggctgttg agatgtgtaa  13500
agctaccgga gcaaccctcc tggtagctaa agtggaccgt ttaggtcgta acaacgcctc  13560
agtagcaatc ctcttggaaa tgattgacgt taagatcgcc attatgccag atgcggataa  13620
gatggttatc cagcttttat ctgttcttgc tgaacaagaa gttcgcggta tggcagatcg  13680
tatcaaaaaa ggtttggcag tagctaagag caaaggtatt ctcttaggat ctgcatctcc  13740
aaaatataaa gagtctcgta aagattacaa acaatctcga aaaaatgata aaagcatctt  13800
gtatgcagag aagcttcgtg ataaagttac gttaatgagg aaagcaggag catctctgac  13860
tcgaattgca gagatcttta ctgaagagaa aattgaaact gttcgtggca gtaccacatg  13920
gcacccttat acggttcaac gtctgctcaa caaactgaac attaaatagg agctaaaatg  13980
acaaagaacg aagtgattat ccaacaattt cttaaggcat ggttagactg ggctaaagtg  14040
```

```
gctccgaaaa gagagaatgt caaacccttc agcacacttg ttgggctttg cgactctttg  14100
tcttactggt tactggaaca agggttttca ttaaaagaaa ttgacgaagt taccgaagca  14160
tttgcagaaa tgcttttcaa agatttccaa gacaccttgt acccatttgg tgacttagct  14220
tatatgcagg attatgagca cggtacgcaa catatgaaca aagaacggtt ggcatgggtt  14280
aaatcaaaac tgaaaggggg tagataacaa tgagcgcaat tttacaagaa ctctatttta  14340
acattgttgt tgctgtggcg gtatgtgtca taggaagcat ctatgcctta gaccgcactt  14400
ttaagaagcg taacaaacat caaaaactct cctacaatac ggtttttgtg tacaactaca  14460
ggccgaggga gggtaagagt ctgggtgtgg ggaatattga tgtacaattt acaaattggc  14520
ctcccactct ggatgatatt cgggaagtag agactcaaat taacgatact tatgattata  14580
acggtgtagt tatgatcaac atccttccag tatccaaaaa caaggagaaa gcatgacaga  14640
atatggagta atgagtgatt ttgaaatcaa caagcgtgtg tttgcagcag tacatggtgt  14700
caagccttta ggctatccgc acaatgcaga tggacgatca gtgggaaatg actgcaacgg  14760
caattacact tggtatgatt actgcaatga tccagcagat gcttgggcta tcatagtaaa  14820
acataggatt tgtatcagcc ctgtaacagg ggaagatggt tttcctcgcg gttggcttgc  14880
gaagacagaa ggtgtaccgt cccgtggaga cgataaaccc ctgcgtgcag ctatgattgt  14940
atttttaatg aaactcgatc gttcttaagg aggtaacatg gatgcatatt ctttacacgc  15000
tttggcagac tctgtgaact ttgagtatat ccaaagagca aaaaccttga tcacaacagc  15060
agccgaagag ggttactaca acatacagat tcaaaaccca gtgaaagctt taggtctacc  15120
gcaaggtaaa gaactacaag cttcgattgt acgcgggatt tgtgacaagt taagatctca  15180
aggttgcagt gctacgttct cgacagactg taatgatctt gtttactcta tgtatgtttc  15240
ttggtaagag gagggaaaat gaaagtagtt gaaggttatc cgttcggtaa gaactttgtg  15300
gcagtgtgga ctgtaggaga tgatttgttc tgtgcgtcct tccatttcca aaatgatcag  15360
tattatagtt acgatcagac tacagatcag tttattgaag agtgtgatca cggatatagc  15420
cctgcgacat tcagacgttt gaacgctaca ttctttgtga tcgattaatc attgacaccc  15480
tcttcggagg gtgttattgt ttgtgcatgt tgaacgagag gagcagacaa tgtttaaaaa  15540
gattctaaaa tggctttcca ctttaggtgg accacgtaat gacaccctta accgctctct  15600
aacaggagaa ccactaacaa tggtcacatt gggaggctgg ggttcaaaag gcttctctgt  15660
gaagcagaca gatgttggta tccaaggatc actggttagc tggaagattt cccaggttgg  15720
agataaccgt caaccttcca tagatctctt aaaaggggag tatgactatt gcttgacaaa  15780
aaactctaaa aatcatctta tagaagtgat ccgtgatcgc ttggaacgcg aaggtggcta  15840
ttacttcgaa acaaaaagaa atgcccacgg aacacttgac tttaagaagg tttattggga  15900
tactaagacc gttcagagaa ttgagaaact cctggaggaa tattatgatt cgaagctatc  15960
atagatggtt ggtcttgcaa gaagaaagag ttttacgtgg gatgttggga tacagcccaa  16020
acacagacga tcttctggat aaaatggaag agtattttaa agaaccccgc gcacacctga  16080
aagaagtctt aggtgcttgg gatggcacac cagaaagtgt aggagagtga gtatgaagat  16140
tgagtcaagt aaactgcttt tagattttta tcaggcttgg ttatcttggg ctgaaaatcg  16200
agatgagacg ggccttgtta tggaagacgt gtttagctct tctgtagggt tgtgtggtaa  16260
tcttgagtat tggttgtatg atttagacct tccagaagac aactggtatt taatcgaaga  16320
cactatgcaa gaaatgtata atcagtttat tgaagcaggg ctatgtgaaa catatccgtt  16380
cggaaggaag tcttatttac tggatgcgga aaatgcttca caacatacag acccagatcg  16440
```

tctgcactgg gttaagagtc gtcttaaaga tggaggaaga ctatgagcaa gaaacctttt 16500
actatccgtg aaaacctgga caagtccttt tctgttgtta atgagttcaa tgtctctgtt 16560
gccacgttcc cacagaaacg agatgcagaa aagctacgtg atcaattgaa tggtaacgga 16620
cgatgagaca taacgcagca gtcagacttc gatcaagtgg ttggacagta gacgaacata 16680
agacagggat gaatatctac aagatgatta acttcaagga ggagttattg cactgtacta 16740
agtttgcctt ctatcttatg ggagaagaat tgacgaagga tctggaagaa cagatcgaga 16800
ctgttgcaga aggatattac tcatgttcag tgttgattct tgtagacaag gatggtaaga 16860
ttgaagttaa acgagaagac aaactttaca gaggaggggt atgatgaaat ttgctacgta 16920
ttccctaata gcttttatta tttgggttgt tagtgttgta ggaggttggt tagcaggatc 16980
actggtagct ggacactgga ttacggtaga tgtgtttagt tggtggacta tcttcaggat 17040
actgttagca tcttggactg taatattagt ctggactgta ttcgaatgta ccttctctga 17100
gtaatagata gttagtaggt agatggttga tcatagtctg tctacctcac taacattgct 17160
tactccctat cgtgagtaac atgcaataat actatacaaa tcactactcg ctatcgctcg 17220
taaacatatg tttagggtag catgtttttt tgcaaaagtc aatacagcgt tccctatcaa 17280
ttattccttt cagataagtc ctacctatca atcaaaatca cccgttcttc gtagttgtaa 17340
tcgtaacgtt ccggtattat actctctgta actaacaaga ggaggtgtct atggatgcag 17400
taaacaggga tattctgttg atggttcttt tcgtgataac atctgccgca ttagctgtgg 17460
ttattgtgga caataacaag cttgttgttt atgtcagttt cttagtaagt gtggttgggt 17520
gtgttctatg tttctatctt gtagccataa gaggatacta agatttgtct gatggttgtt 17580
atccaggttt taatgtaaaa taataggatg agcggtgttt gtcgtacaag gaggaagctt 17640
tggtggaaat cttcttaccc aagaaaaact tgacagacac gcatcgtaaa tgatatagtg 17700
ggacgatttt aaaggtgact catgaaagtg gtcgaatatg aaacaggata tcgcataaaa 17760
acaggttggt ggatcttcgc ttggtgggtc acatttgcag ggacgggtat tcctgtctac 17820
ttcgaaacca gggaaagagc cgagggctgg ttacaggcga tgcaaagatg ggagaaacgt 17880
ggcaatgatt actaattatc tttataaagc aaaagatctt cgtgacggca attaccactg 17940
gtggttagtt ggagagcaag gtgttgctat cttcccgtgg aacggagaaa ctaaggctgg 18000
catgacaact aaactgaaag aggcgactaa tgtctttctt tatgatatta caaccttcca 18060
ggcttttgct gtcaaacctc aactgattgc cgaatggtga tggagataaa atgactaaac 18120
tttatgttgc aattgataag gtagatgggg tagaatctct attccttctt aatgatcatg 18180
gcgtattaac tatggaacgt ggtttccata ttgatgtgga agatgaagta cgtgcagcta 18240
aggtgctgga gcaaattaca cctccgtact tatactctcc cactgaacgt atgtcacaat 18300
tcgccttgaa tccccagctt ataggagaat gggaatgaga attgccagtg ttgtggatgt 18360
aaccataata acacctgtac cttgtacccc tatggagtgt ccatattgtg gaggtttagg 18420
atatgttctg gttgatgtag gccagcttta tgaatgcaat ccctgtaaaa ctacaggata 18480
tcttccaatg atagaggaga acgtatatga accaaaacga agagattgaa gaaactattg 18540
atgtgttaac tattttccgt cagatggaag gtgtagagaa caatgctcgt gttagcacca 18600
gcttgttgaa catttacaat accattgtaa tgggaaaccc ctcggacaaa gagttgcagt 18660
ttgatcttat gatgggaact ctgttggaaa tcaatcgtga aacgtttagc aaatacgaag 18720
agcaccaaca actaccagaa gatcaacgca atttcattct tagtggtgcg ttaagcgcac 18780

-continued

```
aagagacatt ttacaatacg ttagtggctg cttacaacga tgctttcgtt gtgcatatcg  18840
atgagcgtat tgcaatggtt cgtgatgtga ttgaagatca gatcgaagcg gctctggaag  18900
ctgtggctga acctttagct gctttacgtg ctggtacacc ggaggattta tgattacagt  18960
aggcgatgtt gtaaccttac gtggggaacc cgttatcatg actgttacag aggactacgg  19020
ggactcctgt aaagtgacat ggtttgatgc agagggtcat ctgttacatg ccacattctt  19080
caagaaagct ttggagaagg cggaatgaca acaccgcgag agttttattg tttcgtgaac  19140
ttggaaggca agaatctcgt cacggatgac gaaggttact tcagttattg ggagacagaa  19200
tttgaagcca ttcaaacagt acagaatatt ctgaaagagg cacccacatt tcctatgaaa  19260
gattttgggg tggcgaaggt gactgtcacg acaacagaat acacaaaaga gcgtaaaacg  19320
cttttccata atattgaagt tattcactac ttcacagatc ttatttagga gggaaaatgg  19380
aaacaactta ttgggacgga aaaacacctt tggatgttgg acacatagct ttggtctatg  19440
gtgcatcagc gtatgatcca gactacccat ccattgaaga gggtcaagaa gttacgatct  19500
tagcgaaaga ccgtcagcca agtcgagacg tgtttattgt gcgttggtat gatgagggcg  19560
ggtatattcg tgtgtcgccg ttagtgccac actgtcttca tcctgtatct aaaaacacaa  19620
aacgagcaca agattttgtg aacatgtttg actatctgca cagtatccgt cttaacccaa  19680
aagatgtgca gaaagtgttt gacaaactac aggaagtaga gcaagatgta tctcaagacg  19740
aggcgattga agtgaatctc tggggaaacg caggacttga tcttctcgtt ggaaaaacac  19800
cgttgactct taagctctgg tcttcagatt ataagatcga cgacgatcag ataggtatca  19860
atgttggagt gttggctgta gcaaccaata gcaaagttac gccgcaacag gcgcaatctt  19920
tctactggtt cgatatgcca gtgcaagctt cattttaaat aataggagaa aataatgatt  19980
gcatttatcg taggtttagt agtaggatat cacatccata agtatcaaga tgttatcatc  20040
gccaaagtaa aagatattct ggacgcatct aaataatcta tcaaaagctg catcttaata  20100
ggtgcagcct attaacctaa aggagaagaa catgaataaa gttaccaact tcaaatgtgt  20160
gcattgtggt aagtctttcg gtgatcatca ggctcgtact ttcaactgtc ctcgtaaagg  20220
acgtggtagc ttcaagggtt tcaacccttc acatgtctac tctccaaatt atgacaaacc  20280
agacgaagaa aaaatcgtac tttaaggagg taatatggaa ctcgtacaag aagtttacaa  20340
cggtcttaaa gctctcaacg aagaatggcc tgaacaagct gtgatcgcag ttcgagatgc  20400
agatggagaa attaagttct ccagcgttgg caaatacgat gttgttgaaa cattctctgg  20460
gatttatatg cgtggggatt actgcttgtt caataaaggt atggcacaag gcccaagcgc  20520
aaacttcttc ggcactaaag gtcgcccagc aatagtcaca cgatcagaat acgaggagtt  20580
tttctactct aaacgttgac aaacaattcg tgttgtagga tactaatcct accgcagcac  20640
atgaacccgc ttcggcgggt tttttcatat ctgaacaaag gagattacta tgttgagcaa  20700
aatcgaagaa ggttgtatgg cattcctggt ggacaatcct ttctggtatc ctgtgaagat  20760
tcacgtaggt gagagagtag gggaagatga gtgggagtgt atcttgagca gtgaaatgca  20820
tcattaccaa ccagcaatcc tgaagacaga tcaaatggct cgtattactg ccgaagacga  20880
attgattatc gagttgtacg agagagcact tcacaaatag ccgagaaccc ccttaaatcg  20940
cacagagacg ctctcaaaca gaaaaggcac ccacttgggt gcctttcttt tatgcttcgt  21000
tagattgcgt ttgaggagcc tcaaaatcct ctttagtaca ggttgcaagg taactgatag  21060
tttgtataac cacaacaact ggagtttcaa gcgtctcttc cagtccagag cgaactgttt  21120
ctcttgctaa atcaatattg gctttacgaa cacctgctcc agtgttggta gccaagtaga  21180
```

```
ggtttccttc ccctttctgc gtaccgttag agaagtagta gacgtaattg gcgagataaa  21240
aatcgaaagt ttcttgttgc ataataatct cctaataaga aaggggccgt agccccttgg  21300
ttggtttatt tgtttaagtg gtcttcgacc attttaatga aaccttcatt actgaaggct  21360
gttgcagctt tttctcggta aacaaaaact ccacgatctt catagagaag tgtttcttcg  21420
taattaaccc caggattaac tacgaccatc tttgttccta tgttgagggc tgggaacaac  21480
tcccagttga agttgatcac ttgattagag caacctacaa caatcaccat atcctgagat  21540
gtgagattat cgagcatatg gtacatctct gtgtacagcg gagcagattc cccgaagaag  21600
acaacgttag gtttcacgta atcgtactta tccacatcca cacttgcata accgatttct  21660
ttaataaact tccgatccac tacaatttct ggtaggtagc catgcacatg cagaacatct  21720
tcgtgaacaa caccagcacg ttccaaaaga tcgtctacgt tagtggtgat gtttaaaata  21780
cgatcagcgc catactctga gtataaacga gcaatcagac gatgtgcagc gtttggatct  21840
atattgtcca actctatacg acgcttgtta tagaaatcat gggtcttgtt gtagaggttg  21900
tatccttcct catcctcacc tccgataaca ggtaaatcgg gacatgtacg tctacgataa  21960
cctgcctgga atgccccaat attacaaacc tcctctaaat cgtactcgtc ccataaggct  22020
tttccactct ctgtttctgt acggaatgtt tgtacaccgc tatcggcgct tagaccagcg  22080
ccgctgatca ctattaatcg tcttggcatt cttcatcctc ctcgtaatca tcgtcatcaa  22140
aatcatacac ttcatcttca gaataactca cttcaaagta aatatcaaac tctgcaaaca  22200
aacgcaggat gttggacatg ctgtaatagt tatcataagc ttcctctgct tcatagtaga  22260
ggcgtagcaa acgttcagct tcttcgtctt ctgcccattt atgatcaaca taaacagaag  22320
cggcataaat attgtaggct tgttcccgac tatcaacaag atttcggctt aacagttcag  22380
ggaagtcttt acaatttaca ttcagtcttc cgcataacca caaagcaata tcatgccaat  22440
ctgcatcctc tccgctgaag cagcttgcga cttcgccaaa cttggcatct cctaagtctc  22500
cgctaatagt gatcatggtt gaactattgt aaccacaagt ttcgcaattt gaacaactgt  22560
tgtgcacatg aatttctact tgaaacatat ttcctcccat aaaagaaaag ccccctgaag  22620
caggaggctt tgttcagatg ctggcactat accagacttt gtaggtattt gtcaagggct  22680
tcttgatcgc cttggcaaac ataacaacga aagtctttaa cagatggtac ttcattctca  22740
tcccaatccc acattacatt acctttgtaa cgtgaaccag ggaagtcgaa aaatgctgta  22800
tgggtgatgt ggtgtggacc gccccaaacc tctgtaaagg tgaattgcgg atacgctacc  22860
ttcaccgcct ccgtaaacca agctttacga atcaaagcat cgttgataaa atgcgcgtga  22920
cgttccattt cttcccagtt cttccacaca cttttctcgt caagggaaaa tacaagatcc  22980
tcctcaatat acatgccatc ttcccattcg tcaaaatctg cctcaagatt atctacagac  23040
tcgtcaagtc taacaccatc atgagcagag tgtatccacc atcctgcctc cagtaaagct  23100
ttgacaggaa caaaaccttt ttctgcatac tggtcgaatt ctttggcgcg ggagacatga  23160
caatactcct cctcacaatc caacatgctt gcgcctttac gacgcacagc aaagaaatga  23220
ttaccaaaga caactacact gccttcccaa tcatcacgat ctacttgata cgccacaata  23280
ggttttccac caaaaggttt taaatgggtc atcattcctc cttatctaaa aggttgttag  23340
ataaaaacac agcacgagca aaaccgcgag cagttaacga tcggagttgc tttgttttcg  23400
cacttgctcc gcctaaactt ttccagcccc agaagcaacc aatatgttcc acaggcttct  23460
tcacaggttt aacaaaacca ttgccatgcc aaatacaggt tttctttgtg taaccgtcac  23520
```

```
gggtaggcat tttagggtgg aagctgcctt cttcatcaaa cagatatccg ccatactcgt  23580
aaggatcgaa atagaagtcc ggtttacgcc acaatgttga caatttgcca accggattct  23640
caatcatcca cggaacgttg tatttatttc ctaaagcttc cacgatacga atgttagcca  23700
aagcttcttc caattcttct gcgctacgtt cgtgcttact accgcaacca gcaagcatgg  23760
tacacggagg gaagccaaag ataatatctg gtttaggaat accgtaatct tcagggttga  23820
agttggaatc aatccatgcg ttcacgtaag tgatgttagg atgttccata cgcacgtcat  23880
aagccccgtg atcaccttcg tcagcattta cacaatagca tttatgccct gcttctgcgt  23940
aacgaagtac catgatccca gatccatcga atgttgataa aactacttta ctcattctcc  24000
ctccatttaa gacaaatatt gactttcttc caatcgctct cggttaagaa gatttgttcg  24060
gaattgatcc acaaatctaa atcttctacc tctggaaggc gataacgtag ctccaagagg  24120
tcgtgttctt cagtagaaat gtaccccaag tgttttgcca tgtcgtggaa ccaagcccaa  24180
ccatgcatat ttttaattac atgctctcgc tgcgtgagga ctttacgttt cagtccgaac  24240
caagaagtga ttaccacttt actctctcgg agccgtttgt caatagctgc tgtttctttt  24300
tcaatactta acagcttcac tcttgccttg ttgagatcca catgtgtcac tttgaagtaa  24360
ctttgtgact gatcacacca acccatatca ataacctcct tcgtaaggtt tcaccatgtg  24420
aagatttgct ttaaaacgtg ccacgtaatc atcttggccc atttgctcat acagttttac  24480
cacaacttgg aagttttccc aagcatattc acgaaaccat ccactggtga tcgaggtaca  24540
aactttggat aaagccatca taaaactttg tttaggagtt ggaccatcta catcttcccc  24600
aaacgggatc tgtgaacgct ctaatgccag gacacaagct tcttcgtaaa cacccagcaa  24660
acggatatgt ttaggttgtg caaagaactt ctctttactg gtcatcactt cgctatcgtc  24720
tttcatgtat gatttataag cgggatcacc caacacggca acagcttcat ggatggtatc  24780
gtgatcatac acataaggca cttcatcacc cttgaagaaa tctttacttt tcacgttcag  24840
attagggtgc ccgtaattat aggactcctt ctgacgcagt ttgtatgtat cttccaactc  24900
ttcagggatc ttcgctccaa ggttacgcat gaagtggata tccttcattg ttttcaggaa  24960
gtgaggactg tccttcttaa aacggtgact cattttcagg agatacaaaa catccaaagg  25020
tgcaaccaca ttgtaaccaa tatgtggcag atgatctgca ttctctttaa tgtattcgat  25080
caatgcttct gtagaatccc ctggttgagc aatatcgtat tccagatgag cacccgcgat  25140
cattttgata tgccctttgt tacctttacg ttcaacaatt tccacgaaac gatctttcga  25200
gaatttctgg gcttctgctt gccactcttc ttcagtgcag aggtaatcca gatctacgca  25260
agcacgatac agttctacac cacgagaacg acaaatcatt tccaacgcac gactaccgat  25320
taatactttc atatatcctc ctctcttagt tgatgagaca agtctaccag gttcttcgtg  25380
tcttgtcaac actcacacaa taaaaaaccc gccgaagcgg gttattattt attagcacat  25440
ttccgaggaa gacacccaaa gaccttgggt catcagaccg ttttcgtcaa tctcaacatc  25500
atagtctccg cagatatagg tgaggtaatg ttcttctgcg tttgttcctg tcgggtaata  25560
agtttcccca ttcccgtaat caccgatcca cgcttgttct tggaactgct cacaaagttc  25620
ttcaatctcg ttgcggaact tctgttgtga tgcttccatc tctttaactt ttgccttgat  25680
taaggcgata ccttctgaca tgatccctcc ttaacaatta ctgctgtacc aaacaccgtc  25740
agagtcaacg gtgaaaccat catcagcttc gccatagcaa gcagaagatt gccaatcttc  25800
aaaacagatt gcattgtttt ctaagctaag accgaaacct tccttttctg cttcttttgt  25860
aagttcatct accaaggaca tgatagcttt tgctttgtct gctaatgctt gtgcattacg  25920
```

```
atcactcatt ttatttctcc ttattaacaa ccgagggaag atgggtgcca gttggtccca  25980
gtgtattcgt tctcatcttc tgggtcataa gtaccaccca ttccatattc aacagagaag  26040
tgaaaacttg tgccagtttc atcagccaat tgttcagctt ctgcaatggc ttcgtgtgct  26100
gctttcagtg cttctgctac tgttttatac ttcgtcgtca taaaatttct cctctcccaa  26160
agctaatacg atattgaatg cacgataagt gaattcgttc agttctgtgt cagagtaaaa  26220
ctcaaactgc acaacaccgt cttgagaaga cataaacata ccgatctgca cagtgccttc  26280
tggaatgaga tgttgatatt ctggacgaag ggttacattg tagaaataaa gttcaccaac  26340
gcccatctca tcccatgctt cccaattgct tacgaagttg ctttcgtaac ttttcacttc  26400
attaaattcc gccattctct tcctcctcac gttttacttc ttcaattgta taacacatct  26460
cggtttcgag agtggtttgt ggtccacttg tgcgtatcca tccataaccc agtttaccag  26520
gtttgttaag atacttaata aaactcattt tgtggatagt cactataaca tgttttggat  26580
ttttgtcaag aacttttccg atatcttgca acaatttatt cgccagaatt tctgccatac  26640
gtgcaagctg cgtgtcttga agatccccta caccaataaa ataacggttg atctgttcaa  26700
tatctgcttg ggttaaatct ttatctacga agataatccc atcattcttt gaacgatcat  26760
cttctccgtc ataacgaaag attaccaaat ctctggcaaa acgcaaaccg tgatggacaa  26820
taccctgcat gatttttca atatctgctg taacatctgt gtcctcgttt atacgactaa  26880
ggttaaaacg attacctacg tttgcacgat ctaacttaat tgccactgat cgcccccttg  26940
accaacggtt taagaaaagc ataaagttct tcctttgttt taccacgtaa gttaaaacat  27000
ggaacgttat tagctttagc gatgagccac gccgtccgtg ttccgcccat aacatctccc  27060
ttcttatcct ctttggaaca tgccaataag aataaggaag gcacgggatg ctccagatct  27120
tgtcccaaca cctgatgaac gttacgttga tgcaatttac gtgcaccttg tttaagttta  27180
tcaaatgccg gatggatttc ctttatccac tggagactga tagcatagtt catactgtca  27240
ggattagcaa gcactatttt ctcacctggg atatcattac cttcaaactt ctcccaaggg  27300
atataaatct ccttgagagt tttgttttta gattcttcta caccagtttc gaaagcagag  27360
tcactaccgt ttgcattacc tgaacgtaaa gtaaaaccac agttagccaa ccactttgct  27420
acagcgacca ttaaatccca ttcttcgtgg gttatctctc gacttcccac acctgtgtaa  27480
aataggttgc tcataagcca cctcaacagg ttatttcaaa cgggtttctg ttagtcatga  27540
tccacggatc accagaagga tatggattat aaggacgaaa aacgtgtggt tctttgcccc  27600
acttcttcct ttcctcctca aaaatacgac gaaattctgc atattgatca tcgatcatca  27660
gattcggagc gtccgactca accttatcta catccttccc aattatgatt tcacgtacca  27720
gttccagatc ttccgtctcc agaataattt ctttacgaat ctcacctaca gattctacga  27780
ttgtaatttt atacattagt cctcctgtaa agttgaataa aactgaagtc ccccgtctgc  27840
atcaaaatag gcaaacgtta agttgttatt gaaaacagac ccagtatcca tataaacacg  27900
attagcattg atcaaaggtt cctttacata agaatgcccg tgaaacacat aatcaacacc  27960
cataacaacc ggaagtttca tgccttcttt agcacactct accatgtcac gatcccacat  28020
caaagcttca gcgaaaatag cttcttttgc tttgctcata cgcagatgtg gtatatctgt  28080
caagggaaga tattcaaaag aggaaggata tccaccatga ataaacccta acttcatacc  28140
tcgatagttc acaaccaaaa ccacagggtt gtcctcaacc atcgtagcga gcagagtaga  28200
tccttcttca tcgcattctg ccaacactgt atgaccaccg ttctgatacc aacactcata  28260
```

```
gtaacgacga tcaccttcca gtaaaccttt aatcatcata tcttcgtgat taccacagag  28320
agcatagcga ttctctttgc tacaaaactc tacaacacat ttgaagtttt gtttaccacg  28380
atctgtcaaa tctccgagag acacaaccac atctgtatct cggataccaa gataattctt  28440
acctttcaag taaagatcgt agcaaccatg caagtccccg ataatgaaga ggtcttgatc  28500
ctgctccacg gtaatctctt tatataaaat catatctcct cctcaaaatc cagaaaaata  28560
aaaatgttta ccttcccttc gagatcctcc tgtaatacga gttcggcaaa ctctgaataa  28620
gctttctctt caaccttctc aatatgtgaa gctgccagct tgaaaggcgt atctccgtct  28680
accttaacaa gcaaaaacag agaacgcatt tcaacgtctt gtttggtgcg aggaaggaaa  28740
tctacagctt caaccatgcg ccaccctaag tagccagggg tttgatgtat atctcccaaa  28800
tgcttctcta agattttacg cccttcgtcg ataagagcct gttctgtagt aatttccatc  28860
ccttcctcct caaatgatta acgctaaagc gtggctgaac ataggttcat tgatcacgtt  28920
cgctactgtt acgtatgtgt cttgcaccca gtaggattca acacgacata cccgaacacc  28980
atttatgtaa aagtctgaac aagatttata atcatcgcac aacttacagc tataagcaat  29040
acccaatgtg tcataaacat tccttacagc taaaaccata tcctctccac agtctttatc  29100
agaaaccatg aacatggtta agaccaagtt atttgcgaag gtgatactat cttcaatctc  29160
caccgattta caaggtagca atgagaaata actaccttcg gtaataattt tagcctccac  29220
ttggtttaga atactttgtg aaggtgctgt tacataaaac aagttctcgt ttggattctc  29280
aacgttgcta cgaacaacac aacgagaagg atttaatgga ttgaatacat ggtcaaaatc  29340
tacacattcc ggtaggtttg ccactttgaa agttttgctg atgattcctg ctgctgctaa  29400
aatgatacca gaattaatct tacctgtgta agtagaacgc ataactactc cttcgatcac  29460
tctatacgag agaagttctc ttctcctaaa tagataattg atctgtttac attataagag  29520
acattccagg aatccccttc atgcctaatg agaactcctt ccacatccaa aagcaaatca  29580
gaagcaaaat tgactgcctg tgtacgtgtc gggaactttt taacaactat ctcttcattc  29640
tcttgcatag cttcctcctt aaaataccct ccttgccgaa acaaggagag tacgaactac  29700
ttcaagcaat atcaggttgt ggtgatagtg tcttcttgga tcgtatcatc catctctgcg  29760
aacagatccg cagcagaata gttaccacct gtccaacgtg acaaaaggat cgcaccaatt  29820
tcttttgcat gtgtttctga ttctgcatag acattagtgc cagtatcgcc tttctttgct  29880
tcgtttgcgt aaacgcaata ataattataa gccattaatc atcccaatct tcaccgtttt  29940
gagcatcgac caaggcttta accatgctac cgtaatccac agtttgattt gcagaatgcg  30000
tcgctgtaac tgttatggca tctttaaaga ataccgccat agctgcttct gttgggttca  30060
aatcaccttc cagattatga gcaataccta agttaatgcc tccgtcctca tcatcaaaat  30120
caatagaaac ggtcatagta aatttagcca tagtgtgctc cttaaacgaa ataaaatggt  30180
tgagttagac ccaaaatttg ttttggatcg tatacgtacc aagcatacgc tgtcttatct  30240
gttccacccg ctacgaacga aggacgttcg gagagtacaa tcaaattcgt aggtgggttt  30300
tcttgatgaa acgctcgacg tttcttcgac tcaaggaatc ccaggcgaag caggtagact  30360
gacacgtctg cttctttcaa gctcttttcc aagaactcta atgccagctt gaatggaggg  30420
ttcgtgatta taatgtcggg acgattttcc catacgtgac taaaataatc cttaccttct  30480
tcaagctcac aatactgaga accttcagga aagtgacggt aaatagccgc tgcttgtcct  30540
ttacacggtt ctgcaaatgt aaatccttcc tctttcaaat tggtaaaatc aataacacta  30600
aacagcgatt caatcgcctt ctgcggagtc ggatagtaat cagactctgg acgatcatag  30660
```

```
cttaaagcca tttaaaagct cctccttagt tatagcctca tcttccacga acgaagagat  30720
ttcattaagc aattgcatct ctaagtttgt aataccaata gtgctcttat ctgttttacg  30780
agaaaggatg ccttcaataa cttcctcaat agacaagctc tggtcgtaga acttaagtaa  30840
ctggtaatcc acaggggaga ttttatcttt tatcagtaaa aactctaaaa cgtgttgcat  30900
gttatcgtca tattggagtt gatactcccc aaatgcatta acactataag aatccttacc  30960
aaaccacttt cttttctttt gaatcacgta ccgcgtttga atcaaagact gcaaacagtt  31020
tgaggcacgt ttacaagttt gttggtaagc attaacacag ctatcgacga atttaacagg  31080
aacgttcaac ataataatct cctctgtgta agaaatgccc ccgaaggggc agttttatta  31140
agcagcggga ttgtcgaaat ccgctacgtt tacgagatta atattttccg gtttagaagt  31200
caagtctttt tctacagcaa cctcttcttc taccgtctcg tcacctgcca cgtcacgagg  31260
agtttcttca ccagcaggat caccaaactt gagcaggttg atcagttctt gcttggtgaa  31320
gttttcgaga tcttcgtcag tcagttcaat gatctcatct aattcttcaa cgaaggtttc  31380
gccaccagag tatgcgtcac gcttcttggc aacttccata gcagcttctg gagaagcacc  31440
tccatccagt gctgcgagcg cgaaatcgga accactacct actgcgtagt attcttcgtc  31500
gattgggtat gcacgggtag gatcattacc ttcatgcaag aaaatacgtc catctggatg  31560
aacaacgaga gcaataaact cttcatcttc acgatcaggg ttagaactaa tcatcaaccc  31620
aggtactgct tcacgagccg cttcacattg cagattctgt tcgaaccact ggaagaaagc  31680
taaaacggaa gtcaaacgtc ctgcaccgcc tacaaggtaa tccccgatct tacggacttt  31740
cttgaaactg gttgagtcta cacgaccacc gaaagttact ttaccgtcgc taaggatctt  31800
gtttttggtt gcgataattg tagtcattct gcttcctcct ctgttaatgt tttaagaact  31860
gctttcccgc cgttgacata cttgcgcaga tagtctatcg cacgtaatgt ctctttgtca  31920
accagtattt cgtttgtgat cgccagtgga tgatttaaaa gatcactaca ctcacgaaca  31980
agcaatgctt tacgattgaa catattgctt aagaacagta acttcgcctc ttcttcatcc  32040
aaatggagaa gttcaggatt ggagccagct attcctatta tacattcata taagccttct  32100
tgactatcag aaagttcttg aaaatgggcc aataaccaat cttcaccttt acaccaagcc  32160
acaaacattg acaacttgtc tcggagggta aggttctcta aagttagtgc aatttctttc  32220
tcaatatgat ttacgcaaat ctgtcggaac tcattaggct tcacaagccc agtttggtaa  32280
cactcgtcaa taccagtccg atctataatt gtctgtacca tcgaccctcc ctttaagaaa  32340
gcatccttgc tttttgttat taataaattt ctgtgatgaa cttagacaaa cgagagcgtt  32400
tgttgtcatc tgtggttaac tgcacataac cgataaagtc taccagaggg acacgaacac  32460
catcttcacc ttcaggagca actttgtcaa gaagatcttt cagaccgttt gcacgctttt  32520
tgatagcgta ggtttgacga acatctccaa gaacaacaac atgagtgttg atccctgcac  32580
gctctaccag aagttttaat gtttctggag acataagctg tgcttcatca atgatcacaa  32640
tagtgttgtc cagggtagca cccagtaggt agttcgggat attaagttca atcttaccgg  32700
aaccaatatc attctctaat ttgtttgcag tcataaactg ctggaagatt cgtttggtgg  32760
attcgtagtg cgccgccagt ttatcagttt tatctcccga aaggaaacca atctgatcat  32820
caccaacttc agtcgggttt ttaataaaaa gaagcttacg gaaatctcct gctcgaagca  32880
tctgcaaagc tttccataaa gtcacggaag tcttgcctgt ccctgctgga gcatttacga  32940
ctgtaagatc attccagatc atactttgaa cgatttgctg ctgatctcct tctggtgaaa  33000
```

-continued

```
acccatctaa gcgatagtca tcatttccaa ctgcttttgc agcataacga ctttctactt  33060
tcgcattaga agctaacttc tggcgcggtg atttagcggt agctgttttt cccatagtag  33120
cactccttat agaaggggct tgcgcccctt tgttagttgt aagaatcaag agtcccagat  33180
gttagaacct tgattactcg ttctgcacgg tttggcgttt gagagtacca tttactggct  33240
ctcatgtttt taccagcttg agtatagtac gaattactga ttaaagtcaa gctattttta  33300
aagccttccg ttccggttaa ccccaactgg aacaccatat tgatgattgc cagtttacgg  33360
gtttcactca ccttatcata gattggagca agaatggaac tatttttaat ctgttttttc  33420
gccttttcaa catcgtcagc aaagatagca cgggcttctt tctctgtgat aactccgtta  33480
gtcttgcgac caacaagagc atccagaata cgaatagctt ccgctttatc tttcttttta  33540
gttaagaggt gtccaatgcc gactgtccaa tatcccaagg tgtctgggta aacagtcagc  33600
ttcagtcctt catcaacagc caacatgtca aactcatcta ctactttttt agccatgttt  33660
tcctttattc gtcgtcttct actccgtgat ccagttcgtc aaacaataaa tgttcaggag  33720
aagtctcacg tttcggtttc gtcttctttg tgttggactt aagctcgttt gctaaagcac  33780
gagaaaagat cttacgtttc tgtttacttt tcatttatat tactccgcaa tttgagccat  33840
gaaatcacgc agttcggtaa aaccgcctac gtgggttact gctccaagct cttccacaaa  33900
aatctgcggg aaggtgcgag gtgcaattcc tgttgctgcg atcactgctt gagtcatcac  33960
ttcaaaatca taatcctgat ctaatgtcag atattcaaac tctttttcac gcatagttaa  34020
gagttgtttg gacatttcac agaactggca atttggtttg ccgtaaatta caaaattcat  34080
gctctctcct tattaagtaa tactgctaaa gattcttcaa taccttgtcc gacgcttgaa  34140
ggttcattcc aaccagacgt aattagtata gactttgctg gtcgcatcgc cgccgcatta  34200
taggtttcag cagaggtcgg gtgtataata acagattcag gcatacgtgt caatatcatt  34260
tttgcgaact ggtgccacga aacagtgatg ttcccagcgt aatgcaaagt acgggtgtta  34320
tatcctgttt ccaacacttg gaaaatcatc ttagccaaat ctggggcata agttggtcga  34380
gatgtttgat ctgcaactac cgagaagtct ctttgaccat cgttgtaacg agataccata  34440
gtctttagga agttgttacc aaactcgcta tacacagaag ccgtgcggat aataaaagct  34500
ttatggtaga taccgcgaac agcagcttca cccaaacttt tagataaccc gtaaacattg  34560
atagggttgg gttcatcctg atggaacaac ggtttatcgc tgttgaacac ataatcagta  34620
gaaatatgga ccatatcaat atcccaagcc ttacagaagg ctgcaatatt agctgcccca  34680
tgtaagttta cagccatagc tgcatcaaca tctgtctcgg ctttgtccac agcagtgtat  34740
gccgcacagt tgataacacc gttaatattt ggggtgtcca tgatcgcttt tcttacagct  34800
tcgaaactgg tgatatctac acgcttttct ggatacacca aagtcacatt ctccggcacc  34860
actttacgca gtgcctgtcc caattgacca ttcccaccca atactaaata tgttttcatg  34920
atcccataag ctccttcagt gttttagctt gtgcatcctt ttccgaaatg ataggtacaa  34980
agttctcatc attgaaaatc atatcaaaac cccaatcaat attcacagta ggatcgttcc  35040
acaacaaact acgttcagat gccggatcgt agtagttggt gcacttgtat tcaaagttgg  35100
cttcataaga ggttacaaca aaaccatgtg caaagccagg cggaatccaa aactgtttat  35160
tgttacgccc actaagaatc acaccttccc attgtccgaa ggttggacta ccttcacgaa  35220
gatctacagc cacgtcaaaa acttcgcctc gtgtgcaacg tacaagctta ccttgcgggt  35280
tgtctacttg aaagtgcatt ccacgaagaa cacctaaagt agagaatgaa tggttatctt  35340
gaacaaacgt ttgtttgcca ataacctctt cgtaaatctt ctcgttaaac gtctccgtga  35400
```

```
agaaaccacg atcatctttg taaacttgag gtttaaagac aaccagacca ggaatactta  35460
attcttttat tttcatttac cctccgctaa ttttaataga tattgcccgt actctgtttt  35520
ctttaatgag ttgccatgat acaccaaagt ctctaaagaa atccaccctt ttttgaaagc  35580
aatctcttca aggcacgcaa tcttcaatcc ttgacagttc tcaatagtct gcacgaattg  35640
gccagcttcc atcagactgg cgtgtgttcc tgtgtcaagc caagtaaatc ctcgtccgag  35700
aacttccact tgtaacttcc tgtcttcgag gtagctgcga ttgatatctg tgatctccag  35760
ttctccacga tcggaaggag taacttccag tgcacgctca acaaccgaat tatcatagaa  35820
gtaaagacca gtgactgcat agtcagattt gggattttca ggcttctctt caatagatat  35880
agcttgacgg ttgctaccaa actctaccac accgaaacgt tcaggatctt taaccagata  35940
accaaagata catgccccac cccaaacatc caccatctcg ctggcttgga taaggagttt  36000
cccgaaactt tgtccgaaga acaagttatc ccctaaaata agggcaacag aatcttcccc  36060
aataaaatct ttaccaatga tgaaagcatc tgcaagacct cgtggttccg actgcatcgc  36120
gtaagtgatc tttatcccaa acatagatcc atctccaaga agatattcaa aatcttcctg  36180
atcgcctggg gttgtgatga ttaagatatc cttaatatct gccaacatca agactgataa  36240
aggataataa atcataggtt tgtcatacac agggagcaat tgcttgctca cactgcgtgt  36300
taccggatgg aggcgggttc cacttcctcc cgccaaaata atacctttca taaccctcct  36360
taaatctttt ctctccacca ttgagggttg tttaaatacc actctatcgt agagtaaagg  36420
tcttgttcaa atgtggagtt tgcactccaa cccagttcag attcaatctt agcagggttg  36480
atttcataat gcaagtcatg tcctttacga tcttcaacaa aagttattaa acttgaagag  36540
gggtaggttc cactttgcgg gtgtacggca tccatgtaat cacaaatcat atagatgatc  36600
tccatattgg ttttaggatt acgtgtacct acgttgtagg tttgtcctgg ttcaccgcca  36660
gaagctactt gaagaatagc tcgtgcatgg tcctcaacaa aaagccagtc tcgtacctga  36720
tcacctttac catacactgg gatttctttg ttcgtcaaga tgcttgtgat tacttttgga  36780
atcaattttt cagggtgttg gtaaggtcca aaattattgg agcaattggt aatgacgaca  36840
ggaagatcat aagttcggtg ccaagcttta acaagatggt cgcttgcggc tttagacgcg  36900
ctgtacgggc ttgaaggagc atatgctgtc tcttcggtaa agggagtacc agagtcagcc  36960
atatcgccgt acacttcgtc tgtggagacg tgtacaaaca tcttcagctt attccttggg  37020
agtagtctcg cagcttccag taaattgtat gtaccgatga tattggagtc gatgaaagct  37080
cgtggattct tgatagagtt gtccacatga ctctctgccg ctaagtgaat gatgaaatca  37140
gggttgcatt ctaccactaa acttttaact tgtgcttcat ctaccagatc tgtcatgctt  37200
agtttcgcat gagtaatatc tccgacattt tcaatatcgg ctgcgtagcc cattttatca  37260
ataacaaaaa cttcattttt aggatcttga caaagagagc gcactacggc gctcccaata  37320
aaaccaagac cacctgttac cagatagcgc attagttctc cttaccagac gttttgtgat  37380
actaaggttt cagtctcaat gttatactta ttaagcagtt caaaatagat ctcattcgct  37440
tttttattta aacttgtgag gtctatagca caagcatcac aaccgctaca cagcttaata  37500
ccgaagacac aatcttcagg atctgcgtca taccacggcg aaatgttttc cagacctaaa  37560
ccttcgtaaa gaaaccaagt aaaatcccca tcaaactgat cttgcacttg tggatcgttt  37620
tcaaaggttt ctttccattt gtcatacgat gcgccttgca ccatcttcca ctcgatatca  37680
atccccatct ttttctcctt cttcttggtt atcttcttca acaaccaaac cactaccaaa  37740
```

```
acaatgccaa cacgggctgt actgctccgc actaattaag gcattacctg taccaccaca  37800
aatagggcaa aaacgaaact cactcattat cttcctcctt tacgatttca aactttgcaa  37860
caccgttaac cacaatatga ccacaagaca taacaccaag ccaagtctct ccgtttttct  37920
taagacgttt accatgcaca tcacaaaaac cgttctttaa ctccgaggct tcataggaag  37980
cccctttgtc aaatacgtct ttgaatgtgt cgatcaatcc tacacattta agtttcatta  38040
gaagtcaaac tccatatcat cagaaacatc tttgttagcc gagttcagtt tataagctgt  38100
aacttggatc tcttgcgctg ctgcttgaat ctgatctggg tttaaccaaa tatccatcca  38160
aggtagtggg ttctgtttag gagatttaaa gctgtgcttc atcttcagac gacgataaat  38220
tggagccgca ttgaagtaca cccattgacg agatagttca gcattcagcc caacgataaa  38280
acgtccttcg ctaaacagat aatcacacca ctgctcttct tgagcaataa ctgtatccag  38340
aatagttgta agttcttcga tgttatcttc gtagatcttc ttccacgcag gatcttgcat  38400
cagagcatca atgacagcat agtccatttt aacatgcagg atttcatcca acatgatttt  38460
ctgaatcagt ttacaagcac caacgaataa ttgttgttct gccagagcaa acgttgccga  38520
gaaagaagag atgaactgaa taccttccag accaatcagt gctaccaggc ctttcagaac  38580
taacaaacga agcttatcat tagcttcaat cagacccagt gcatatttgt gacctgcttc  38640
ttccaactct cccatgatct ctgcaatgat acccatacgg ttgaagatct tgtcgttctc  38700
catgatctgc tcaataactt ctacagggtt tggagtacac tggcgaacaa tctccgaata  38760
agttagagcg tgaagcactt ccatctcact ctgcttcatc atcatagcac atgcttcatt  38820
gttgctcaaa aacggagaga acaaagtgat gatggatttt gccagagaat cattctccca  38880
ctggaacgac aagttcttga tcataacatc gtagttgttt tttgaacacg ctacaaagtc  38940
tttacgggtc tgactaagat ccacttcatt ctcatcccag tcttgggctt tctgaagttt  39000
atacagacgg tgcatttcag ggtaagtcac attaattgag tcaaagatcc ccaattgctc  39060
acccaggaat accggatatt tccccgtttt gtaagtctcg ttatgtaaat taattgctgc  39120
catttaaatc ctccactatt tcacaaaaac ctcttaagct taaaatatct tcttcctcaa  39180
aatcattgct ccggtagaaa gcttccagtg cttcccatac gcttctacca agtataacag  39240
tcactgtttc ttcacttctt gcccttgtta ttgcgtaagc tgtggcttct ggataaaaag  39300
attcccaaat ctgcatgtta gctatttcaa gacccccaag ataatggtga caccaagtag  39360
gggtaaaatc ttcagggcga atcaacagag gcttaaaccc aggtcggtag attggggtta  39420
ctccaggtaa aactataagt gtgctcataa tcctcctcaa taaaaagggg ccgaagcccc  39480
tatattgcta cattttacaa gcttcacaac caccgtcaga atcttcttgg gccatagatt  39540
ccgctgattt ggttcggctg ttcaggtagt aaagagattt accaccaagt tttgcaaatg  39600
tcaagataaa ctgcatctcg gctttcactg ataaacgtcc accttccatt ttggaataat  39660
ccaaccaagc atcacaggag ataccctgat ccgtaaactt agtgaagagt ccatacatct  39720
cggcaatatc tttagatggg gtgtcccacg ccgactgata gaacattttc agtttttcgt  39780
aatccggtac gataaacagt acgttacctt tctgactctg tttgtacatg atcgtgtcac  39840
gtacagggta gagtgagttg gtagtattac tcaccaagct acttgattcg ttcggggcca  39900
ctgctgcaag cacactgtta cggataccac cttgttcaat gataccagca cgtaagcctt  39960
cccaatccag cttcagttca aagtccccaa tagtatctac cgctttagcg taggtgtcaa  40020
tagggagcca accttgaggc cacttagttt tatccatcca ctcggcatta cctttctctt  40080
tcgccaagcg cagagaggct tgtgccaacc agaagtaatg acgttctgct aattcatgca  40140
```

```
tcaacttctt cgcataagta tcagaatagg ttacaaaatt gcttgccagg taatgtgcaa  40200
ggtttgtaat acctacgccg atagagcggc gagccttagc tgtgatttcg ttatgtttga  40260
acggatattc catcgtctca ataacgttat caatcgtcaa tacagtataa tacgcaacat  40320
cttcgtattg ctccggcgta actcgcccag caacaataga ggacaagaag cataaagcca  40380
attcttgatc ttctgtgttt tcaccagtaa agagatccgt cattttatgg aacgctttag  40440
taggtaaaaa gatctcctga cataagttcg actgatacac agtgtccaag aaaggagtgt  40500
gattgtttac gttatcagca aagaacatat aaatacgtcc agtttctgca cgttgaacaa  40560
tgatttcagt caacaggtca cgagccttaa caattttctt tttgatgcga cggcgactaa  40620
ctttatcgta gacagcatcg aactcttctt cacttttgta aagtgcttcg taaagttccg  40680
gtgcttcgtc acaactcaca agcatccact cttcaccttt agccgcacgg cgaaggaagg  40740
agcggtttac aacaacagag taatccagct tatcaacacg cttatcgatc ggagtggttg  40800
ggttcttcag tcgaatcaga tcttcaaaat ctggctccaa aattgtgaac gtaaccgttg  40860
cactaccacc acgactcgct tgtttagaag cccctacgct gtcttccatc cacttcagat  40920
aagggagaag accaccgtga acgatacggt tgttcttaac accttgtcca gttgcacggg  40980
tctggaggtt aacaccaatc cctgcattat ttaacgtgta ttcgtgtgcc agatagtttg  41040
caatagccaa agactctgct gtatcgtctg cacggaataa acaacaagac gcgctgcctt  41100
tgatcggagt acgtaacgtt gtcagatatg gagatggtaa gttaatctga agatcactta  41160
catatgtgta cagctttttg atatcgtcaa tacgacgatc tttaggctgg atctccataa  41220
cacgcattgc cacaccaata aacaggaatt gcggtgactc atgaacaata tcattcacag  41280
catcacgaac caggtattta tctgccatct gacgaagaac ggaataaccg taggttagat  41340
tcttgttgtg tttgacaatc ttaccaatct ctttgatttc ttcttcggta taatccatct  41400
tagcccaatg tccacgcttc accatatcct ggtagaaggt gtacagggaa gggatactgt  41460
ggtatccccc gtgagcctgt ttgtaaatca taccgagaag caatcgacct gccatgtcgc  41520
tatacgcttg agtctttttg tcaatacatg cagcgatcat agctttatgt aaatcacgag  41580
tagacacacc atcgtaacaa cgtttcacag cttctaattc aatttccgac cagttcagtt  41640
tccctgctgc aaattcagac catttacgca gtttttcagg attaaactct tctgtcttgc  41700
catttgattt agtaacgtat cgaatcactt ctcctcccta tcttaactat gaatcccaag  41760
cacgtctaca tcgtatccaa atttcatttc gttaaacagt ccgttcgcat aaaggaaccc  41820
ttcaaaatga tttatatcgt ggaaaccttt cgctttagct ttgcgatctg cttcttgtcg  41880
ttttggtgat aagcgtttgg aagtatctaa aatcactgta acattacagc ctactgtctc  41940
atcaaagtaa acttcaatct cacagccttc gtatttatta tcggtcatta tccctctctt  42000
aaagtgaatt gtcttctgct cttgcaggat cgtaggaatt accgaaatcg tccatttttg  42060
tgtgagtcac accccaaccg ccaaattctt catcaccata atgaaaaata tcattcttct  42120
ggtagatgtg tttgaaagga cagctttctt taacagcaaa agtataaaga gttgtgttga  42180
tataaaccag actgttgtcg ttgttactac ggatattaac attacgttca acagagaagt  42240
tgccatcttc gttcatacca aggaacacca gagcggcacg aagtacatct gcgtgacgat  42300
cgtggggaat atgaccacgg tatttttcgg actcttgttg ccagatcggg gtagacttaa  42360
cggtagacat gctcacggta gcccaagtgg tagtgtttac taatgacata attttctcct  42420
tttataagtg ggggatctca cctcccccaa cgttttgcta tactacacca aatctcatac  42480
```

-continued

```
taaagtcaat aagaatttac tcgaatcacc atttagtatg attatttaaa agctggcggt  42540
gctggataaa tcctttgaaa tttccagacc acaaacaaca tttacgatcc atgtgtgtaa  42600
taccttcttc ccaagtagta gggaatggag gcatattaac accagctttt tgttgtttta  42660
atcccgacaa atccatttct ttcattggag ttgcttgatg ttcaaacgga gaagcatgga  42720
ctttacgtcc agtcagcaaa cgcccgtaga tatccaaagc tttatctttg gttgcattca  42780
gacgacgata actcacttgt gcgcaacaag aagaagagat tgcaagtgcc tcttccagtg  42840
acagcatgac agtatcgcca ttttcatctg tagtgctata cccagcgaat accaaaacat  42900
catcccttc aagaccgatg ttctcgtaga cgtgatctac gtaaggggtg tgccattgcc  42960
ctggagccag tagttctgga gtagaggctt cataagcttc aaacataact ttagctaaag  43020
cttcaatagt cggatcagca tcagcatcgt cacgtaacca ccagaagttt tcatactcgg  43080
ttgctgtcag aacagtcttc attctctgga atggttcaag aaggcgatta caaacctgct  43140
tcgcgtaacc agcttccgcc atttgttctg caaagtttgc tgcactaagc gcagctaaat  43200
tccaccactc acgacccgaa taacctaccc caatgagagc atcatactct acaccctgat  43260
cctgcatacc aggttggtgt tgaccaaaac gaacaggtgc agcaggttcg ttgcgaacca  43320
tctcaatcaa agtcttgact ggaatagcac ggcttgaagc cgcgttgcgg gagaataagc  43380
ggtgcgtcat caactcagaa tggatgatac gtgggtattc cagttcgaaa gttgtaatca  43440
cttgcccttc tgcgttcata gactgggcga tgacttgtgc actgatatta gacattaatt  43500
tctcctcgtt cttttaacat tgaataaact tgccaacagg tttctgcttg attgtacaaa  43560
cctgtgacaa ctacgtttgg tttctttttt aattcttcca aatacgaatc tttatacatc  43620
gtattgtaat aaattttaat aacatgatct ggaaaataca acaggttttc tgccctgtca  43680
tctatggcaa tatcacaagg caacaggtat ttttcttttg tggcaaagaa accgttacca  43740
gaacctttac caaaatcaat ggttggcaaa gttcttagaa catgtttgtg ttttgagcta  43800
aggtgtccac ctttagtcac acttgcaata agtgcattat ctccctcttt cacaacacct  43860
tctaagaagt tagccatagg tttgatacat cccatcgtat catagagatg aggattatcc  43920
agaaagccgt aagggtcgat gttaaacttc tcacggaagc ttgggaagta tttagtaaga  43980
tcgtagtcaa cattcttgac agcttcgtag aagcctacac aattaccact aactttaacc  44040
aaccattcca accaagcaac atccagtgga gcaaccacca aatcccaatc acaaactatc  44100
ttcataaccc ctcctctctt ccagtattgt tatattaacc taactttcga tttcctgcaa  44160
taggattttg actatttgtt ctcttcgttt tgctacggta cttgctggtt cgatacctcg  44220
tttcgttaac cacttcttat cttgcttatc tttacagatc gcaatagctt ctttctcaac  44280
ttttgcctgt tcgaaagaaa taccctgctt atcagcgtaa gctaagatag agttacaaga  44340
tttacaaacc atacgtaagt cttccacatt gacataaatc agacgtagaa cgaacatagg  44400
aatgtcatca aaacattgca agttttttgc tgcatggata tgatccactt ggaagtcttt  44460
catacctccg gtgtatccgc acacttcaca agaacaatgc caaacctgtt tcggtaagcc  44520
agtcttctta tctaacatca ccttgccatc tttatccaga cgatccgctt tgaatcgttt  44580
tgcattcaac agtttgattt tgttagggtg tctcatccat gcttgacgaa gacagccacg  44640
aagataggtg taaaactctg cttgtgactt ccagggcgtt ccttcgcccc acattatttt  44700
tggttcttta cttgacaatt ggcaccttct tgattgtgta ttcaccaggt ggaatattgt  44760
gtttaaagaa caacaggcga tccaaacctg ccttgcacat attttctggg atagtgatag  44820
ttactaaaag cttatcccct ttacggttat aaattttata aacctcgcct tctccgtact  44880
```

```
gttttgtgtt attcgccatt actaatttgt tccttaagtt ttcggatagc gatcattgca  44940
tcttggtagt aagaacaata catgcacttc aaagcttcgc ggattaaggg atcttttgtg  45000
aagaagtcaa tcagcaacat agcttgatca gttttggcct tacttgtggc tgctgggtag  45060
ttttcctgta ccatgaaact atggttttcc atcatggtag cttccagcgc gatgcaatga  45120
atagctttat ccaagttgat catgcgatca cctttgacac gagtagagta tttagcaagc  45180
ttgcagaaac aaggtgtgcc acctacaaga taagccaact ctataggttg cattaccata  45240
tctgtgtaat ggtgtccgtc aacttgatca ttaaatgcat tagacataat tttcctcctg  45300
gattccgact ccaccttctt cagggtagtc tgtgtaataa gcaacgcgac cacggtacat  45360
aacattaccg ttatcatcaa gaagttcacc attctctaaa acggtgatct ccacatttag  45420
aagatcaggg tctttgtcaa tagaataact catccctaac atttcaaata attcaaaaat  45480
ttcattaccc gttaatgtaa tgctcattca acccccttag taattctgtt ctggagtggt  45540
gttatcccag attttaaagt tttcaagctc tacagaagca tcttcgctaa gagcagcgtt  45600
ataagatgca ttgtttcctt ttgtgcggat caagtttggt ttcttgtgta aagacaaatc  45660
gttagtgaac gccagtagaa ctctgcccgt agtcggggag atattaatca gaccaacata  45720
gtcactgtcg tactgacggc aatcaccttt atcgttcaca gacacaccgt acaggcaacc  45780
tccgataagt acctgttgac ggttatcttt ccctactgtc aaaccagagg aatcctggat  45840
tagttcgtta cggtccagat tatttaaacg taagaactga cgatacaaag cacgggctgc  45900
attgttacga ccagattctg cggcataatt acggaaatca gcagcgttac gaaaaacaat  45960
aatattctta ctcatgatag tctcctcttg tttaaggcgg tatgccttgt tgataaagat  46020
tgtatcgcaa tcagttctct gtgtcaacac ttaaatgaaa aaagggggccg aagccccttt  46080
cttattaaat cccgacaatg gtatttttca tcttatcttt ggaacggctg ttaacacgtc  46140
cacgagaaag tccaccacaa tcttcacaac gaataatatc aaaagaactt actgctgtgt  46200
ggtacttctt atctgccagt acattcacat gtgcactgcc acaacgagag caacgaactt  46260
tggtatcttc gtagtaagca gatacgttag gatgttgcgg aatccatgcc agaatcttaa  46320
tgtatagatc tcgcagagaa actacatcgc catcgttgta agtttgcata cgttcaaacg  46380
catcacgatc accttcacaa caagccttcc acaatgggaa cccttcgtta tcaagttttt  46440
cgctctctgt ttcgaagtaa gcacccatct ctttcagaga attagacggt aagaagaatt  46500
gtttcttagc tgctttcaga gtatcaacca caacatagtt cgacggagga accattccgt  46560
ggtatgcgaa acgctggtta atataagcac ggtcaaattt aacaccgttg tgggctacaa  46620
cgatatcagc ttcgtccaga agcttccaaa tgtcttgaca cagttcccaa tcgtctgtgt  46680
gatcaatatc gaacagaggg tagcttgcca agttcttacc ttcaacttca gcagtacgca  46740
ggtctgcgga agagtaggac agcaagtaac cacggcgaat cacctgatca ggagagataa  46800
aagctttgaa tcgacggaaa gtatacgcaa tttctggtgc tgtttcaacg tcaataattt  46860
taactactgg accttctggt ttaactttag gagttccagc attggcagag ttttcacgaa  46920
ccaagaaatc gttcactgta cttttctttg tcgcgctacc gagaactaat gcagcgatct  46980
ggcgagaaga aagaccttgt gttttaaggc taatgatttc tactttctgc tctgttgtta  47040
atttactcat taattgtctc ctgttgtgaa atgtacgctt gaagcatact ctcaaaagtt  47100
gtgttatcgt tatcccaacg cttcatgtaa acaagttgga atattgtctc gatccattga  47160
tcggttgtta attctactgc ttccccatcc caagatgtaa atttaacacc ttcagggaac  47220
```

caggtataaa atgtatcttt cactttctgg aaaagttcag cttgggtctt gcattcagat 47280
atcaagttga aacaagaaac atctccaaac ttaataccaa aatcctggta aggacggatg 47340
ctatctgttt tgtctcccat cagcatttga taggccaacc agaaagatcc ccaacccttc 47400
acctcttttt tcttaccctt ttcaacaatc cacaagtctc cgatggactc gtctatcaag 47460
atgatatctg tattcttgaa tacaccgtct tctttgtaga agttaaagag gatgcttgga 47520
gtggataggc tgtctttatc tattgacgcc aggatgtaag agaatttgcc tgtgcgtttg 47580
taatctttgt atccttggaa accgtacttc tctaattcgt catcggcttc gataaccgtc 47640
acaacatccc cgttgtgttg ttccaccaag tagtctttgg tgtcggatag ttgtaagggt 47700
ttaatgtcag atcgttcaga tttatattcg gtaggcatct taaaggcatg tcggaaggtc 47760
ttccctacac caataacccc acaatatttt tctaaattca agtgttttaa gatcgcttga 47820
acttttgtct tagctgcttg aaaagcatgt gacaaagtgt ctggtacgta ttgcacatca 47880
ataatttcaa actcttcttt ggtgaaaggg cgcttacctt gttcttcacg cttggcattt 47940
aatgccccaa gccaaccacc aatttcagtc ttactcttac cccaaaactc tgtcttattg 48000
tcaaattctt tttcggaacc ggaggctgca tgtttagcca gtatgcggcg tttctctaca 48060
gcagaagctg cttggaaagc aacctgatcg tagtcaataa ccacaacagt gtttaggtca 48120
acatacttgt gcaaatcttc cggttttatt aaaatgtacc cgctgataat tccccctatt 48180
attcatcgtc atcatccgta ctgaatgttt ttgtgtaagg acattgccga ctcgcagaga 48240
tctggataac tttgtcgtag atggagttgg aatagaaaca atatttagta ttgccgctaa 48300
cttcctcatc cgaaagaatg agagtagttt gtccagccgc tgccgagaaa cttgttgcca 48360
acagtaatgc tgcaattgtc tttttcataa cacctcctaa aagcctacct cgttgagtag 48420
gtaggcatag tatcacaatg aagtctgcaa gtcaagcact tatttaagaa tagttgcttt 48480
agtcagatct gccatcaaac cacgaatctc gttgaagcaa agtagagtag atgcttcaat 48540
agaaccttcg tcatcgttga agtatttagg gaaacgaagc ttactcaact tcaactcttt 48600
atctactaca aactccagca caccatcgta ctccaagcca atagcgacaa cctctttacc 48660
atcttcttta agttcgattg ctttggaatc gtaaagagat tctttcgtcc agacaacaac 48720
accttcacta tcttccagtt taatatagtt accaagagta aggcgatcag cttcgtgttc 48780
tttcagcaat gtaccaaaac ctttgataat tgcttcttcg tgaacactaa aacctacaga 48840
agggaaagtc cctaaaacat tacggaagaa ggaagtaata gcttccgcta ctttcttact 48900
acagttgatc acatagaaca ggttggttgt tttatccaga accacataat tgaagaaatc 48960
ttccggttcg gtttctggga gaagaccaaa ttcaatatca gctttcaggg ctttcatgtc 49020
ttctttagcg acaaagaatt cttgaccttg gctttccata tctactcgaa tttcttccag 49080
gcgttcattg agaagacgtt taactttctt cttgtcaact ttcttaacag attgaccaac 49140
ctggaggagt tccagatcgg agaactcttt tacgtatttc ccatcatctt caaaacgaac 49200
cagaccaata gtatgggctt gagatccttc agcaggtaca aagtcaatcg gaaattcgtt 49260
gaactcgttc agagacgcta cagaagcatt atcaccagca accatcggaa gtgcagattt 49320
aaaagattta acgaacatat atttcctcct attatttaac tctcacaata accgccccga 49380
agggcggctt acagattatt tcttagcaat gatttttgca atatcaggtt taacaaaggt 49440
agaaggcttc atgatcttac ctttgtcatc aaagaacaca taaactttct gtttttcatt 49500
gtacgtagca tgtacgccag tgtaagcacc ttcaggacga ttggcattac gctcttcaat 49560
cgctgtgcat tcttgtgaaa ttgcaagatc aatatccgaa gtattccata cagccagcag 49620

```
ttgcttctta gtagggtact tagaatcatt actgtcaaga acttctttaa taatcttttt  49680
gtctgcataa acagaacgca ccagcgtatc acgcgcaagg ttcataatac cagcactcaa  49740
tactgccatc tgaacaggat cagtgaaggt agcttccata ttgtcgaaat cggtatagat  49800
tgtttctgtg aagacagtac caacctgatt ttcaaggaac ttcagagttg cttcttcacc  49860
aaagaacatg tacaccaagt aactggaaac aacaaataca tcggcggctg catccaagag  49920
ttcaacgtga tcattagttt tagcggcttc ttcatactct ttcagttctt cacgaacaaa  49980
cccgatttgg gaaacaaaca tcgcttggtc aaattccggc tgttctccgc cacgcgcttt  50040
tgcattccaa tcgattacat gtttagctgc tttcttatag aagtccacat ctaccttaat  50100
ctctttaaaa aagttctcga tcatcttgtt ctccttatta aaaatagttt tttgcgagtt  50160
cagtcaagta gataacaacc gaacccattt gtgcacctgc tgcacagtat ataagcatcc  50220
gacttaattt tcgccaccaa gtgtttaatg ggaatgtaga agccataata ataccacaag  50280
ccacaataga aagcaacaaa agaatcagaa aaacttcaac acccataaat ccccccttaat  50340
taacccattc agccacaaag taaaaacaga aaatgtagat cactgctgcg tacccgatac  50400
ccgccattat cgcatctata gtttttgcta cagagactaa agttgtctta tctttgcaac  50460
agctaaggaa catacagcat acagccaata ctgacaacaa tatatacact gttaaaatca  50520
acatacaacc tcctttattc tgctggctcc caagtccctg ggatcatttt acgaagacgt  50580
acaccgactg gtttagttgg gataccttcg tcagaaaatt cttcatactc aatctcaaca  50640
aactgaccaa tcaaagtctc ggcattctct gctttacggt agttgatagt ttcgtgagca  50700
tcttttcgca tcaagaactc aacaagttta ccattctcca tctcacctgt caacactcca  50760
tcgttatttt tatcaggacg catagaaata actttaactt ccaaagtctg gcgcggtttt  50820
cgtttgatca cgtcatagga acgtttatca aactcataga caccatgagc attacgatac  50880
acgatacctt cagctttttc aagtaaagct ttagcataaa atgcatccaa ctgttcctga  50940
ttttcaatat actctgtatg tactacacag atcagttcat ccagaccact atcttcagct  51000
acagccttaa gagccgccaa tacttcaaca cgcttctcaa atggcatatc tgccacagga  51060
acatcgtaaa catagtagtt gaggagcggc gtattctcat tgtgcttttt ccatgcgctg  51120
ttgatctgtt gcaaactaag aacaccaaga ccagcgaaca cttccccatc cagaggatga  51180
ccaacaactt cgctgatgaa gtttggaata ccttgccagt gcggagggag tttgtaaact  51240
tctccagctt tagacaaaca ttcgcccttc atgttgatca ttgaacgtaa gccattcagt  51300
ttgtattgtg catacccagg gaagaccact ttatgtgcga aatctttata gtcctggcat  51360
ttcataggtg tggatgggac gtggttctcc gcctcttcca tagtcttata ataaccattc  51420
ttaagttgct tcgtccactt ggcaaaagct tcagcttcgg cttgttcttc tggagtggtt  51480
gcatttgcac gtccagtgtt tttagcttct gcctcatacg atttttgtgt aatcttccca  51540
ccaactttac cgtgagctac agtgactgtt gcaccgtccg taaagacggt ccattgtttg  51600
agtttaccat tggagtcttt accgtaaagt gtctgattag tctgtttcaa attccttcct  51660
ccttaataat atggtgtagt tcgaaaataa catcttccat aacaacgttt tgccagtctg  51720
tagactctgc gaaatactcg tctatatggt gaataccttc gctcttaaga tgatcgatta  51780
tcatccataa gaaatcttct gctggtgtac ctttttgaaa ggtaatggaa gtctttttct  51840
cactaccttc gaaatagaat gttgttgcca ttatatttcg tcccaagtaa ataatgcaat  51900
ttttaaccga ttgcagatct catccaaatc ttgatccaag attatggttg aagttgccaa  51960
```

```
catatgatca acactcgtaa agcgttgacc tttggcataa tccaacatgt cttcatacat  52020
ttcttcaaga tcgcaatcgt cgtcgaaaga agcaaggaaa tcttcatcct cgttacgtac  52080
ataaaatgca gtactcattc ttcttcatcc caagattcaa aagcacagca gtcatcggtt  52140
tctatagtac cagtacgtcc acaagaaagg caagtgattt tatcaccgta gaatacataa  52200
ttctcgtctc cgttggtatt cacggaaatc tgatcactgc cacagggaca ttccaaccaa  52260
ggcacaatga tatctttctt catgttttct ccttaacctt taggtgtgca gaatccacga  52320
tcaaatacat tcttacggat gccttctgct aaagccatct cacaagcccc ttgcgatccg  52380
aattcttgtg tataatcatt actaccatga ctccaaagag caaacaaaat atagattgtt  52440
gccatttttc ctccttaagc attcagttcg ttgttgagtt cgtaaatctc ttcctggaga  52500
gcatcaatct cttcttcaag acgaagattt tcttctttaa gctgtaggat ttcaaagttt  52560
ttctcttcaa tctcgttttc aaacttcacc ttattcaatt cattttcgta atgaagttcg  52620
gtgtagtcgt cacgcatctg ttcaacaaga tgaatcagag ataagatata gttatcccca  52680
gtttcatctc gccactcttc cccgtggcgc aagattgtga ttcgtccagt atcttcgtca  52740
agaatcgttt cgtacttacg accatctgtg taaatttgca ttgttcctcc tttggttaaa  52800
tgccttcgcc aacatttctg tttgaccaca gtttcaaagt ttcagcaaca atgtactctg  52860
tgatataggc taacgcttcg tgattttcgt aataaacctt aacacccaca tggtcaagaa  52920
tatcccacgc ggtgtgaatc gcttcgtgtg tcacgagttc tggtgtcggt tcggcaatgt  52980
ataacataca cggacctaca ctttcaattg ttgcaaatgc ctttgttacc gaaaaatttt  53040
tagttttacg gtgagggaag tcttccagat attcttccag actgaagtaa acccaaatgt  53100
ttgcatcaaa aacatcaatt ctaatttttt ccattagtgc tccctttatc ggataatttt  53160
gtgatgatca acagtgataa cttcacgttt ttccatcatc tcaataactt catcaaagtg  53220
caggatcttg ccatgtgcat cccaaccaac atcaagcatc ttaccgtagg cttcatcagg  53280
gaaagatccg tgagaatgtc cgtggagcat tatgctaccg cgaccctgtt tgttccagga  53340
ggcaataggg taatgactta agacgaagaa cagcttctgg tatttcactt cgtcataata  53400
caccacttcg ccatactctg caagcacttc tcggtgcttg ctgtaatcat ggttcccaac  53460
aagataagtg atatctcctt ggagacggga agcaatctta cgggtatctt cttcagtccc  53520
gaaacagaag tcgcccaaat gccacatctt aacaccaaga gtagtagcac atttgttcca  53580
tgcttcgatc agggcttctg tcatgtggtc catatcttcc cacggacgat attcaggagc  53640
aaactctcga atacgtttgt gcataaaatg caaatcgctt gtaataaaca ttagtataat  53700
ccctcgctaa atagttcatg gtcgtgacca ttacgctcat ggtcaatctg gtcagcattt  53760
tccgcgatga tgtaagcatc ctcacgactc caccaattgt aatactgatc gataaagcct  53820
tgattatctg gcgtgcacaa agttttgctg atcacacctg cttctttcaa cacgcttaac  53880
tgtgcatata gtacaggatt tgcatgtcga acgcaaggga taattaactc ttcaccatta  53940
ttcagaatat acttattcgc agcacagacg ataacacgtt gcgcataatg accctcacca  54000
atccaggtga gaggttggta acaaatgtta tgatcaagac tgctcattag gtttctcctt  54060
actcttcgtc tgtgtgtaca tcgtaaaagc aatcttcaaa agttgcaagt gctttttcta  54120
cgtcaggcca atggttagtg tgtttgtata cataaaaccc atccccttca tctacccaaa  54180
taacataaag cataacacct ccttaatagt tcacacgaat catttcaata ccatacctca  54240
acatagattc ctctgcaagc ataaacttct ctgccgctgc tgggttagaa gtatgtacaa  54300
aaataagagg attgccaaaa caaggcttac cgaaaaacag aagttcttcc aagcgcaaga  54360
```

```
aaacatcgta cccctcttga tcagagtctt ctcctaaatc attgtcaaaa tgccactcgt  54420
ctacagaacg ataacccttc tgcacctcat tcatgtaacg agaggcaaga agttcctgtg  54480
atgttttaaa ccagattgca tctggacaac cgtaatcttt cggatcacgt aaatcgtcaa  54540
gccaaataat agcacccata taacctcctc taagctggca tgattaaaaa ggaactctcc  54600
acttcgaaat gccaatcatc cacaagacct gattcccaat ccttctcttc gtggaaagag  54660
cagatccaac gatacatacc tggcggtgta ttgtcaacat cttccggcaa cccgtaatcc  54720
aaagctgtct taccgttctc tgtgaaacca gggtggagat taggagcttt cagtacagaa  54780
accatacctc caacatccac agcaacaacc cactctgtca tgtatgggct gtcatattga  54840
ggttcatcgt aacctacctc tacagcttcg tcacgcaaca cgataatagg actaccacca  54900
caaggcggaa caatcatata tccaatgtct acaccatcag actctgttac aatatctaca  54960
acatcaaact cgtctccgtt tttaatatcg tagcttttat tcaaagaaaa gaattgttgg  55020
ttatctacct ctgctttagt aatttttatt ttcatttcac tttaacctca aattcaacag  55080
gttgagcctc aatgtaaaaa cactgatact ctgctttatc accctcatca cgaggccatg  55140
ccaccagaga gttataacaa tcttctggtg ctttgaagac tgttttagtc tccacggtga  55200
cattcccatt gagggttgcc agtacaaccc atccagccac actgatcata gtgcctccac  55260
tttccaagtt ttaccattat caaccaaagt ctttgcaaca gcatactctg ttccgttaac  55320
aaggaagcag tataccacga aagactttcc aattgtaacc gtcttagtaa cctctacacg  55380
cttaacacct tgcatgtatt ttgccttgcc gaaatagagc agaatcattt tgcatccttc  55440
ttgttgttga taacatccag ggcagtgtat ggttgattcg tgccgagata ttccaggact  55500
aatggagaac cttcttgcac cacttcaaag ataccgtaga cagagctttc agcaaatacc  55560
atttgctccg caccttcgtc gtttacaaca agagaaaact tcttacctgt cccgttgagg  55620
atctcgtact tcttgcctac agtaaagagt ccagagtacc attcgttctc ttttgctttt  55680
acacacttca ggaaagtctt ggtcatttct ttttaccccc tttcttggat ttctcgtata  55740
agcctaacac agcagcttct tttgcacaag taggaactga agtcattcct cgtctttttg  55800
cgtctggcat ttgcaaggtc catactcccc accagtagag ttggtcttgg gtgagtggtt  55860
cagccattgg gtctgcctcc tgctcctcaa gacgctgcaa cgcttcttca attttctcga  55920
tagctgtgtc aaagacgaat gcctccgtat caaatttatc tttcttaggg actgatttag  55980
caaccttcag aacttcgttc ttcttgggtt tcttagtagc ggtttttgtt tttgatgact  56040
tcttcggtgt tgtcgccatt aactacctcc atacgatcta aaaaatcacc ctggaaacgc  56100
cagtagtgct gtcctgtacg taagtcttca tagatcacaa ttggatcgaa gactttagat  56160
actccagcag gttttggaaa ttccacaacc gaatacaaac cacctttacc tacgcacgag  56220
taggtcacac ctgtaattgg atatttactc atttcttcgt gtactccatc atcggcatgt  56280
ggtcgccagt gagcgtaaca cggctgtagg agacattttg tgtcttcaat gtctcaatcc  56340
attgcaagaa ctcttctttc gcttctgtgt agttctgcgt gcctttaact acatggatat  56400
catccagggt gacacggaaa atcatttgaa taacatcttt cattgctttt ctcctttgtt  56460
acgtttgtgg atttgattta tagtgttgca cacgttgcag acaatgttgt ctaaaacatt  56520
gattgccacc aggactataa tcaatgtcag gatagggtgc tccgttatcc aactaagcat  56580
tttttattac ctccaattgt ctttcaaggt taactctctt ggagaactga taatggcaca  56640
gcttgcaatc aatgtcaaca acctgatcat gatttaatcc gacaatctcg acttgcttac  56700
```

```
caccagacca atctacgtat tcgaagttct cgtaagacga acacttgctc aacaggaaag  56760
caagctgttc ccactccact gaaatatcat gtgcatgata ggaggaacaa aatacgtccc  56820
catcataaaa tgcatgaatt attgcaccat cttcaaagcc gctaacaatc cacttcgtaa  56880
acctcatcct accctcctaa atgcgtctct aacgcaatat ttaaatgaag atgataaatc  56940
accttacctc acaccttaat caatccacaa tgcgatctat gaagtcttcc atatcgctat  57000
acccataaca cagacggtcg aactcttttg gactatctac ttcacgacta ccgactatct  57060
gatcaaccca gtaagttttt gcatgtgtta catagtgacc tccaggttta ggtcgtggtg  57120
ttaggttgat accttctttc atacgttgct tggctgtctt agcaatactc attctattcc  57180
tcctctcttg tttaagttta ttcactataa cagatacacc aaagaacaca agcttttgca  57240
caatgaaaat aatttgaaaa ttgtcttgac tttgattatc gaaatgtgat accctaaaaa  57300
cctattaacg agcgcagcga gttaaggtct tgtttttatt ggttaagtat atgctcgatc  57360
taaaagactt aggttttaaa gatcttaaag acagttagat agtaacagat ctgctctata  57420
ctgatcaaca aactaactaa caaaaaagaa aataattatt attagttagt agttaaaaga  57480
attagttgac ttttagatct tacatatgtt agagttcatc ccaagaaaac gagaaccgag  57540
gaggttatat gagtaccagt gagaatccgt gcaagtggca ccacatccca atcaaagatt  57600
gtatgtcttg taatccgaag tcaatttaca acatttcatc ttacgatgaa gaagataact  57660
tgatggacag tgatgagggt tggggagatc ttgagtggac aggttacgaa acaaaacgtg  57720
ataagattat tcccagttga cttaacataa ccttcgtgct acactaaaag tgaggagatg  57780
ccgattactc cccattttgg ggttcgaagg atttatgcaa aacaattttt attttcgttg  57840
tcgggcttgt aacagacact tgactaacca ttccagacgt gataaaaatg gaattattca  57900
agagtcagat ctctgttcga tatgtacagg cttggcattt gacgacagcc ccgaaagggt  57960
ctatcagcat caaggtataa cagacgttct catttctaat gtaatggagg acgaacaaac  58020
aatcgattag gaggaatcaa tatgtcttta gtagaaaaac atgtgttgac tgatggtgaa  58080
ggtggagcaa tcttcatgtt caacccagag aagtatgtta ccgagagtga agacggtgtt  58140
aggatcgtca tcaacgagga cgttaaagtt atcgatttcc tggctcttat gcgtcaaatg  58200
gatctggaga actcttggca aaatgctgaa gcacttgtta tagcactact tgaaaaacgt  58260
ggctccgaag aggttcaaga ttacgcctaa aatatttaaa ataagtattg acaagcgtgt  58320
cttattttgt taagatacgc tttatcaagt gtggtaacag ggtcgttgac tgttgttaag  58380
acggatttgc atcggggaga tgttagaggc tacttgttca gaggttagct accaaagaac  58440
atacggaaaa gcttcggctc aagaacattt acgctgaatg ttgggcttac gtccgaggaa  58500
tggtagctac ttcctactac tttcaacgtc tctgttacca catttacggc cctgtagctc  58560
aatgggagag cagtcggctc ataaccgata ggcaactgga tcgaaaccag tcagggccac  58620
caacgtcttt atggtgtaat ggatagcaca ggagtcttct aaactcttag tcaaggttcg  58680
attccttgta aagacaccag aacattttag tatgaattag ctcaagtgat ttgaacccta  58740
ccactgatca tggttggcag agaatgaggc aaatatgcat gagcaagcta acggtgtaca  58800
acgtttgatt gcaagggtag attgctcgaa gagtaccgtt cgtggagaac gggggttggt  58860
ggagtcacca ttcataataa aatgttttaa aggtgttgac aatcaacatc gttctgtgtt  58920
agattaagtg tatggaaggg caaatcgatt ggcgacgaaa actgtcttga aaacagccga  58980
gcttgaaaga gccttgggag ttcgactctc cctccttccg ccagattagg tagattggtg  59040
aaatggtagc cacgacagtt tgctaaactg tggtcggaaa cggcgtgtag gttcgagtcc  59100
```

```
tacatctacc gccaagttgt ttttaatgta gcttgttgtt cttacttaag aagagtaaac  59160
tttcggcaga tggctctcac cgtcaccgat accacatagt cagtaccgcg aatactggct  59220
actttaaaaa caattttgtg agattggcag agtggtcgat tgcgggggac tgtaaatccc  59280
ttctgaaagg cgcggtggtt cgaatccatc atctcacacc aaatttaaac tggaggttgt  59340
aatgttattt gataattggt ttgatcttga gaaagtttgt attggaatta cattcacagg  59400
cggtgctcca gaatataaat acgctatgtt acaaactaac ggtttgtctg taagacttca  59460
aagtatttaa gaattatgga cttgtagagt taaggtaaac ccccagtcgc caagaggctt  59520
ctggaattgc aggtatcgaa tcctgccgag tcccagcatt gctcctatcg tataatggct  59580
attactgcgg ctttgtaacc cgcaaatcat cgttcgattc ggtgtgggag caccaacaca  59640
acattaagag cactgtgatt gatcgtcgta tcctgtgcac aaggtctgct cgaaagacag  59700
tgttcttagt attatgttga tcacaaaaag cgtcacctga aacttgaccg gagtagggtt  59760
ggatggggta aagaagaagc ggattctccc atcgacgtga gagttttcca gtgttgcaag  59820
cgacacccag gagattaatc acaaccgaac gcagggttag tcacccaacg ggatactcgt  59880
cactgtccca ccccaataaa actattgaca actgatagta aaatgtagta tagtaaagat  59940
gtagggcgtt cttggtgtag cggtagcatt ccgtccttcc aagtcggcgg cacgagttca  60000
atcctcgtag aacgctccaa attatttaat aaagggttgc cagaaaactt tctcttttac  60060
tcatggtttt ctccttctct cacacctctt ctggttgccc ttcattaaat ggtttgtagt  60120
gtagtccggt agcacacgac actttgactg tcgtaggttt ggttcaaatc cagacagacc  60180
agccatataa cggaatttag ctcagtttgg tagagcatac gctttgggag cgtagggtcg  60240
tagggtcgca ggttcgaatc ctgcaattcc gaccaattaa atgtttcgta gttcaatggt  60300
agaacccacg actgataatc gtgagataca agttcgattc ttgtcgaaac aaccagtttc  60360
ccgttagact tacaggataa gagatccaca actattgtga tgctggttcg aatccagcac  60420
gggacaccta atagcgggat agaggagttt ggtcgtcctc gccagtttca tatgctggag  60480
atcatcggtt cgaatccgat tcccgcctcc aaatatcgcg ccagcggtat ctttgaagac  60540
cttgcctggt tccttctaag agggaggggt gcgactccta aaacgcacaa cccactaaac  60600
actaaatact taataggaca catcatgtat acgttaaaaa caatccgtaa attttctaaa  60660
gaagatgaag taaagattta caataccgtc cccttcaatg taaatgaaga agaattcttt  60720
tactgcttag aggatgacgt aattattcag tatcattggg aaggttatga tcgaccagat  60780
ggcgtggtgg cctctgttat cgcaggtgaa cgtgttatct ttgttcacaa aactgaatca  60840
gcctatctga tgaacgacaa aggacaaact gttaaggtaa tcaaccgacc ttaattgaga  60900
gttatcctaa agacattttt ataccaaaat gttaaaatgg cattagggac acatgttaat  60960
ttacacccta acattcatag agcctccctc gtggaggctt ttttattttg gagataccca  61020
tgaaaataat tgcccctggt ataggaacga atgcatggac taacattttc gacatagttc  61080
aagtagatcc taaatatgca catattatag agaacgtatc ctctgtcggt atacgtttag  61140
ctttaaacaa tgaaacactc tctgaagtta aaaactgcat cttattacaa cctaatgaag  61200
attttttcat ccagcccaac tggggcgttg cctctgtaat agcagagggt acagcaccag  61260
gtaagatttc gatacgtagg gcagaaagca ctgatataaa agctgcgatg cgtaaaattg  61320
taggtttgtc agatccaaga gtccttacac aaacattgac acaaatagaa gctgcaagta  61380
tagaaggtag actttttcaa cttacggtag atgttatttt accagcagga gtgacacagt  61440
```

```
ggtttgagtt tatagctcct acagataaag agtgtgcttt tacagattgg aattttgctc  61500
ctttctatac aggttttgag gctaaaatta tcacaggttc tacgggaggt gtagtcggta  61560
cttcttacac taacaggaac gttaacttaa aatatggaac aaattccact gcgcaattcc  61620
gatccttaac tggaaaccct acggtgggta ctgtgtactt catacctgca tttatcccag  61680
cctctggtgc aaatccgaac aacagggcaa caggggttag ttcagtatct tctggttaca  61740
ggataatacc agcaggagga tcttttagga tggaactgat aaatacatct ggaaatgcaa  61800
acagggtggt tatctccctt acttggttag aagcccctac ttctgtactg tcttaattat  61860
aaaccttgac actatccttt ttatatgata ggataaaatg taggaggact gtatatgcct  61920
aaactcaaac gtggtcgtgg acgacctaca gcagaaatgc aacaaattta tgctatggat  61980
gcagcacaag caacagtgaa ggaattgttt gccgagaact atctcgcagc aatgaaatac  62040
atcgttgaac ttgtgtatga taacgaagca gcaaaacctc tccgattcca agcagcgaaa  62100
gccattaaag agcaagtaga agactggttg gaagaacatt atgaagcaat ggaagaagaa  62160
actcctgccg ttgtggaaga acagcctaag aaaattgtaa tttaacctct cctctcttgg  62220
ggcactttgc cctctcctcc ttgttatttt aacaacccct ttccgaaagg ttaggggctt  62280
ttttcttttt agggcttgca ttgtgtatat gttttgtgat aagatcaata ttgaggagga  62340
taaaatatgc gcaactttgt agttaagaat gattttaaca aagcttctgt ccatcgtgac  62400
aggaaaaatg attactcccg tcaatgggat cttgaggacg aattagatga tgatcgagaa  62460
gacgtgggaa gagattcttg cggaagccaa accgatggaa gtgaagaagg tagtgaataa  62520
ctctccatcc ttacctaaag tgagatttaa agatgacact gataacaatg attctgaaga  62580
gtaagtggtt ttacgttatt cttctgttag ttgcactttt agctggtttg tacttcggcg  62640
gaaaggctct gtatgataat ggttacgcag caggagaaca aaaccaagta actatctatc  62700
agcaacaaca agcaaaagct aaacaagact tcgatgttct tcaaaagaaa gccgatgatg  62760
aacgtctggc acttaacaac caaatagctt ccctctccga aaagaatgct aaattgaaaa  62820
aagatttagc aaacaaggag aagaaggtga atgaggagaa aacaaattat gcaaaaacta  62880
ctactgggtc tatgtcttgc ttcggcccta atgatgacgg gttgcacatc ctcaacaaaa  62940
gcctccccga ttctaattga cgaatgcaaa gctgtagcag tgcaggaagt tagaggacca  63000
gactcttctt taatggaagg tgtaagtgaa cctgtaccgt acacagacca acaaattgct  63060
aaaggtgttt ctcgttctga agtagttgat aacgggacca caaacaatgt tctctggagt  63120
caagatcgta ataaagtaat cggtctgcaa aactacatta aggctctgca agagaaaggg  63180
attatcagta agtaaggagg agaagtggct aagaaaaaag cggctggcag tttagctggc  63240
gctgatatcg aagtaaaagc tcaaccaggt aaacagacgc tggcaatgga tctaatgcca  63300
gaagttatga tttacggtgg tgccgcaggt tgtgtatctg ctgaaacaga gtatcttacc  63360
cgtgacggct ggaaacaaat aagccaatac agcggagaag atatctatca gtataatcct  63420
aagagaaaac gcttagaatt ggtcacgcct tacttcgtag aatatgatat gaaagatgat  63480
aacttgtacc gaatcactaa cggtgcagga gtgttccaag aattgagtat ggaacatcgt  63540
ttcgtctttt acaagaaaaa gaaatccaaa aaacattttg agattgctgt gggagatctt  63600
attgctctgc aacaagcagg ggcaccactg aaaggataca ttgaagatcc gttcggtaag  63660
cgcgttccat ttaacatccc aggcaaacaa aacacttatt taaaaataca cgaggttatt  63720
acatccgatg ataaaaaata ttgctttgaa actccaagta gctatattgt ccttagacgg  63780
ggcaatcact gcttcgttac tggcaatagc ggcaagtctc gtctgctact gctaaaagct  63840
```

```
cttaagtttg cctataaaga tcctttgttc ggtggtatct tattccgtaa gaacaccact  63900
gcacaccgta agccaggtgg tttgtttaca gaagctaaac gtctgtacct gcctttacaa  63960
ccgcacgtaa aagaaagtac gatggacatt atctttgagg ccactaacgg tggtactttg  64020
aagtttgacc atctggagaa cgataacgtt acagccgaga ctaaccatca gggtacacag  64080
tacagtatgg ttggttttga cgaactcacc catttcaccc agtacgagat gctttatctt  64140
ctcggtcgta tgcgttccga gtcagaaaca tctttcatgc tttgtacctg taaccccgat  64200
gcggatagct gggtactgaa ctgggtgtta ccttatcttg acgaaggtgg ttatcctcgt  64260
gaagatatgt gtggtaaaca aacctacttc attattgtaa atgatgaacc tgtatttgcc  64320
gacacagcag aggaacttaa agagaagtat cctgaaaact gtttcatgga gaacccaaac  64380
actggtgagg ttgttacgat cgaacctcaa acgtttgtgt ttatcggtgg tacgatcttt  64440
gataaccctg aactgattcg ccttaacccg aaatacctgg cttctcttaa atcgcagaca  64500
gcgatcaagc gagcacagct tctggatggt tgttggtttg cccgtattca agaggaatca  64560
ttcttccaac gtgaatggct ccacaagata gaatacaaag atgttcctaa caacatgaag  64620
tatatgcgtg catgggataa agctgtatcc gttccaagtg aacgttaccg ttatcccgac  64680
tatacggcat ctgttaagat gggtaaagat ctaaacggga acatttatat cttcggggat  64740
tatgattacg acgctataga cgagaagagt aaagttttcg gaagattccg acgcttacct  64800
ggtgacaggg ataacctaat cctccaacag gctaagattg atggaccaga tgttcagatc  64860
gttcttccaa aagacccgtc tggtgctgga ctcattgaat atacggaatc agctaagaaa  64920
cttattgttg aaggcttcgt tgttaaaccg gatgcaatgc caggtaacaa aaagaaactc  64980
caacgtttca tgccattcag tagtgcctgt cagaacggct ttgtttatat cgtagaagat  65040
tcatttccta acattgaaac tttgaatcac ttttataaag aattggaatc ttttaacggt  65100
gaacgatcta cagcaatgct taaagatgac cttccagatg ccgcagcatc ttgcttcaac  65160
actctggcga aagagacggc acacaaggct gtagcgatac ctgcaacaac aaatgcacct  65220
actggataca gtaacatgaa ctccaggcat ttcactaccg taagtactcc tcgtcgaaga  65280
taattgttga caaaagttac tttaaagtgt acaatgactt tatgggcggg ttaatttatt  65340
taacccttgc cctattgatc tttaagcaca gtgccggagg aagaaagtgt caacagaaaa  65400
aagacagtac actaagaagt cggattactg gaaacaaagt gcagtgaaca aagctgctct  65460
ctctccgtca aaacaggcag agaaagaaaa gagtttactt ctctctcctg aaatcgggac  65520
gattgggttg aactcaatca aagcattcac taacttcatg caaccgtatg aaacacgctt  65580
tcctgaaaac atccgtactt ataaggaaat gggtgaagac ccagatgttg ctaccgctct  65640
tgacgcaaca tacattttcg tagacagagc atttttcgac tttaaaataa aatacaacgt  65700
aaactctgcc aagtcaagaa aagctgcaaa gtttattgaa tatatgttac gcaacatgca  65760
agcaccatta cgtcagtatg tgagatctct tcttacttac aaacagttcg gttttgcatt  65820
tgctgaaaag gtgtttgaac ttgacgaaga tccgaagagt ccatactatg gctattaccg  65880
cctcactaaa cttgctttcc gaccgcaaga tactttggat atggcaaacc ctttcaccta  65940
ttctgatgat ggtcgcaccg ttatttcggt aaaccagaac atcactaata ccatgttggc  66000
tccaggtaac agtaagttgc aactgggtgt acgtcaaatc cctatgaaca aggttatttt  66060
tgtgggtagc aatatcacag aaaacaatcc tttgggtgta tcacctctgt tggctgttta  66120
tcgtagctgg cgtgaaaaat ctttaattca agaattcgaa gttatcgggg tttctaaaga  66180
```

-continued

```
tttgggcggt atgcctgttc tgaaagtacc gagcgatatt cttaaccgcg catctcttga  66240
tcctgccgga gatgaagcac agtccttacg agttctacag gcaaacattg ccaacctgca  66300
ctctggtgag caagcataca tggtattacc ttcagacgtt tatgaaggaa ctgttatgcg  66360
tcagtacgat ctggtgttcc agggcgtaga aggtgctggt aaacagtttg atacgcaaga  66420
actgatcaaa caacgtaaac tggatattta caaccgtttt ggtgcgggtg tattgataat  66480
gggtgacggg gacgctggca gttttgcatt gtccgataat aaacagaccc tgctctcaca  66540
cttcattgaa cgcgatgtag atattgttgt tgaagctatt aactctcaac tcattccaca  66600
agcacttcgc ttaaacaata tcttcctttc tgatgaagat atgccgaagt ttgttagtgg  66660
tgaaatgggc gatcctgata ttgaagtaaa cgctaaagcg atccaacaga ttgttgcagc  66720
aggagctatt ccacttacag cggaaattat caacgagttc ttagagaagt taggctttga  66780
ttatcgtata ccagacgaca ttgtttctga caaggataaa ttcgtagaat atatggagac  66840
attcatgcca gataaaactt cacgttctgg ggacggtatg gcgaccgcag gtacaggtac  66900
atccaccagc gtttcggctc ttgatccatc ggcagcaaac ttatcgaatt aaaaaattaa  66960
actttttga ttttaggtat tgacaaaatg acgaatatcc tgtagactaa gatttatggg  67020
atatttgttt ttaagaggtt catatggaac ttaataaaga tacactctgg gaactcttca  67080
aatcgttcag cggtatgaaa gaatcaaccc catcccaaca agattctaca cccctcaaca  67140
acctcaaaca gtaatcaaac ataataagtt tgacgaagag caaatgcagg ttattgaggt  67200
attgtattgt ccacctgaaa aagacgacct ccacggtgag cgtatgtctg atatggaaat  67260
caggaagatg gtagacaact tcaatgagaa tattactaac gtaagtggta atcttggtca  67320
catgaagaac acagacaaat ttgccccagt taaagcttgg gtgaacgaag ttgattgtta  67380
cattggtgac gaactcgttg tggaaggaac tcccctcgtt aaaatccaat tcaacgaccc  67440
tgaactgtat caagctcgta aggacggtgt tcttaaaggt ttgagtatag gtgcgatggg  67500
cgtgaaagtc aagaaggact aattgtggca aatacatatc ttactaacgt agacttttcg  67560
ggtaaagcta cggaagaaac tctgggcgca catatcgcat acactttcga ttttcaaggt  67620
ggtgcagcgt ctggttacaa taccccactg ctttttaaat ctgacggctc tcctgaagtg  67680
accttcgaga aaatcgaagc tctggctaag atgggtgaag acgttactga attacgtaaa  67740
ggttacattc agcaagtaat ggaccgcatc gccaacgctg taaacgaaaa gttctccaca  67800
tgttgggact gggtttggct ggcagatgta gactttgatg ccaacgttgc aatcttctgt  67860
tctgatcacg gtatgtttgc cgtaaacttt actttgaacg gtttagttgt tgaactcgaa  67920
gaagttgcta aacctgttgt acgtactacc gattatcaag ttgttgatgg tgacgttatg  67980
gtttccgtcg atttctttga agacctgatc gaagatgctc ttggcgatct tattaaaggt  68040
gctctgaaac acgatcaagt taaagattat ctggtgaaag cacacaatgc tcaaaccaat  68100
aagaactctg tggatgcaga ggctaacccc gcaggtgaca aatctgcaaa cacaactgga  68160
atcaataaag gagaattacc tttggaaaat attaacaaag aagaattcct gaaatctgcc  68220
gaattccaag acctgatgaa agcacagatt gctgaagctg tagaaaaagc agcgacagaa  68280
gcccgtgaac aagcagaact ggcagcacag gaaaagatcg ctaaagcaga actcgcagca  68340
gaagaacttc gtaaagctga actggctcgt atcgaagaag agtacaccac tgttgttaag  68400
tcctacgctt tcgtagaaga agaaaaagtt gaagctctgg ttaaatacct gatcgataat  68460
aaagagatcg ctgaaactgt tgttaacgca ttcgaaaaag cccgtgcaga agttgaagca  68520
gttaagaaag agtttggtaa agaacaaggc gctgatgttg ccaatgttga agttgttgcc  68580
```

```
aagtctgcat ctgaactgat tcgtcagaaa gctgccgaac tcaaaaaagc ccagaaacaa  68640
taatcttagg agattaaatt aaatggctaa aggaattact ttatctaact ctcgccagga  68700
attcggacac ctggttctgg gtggagtttt tagctctgac ctcggacact gtgtacgcga  68760
agtaaacctg gttaaaaccg caaccatgaa aattggttcc gtactgaaag ctgacaacac  68820
tgaagctgct gctgctgctg acgctgctaa agttctgctg tggactgacg ctctgttcgg  68880
tatcgatgat gttgcagttg gtgacacttt caccgccgtt gttggtgtac gcgacctgac  68940
tctgaaccgc tttgctgtat tctatagcaa cggtaatctg attgacgacg ctggcgtagc  69000
agcactggaa actcgtgatc tgaaactgac tgaaaaagtc gttttcactt cttaattttt  69060
gataggagat taatataatg ccagcagtaa ttttagatca ggttgttgat ttcagcccaa  69120
tgatcgaact tcaggatact cctgatacac tgattgccag cctgggtctg tttgatgtac  69180
agtaccatgc aactaccgtt gttgaaatcg gcaaacaaaa aactcaagat ggtctgatcc  69240
ctgcccgtga acgtggtggt gagcgtaact tcctgactat ggatactcca gaagtcaaag  69300
tgttccgtat cccattcttc ccactggata agaacatcaa agctcaagat atccagtctt  69360
tccgtagctt cgctatggct ggtatcaacg actctctgcg tactgaagca gaagtagtta  69420
accgttatat gacgcagatc ctgcgtgatg ctgcaaaaac caaagagaag atctttgctg  69480
aagcagtaat gggtcgtgca tacactggcg gcggcgctgc taactctgcg tacaactggt  69540
acaccgagtg gaacgttacc cagaaatcag ttcctgtaga ctttgcttct accactgttt  69600
ctccagcggc taccgttgag caagaagctc gtgcatacat catcgacgaa aaacaagacg  69660
gttctaccgc tactcgtatc gttgctctgt gctctcgtga gttcttcgct tctctggtta  69720
actctccgtt tgttcgccag gcttaccagt acttccaggg cactcctaac ctcctgcgtg  69780
accgtctgaa cggtaacatg gacgttcagg tgttcgaatg gaacggcgta acctacatcg  69840
aagatattca cggtaacatc cctgctggtg aagcatatgt tctgcctatg ggtatcgcgg  69900
atatgttcca ggcgcactac gctcctgcgg atactccaga actggctaac accgttgctc  69960
gtgaactgta tacgttcatg atcagtgagc accgtactgt aagtcttcag tctgaattct  70020
ctcttctggc agttaacgtt cgcccagaac tgattgttcg cctgaccact gcttaataga  70080
actctgttct aaaagaggct cgtccgtgat gggcgagcct tttttgttat atgaacacta  70140
tacaccgagg agattattat gtcaaaccca caattaaaac gttacttcag ctaccacgaa  70200
atgattcagg acttctctaa gctcgtgagc aatctggatg cagagaagac tctcacccaa  70260
gcacctccaa tgtctttcta tctgaaagat ggtcgtgttg ctttaggtgg taattttatt  70320
catttcttac aacgtctgcg tgaagagact ggtctgttgg ttcatccgtt tagtagcgaa  70380
gagcatatgg gctatttcct tgttagcttc gaagattaca aagagatcga agtcgaacaa  70440
gaagttctga aagttgaagc agtagattca ccagccaaga aacgatcact ccgtaaaaag  70500
taaggagaag ttatgctgat tgctactgaa ttggcaccaa tggttcgaat ccttgtctat  70560
aatccatctc aagaaacttt gccagacgaa gttctgattc agattatcca gacgtggatc  70620
gatattattg gtaacgccga ctctaataag tgtgctgttc tgtggaacag tttaatttct  70680
gttcttgagt acctgtggaa cactgatgtt ttaaataaca acagtcaaag tggtggtgca  70740
atgtcccgcc gtgaaaagat gggcgaagtg gaagtagaag ttaaatttag taacggtcaa  70800
gtagaataca aatctccttg ggaagatatc tacaacaact acctgaacgg cttaatggtt  70860
attccaggat gtactgttgg acgtggtgca acaagtcgtg ttctgattgg tggtgtagat  70920
```

```
gctcgtgaaa tcgatcgtgt caacagtgat cctaactctg tgaatggttt aggtaatgtt  70980
gccagtgtag atcgtaaaac acgtaacgta aactatctgc gaaactacgg acctgtatca  71040
tattatcgta gggacaaata atgaaaagtg agatcttacc aggcacagac acagactggg  71100
atacaatcat taaaaagatg atggtattag agaatgtgga aattgaagct ggtttccttg  71160
aaaacaagag acaccctgaa tcagatctca ctattccagc gatagctgct atccagcaat  71220
acggtaacga aacaaataat attccagccc gtccgtttat gactgacggt gctgtgattt  71280
ccagcaaaga gatagccaag ctgttaccga atgtttttgt tcaatacctg atgcgaaata  71340
aaggactcgg agtttttgag ccgatagcga aagcttctcg tgaaggaata gcaagagcaa  71400
tagcttccca acgatataga gcactttctc cggtgacaat taagattcgt cgtgacagag  71460
ggaattattc tacgcacacg ttgattgaca caggacacat gattaacgag atagactcga  71520
agatcacaaa aggcaagtct aaaaaataac ttgcataaat tttgtttttg atgtatacta  71580
aaaaggagat acaggtgtta cttgatcaat tcactctcct tgatcttacc tcatatcaag  71640
ggcgtagacg tgtctacaaa gaagctgtag gttctgttat cgccaatatg ggtagtaccg  71700
tagaatatga agagtttgag atagcggctg caagtctgca accaatctct ggaaaaactc  71760
taaaagcact gcccgaaggg tacagatcaa aggcgcaata tagtttctgg actaaaacag  71820
aaatgcgagg catccaacaa ggaacctctc aactatccga ccaaatcttg attgatggtc  71880
agtggtattc tgtgtactcc cttaaagatt ggactcgaac tactttccta acccatcatc  71940
attgtgtcgc catattagac gatcaaaaca atacatggga ttacgatcaa gagggaggaa  72000
actttggcta atatctacga acaaatcgaa gcgtatgaga atgctatcta tcttaacata  72060
ggtagtttcc ttcaagaatt aactggattg ccaatttacg tgatggacaa accgttcgtc  72120
caaccaacca atccatacct ggcactacgt attatcacct ccagtgattc tggcgggtgg  72180
tcttaccgag gcaaaataga gcaagacatg ttttcctacg agatggataa tacctatgag  72240
attgaactca tggctttccg tggaagaccc actactctgt tgagctatgt tctggctgct  72300
ctacgtggtg cagaggaatt aaaatacaag catctctatt ccaaaggaat gggtttcctg  72360
tcagcaacaa atatcacaca ggcaaacaca attctggatg gagataagac tgaagttaga  72420
gcgcgtatga ttatgacctt caacactcgt atgagtattg aggatattat gacaactcct  72480
attgaggctg tcaatatgca tattcgatca ttcagagata gctacaatga tcccacacct  72540
ctggatttaa ctctggatag aatttacgta gttcatgagg ttaatggcga atactcacca  72600
gtaactgatg atggatcatt atttaacaac cccaacgaat aaattcattg gaataagttt  72660
ctaacaggag cataaatggc aacttttcgt gaaaaggtag caaccgtaac tttactgtac  72720
ggagctacat caatccgtga aacccagttt gacattcccc tgatccttac tggtcagact  72780
gtcactggta atgcgattga atattacacc tcttctgacg cacttctgga agcgggttac  72840
ggtgttaatg atccagccta tatcatggca gttaaattgt ttaacggatt attcgcacca  72900
agtcaagtga ttgttggtaa gcgtgaagta acaaacttta ccctgacccc agcagttgaa  72960
gacagtgcaa catatgttgt cactatcaaa gaaggcaaga acaagaaaga tttcaaattc  73020
attgctgacg acactgcaac agcacaagaa atcgttgttg gtctgacaga aatgatcaat  73080
gcagacgtag tttatggtgg tctgtttacc gttgctaacg atggcgctgt gatcactgtt  73140
tctccagttg taggcaaata cgcttctctg gatgcaagcg gcttcgctaa agaaaccgtc  73200
tacgctaacg acattaccga agatatcgcc gctctgcacg atattgatag tagctggttc  73260
tgggttctgt ctgactccca cgctgttgaa gatattcttg atgtagctgc ttgggtagaa  73320
```

```
gagaatgata aagtatactt cttctccagt tcagacgttg gtatcactac taaagccgaa  73380
gacaacgttc ttgagcgttt gaatgatctc ggttacgtca acacctgttt cgctttgtgg  73440
atgagcgacg cggattctgt attcccagaa gctgccgtag ttggttctat ctgctctgca  73500
cagcctggta ctacgactct gcacggtaaa actctggttg gagttgaaat cgagaagctt  73560
ggtcagactg cggaaaataa cattgttcaa cagaatggta acatctaccg taaagaacac  73620
gcaactctgt tctaccgcga tggtctgatg gttaacggct tctttgctga ctacgtagtt  73680
cacgctctgt ggttcaaagc tcgtaccgaa gaatctctgt tcactctgtt caaacagcag  73740
tcaatgttgg gtggtggtgt ccgtgctact tccaatggtc tggctctgat taaacaagcg  73800
gttctggcta acccgatcca agttggtatt ctgaacggct ctatttctaa cgaagtagtt  73860
atttcagaag agactggtct gcgtgttgac ctgaagccta tcgtttacct tccttctcgt  73920
gctgacatga ctgattcgca gattaatcag cgtctggttg acggcatgaa gattgaatac  73980
gtttacgcag gattcttcca ttacgttaag gttcaggttc acgtcctgac caaccgtact  74040
gcaaactaat aatttggcgg gggaaacctc gccttatccc taaaggagat ccaaattgga  74100
taaaatgctt actggcgtaa tggcctatga tccttcccaa atcgttctgt ccctgggtgg  74160
atgggagccg tggggttttg caactgacac taaaattgta attgcaaaag ccaacgatat  74220
tattaaccca tatgctggta ctgatggcga tgtttctctg gctcttagcc gcaaccgtct  74280
cggcaccatg actatttctc tgcaacgtac atctccggca aacgaagttt tggcaactta  74340
tgctcaaaca atgtattcta ctcgtcaagt agcattcagc gtttacctgg aagatcctcg  74400
tggttactac attagcacca ttggttggat tcaatctcaa cctgaagaca ctatgggcga  74460
aatgattaca gagaaccagt gggttatcgg tctgaaagat gcaagcctgt tacgtaatga  74520
agttggtgta ggtgtgagtg ttcttaactc catctccgca ctgaccattc aataataacg  74580
aaagggcaga aatgcccttt ttatttaact aaaaagagag gaaactatgt ccgaacaaca  74640
agacgatact atcaaacaat atgcacgtcc agaagaaatt gtaaaaatct atttagatga  74700
aacccgtttc gtaaccttcc gtattctgaa gtggagtcct tcaaaggtct tcgaacgtat  74760
tccagaactc ggtagcgttt tagctgtacc tatgaccatg tacaatactg cccttatgtc  74820
ggctgatgaa gatctggaat ctcgtattgc aatggcactt attcaattgt tctctggtct  74880
tgaagagaag aaccttaccg tgttcctccg taagatctta gacgaagtat ataccgaagc  74940
aggacataat gtcgctgata acttcgacga actattcttt gctcacccag aacttgtcct  75000
cgacttgaca gcaaaagttc ttgaggtgaa ctatggccct tttttcaaac gaggtttcgg  75060
aaaactgttg acccagttcc aagcggttca ggatctggca acgaactaag tccagccatt  75120
cgtcacgcga tggaaaccgc agagaagact cttacgttga agtggtatga gttcattctc  75180
tgcaaggttg tgaagaatac ctcggaaaca cgctccaccc tggatcagta cggggtggat  75240
tatctattgg ggctgtacga gtacctcact tatgaggagt atattgaagc tctgtacacc  75300
aaagacactt caataaagaa aaagcaacaa gagaacgcta ctcaaatgca agacatgttt  75360
aagaaaatga tccactaaca tgaggaaaat actttgttag atataaacgc ggctaaaatc  75420
agtaacgtag tcacatttaa ggtggacaag aacagtctca aagaagccaa agattctgta  75480
gagagtgtta aaaagttcgc tgaaagaata cagcccacct taaacatgag taagtttagg  75540
cagcagatga aagagatcga aagagaaatg cgtaaagcgc agactttccc tgctcgccct  75600
gctccccctc ctactccaaa aggtggtgga actacctccg gtcctggtcg tccagctaaa  75660
```

```
ccaggaaaga aaactccaga agaacgcgct gccgagctac aggctcgtcg taatgattta 75720
ggcaatctcc gtatggagaa ctttgaaaag cgcggtatgc agtataccaa agcttccata 75780
gatgcgcaac gccaagccaa acaaatcatg gatgcttctg tagaatcgta caaacgtgga 75840
gatatcactc ttcaacgtat gaaccaaaca ctggcacacc agcttgataa tcttcgtcgt 75900
tctcaccgag agaaagtcaa agatattgaa gacgaggtac gtggtcgtcg tagagttcgt 75960
cgtgaattag aagcggaagc caaacaacgt caacgtatgc gtgataaaga gctacgtgat 76020
attgagcgta accataaacg tgaactggca cagcaacgcc gagataaaga tcgtcaatac 76080
tcgcaaatga gagatggcgc tttgggcctt aatcctcgca tgatggtttc atccatgatt 76140
ggtgcaggat tgtttgcagg tggttctgtt gtaggtaata cgttacaaac tgctaacgat 76200
cgtatcaagt tcataggtcg tggtgcagag aacgttcagg caaacgccaa cgccattatg 76260
acaatgactg cttggggtga acagaacggt gttgactcgg caaacattat taagtcaatc 76320
gataacctta aagacgttcg tgaacgcttg ggtaactcaa tgatggcttc tgaatgggac 76380
gaaaagaaag gaaaatggcg tggcggtgat aacggtatca acgatatcat gaacatgttt 76440
ggttggaacc cttcacaaat taaacacatg cagaacgatc cgttagcttt catccaggca 76500
actgtgaacg aaggtgagcg tcgtggcatg aactcggcac agattggtcg tttattagaa 76560
aatctgggcg atgatctcat gcattaccaa cgtatgttta gcaagaacgg agaaggcttc 76620
caagaaaccc tccgtatgct tcaacgtact ggcgctgcat tgaccaatga gcaaatggaa 76680
gcttctaaag agtacacacg cttgactgcc acggttggct tggtcgggca aggtatgcag 76740
aactatttcc tggaaggatt tatgaacgca atacctaaag acgagtcctg gttggacaac 76800
gtgaaaatgt tggataaagt agcgaaagat ttgggtgaag agatgggtaa gttaactgtc 76860
aatacagcta aaactgcaac tatgttcctc aacatcttta caggactgga tagcttcatg 76920
cgcgagaact tcggtttcat ttatgcagct acaggaaaag atgccagtgt gtgggatatg 76980
gcgaacagaa cctttaaccc ttttgcggcg gtttcagatg gacttacctc taagaatgaa 77040
gaaggtgttt ctatttggga taaggttgtg ggatattttg agaaagatgg atcaggatct 77100
gcggcaaaca attacacgtt taccggagaa gctattcgtc aagatgcaca aaatttccag 77160
tctaaagcta tgcagtacca gacaaatccg accttcaaca ttacgttaac accggaagtt 77220
gccttgacat tacaaagcga tgtttctcgt ctttccgatt acattgactt caatgctaaa 77280
gcttcttctg aatcgttcat gcagagcctg actttgcaga cgttaagtgg acagtcaaac 77340
agcaactaaa gaaaggggct tcggcccctt ttttcatttc tataatcccc tccccctctc 77400
atcccatatt tttacattga cataacggcg acatttgtgg tatcataatc aatatgggaa 77460
gatcttgcat cttcctcttt gcattaccat tactatgagg ttatcatggc agcaatgact 77520
ccacaacagt cggtaagagc cgtctacaaa tccgagcaag aggtgaactc aacacaaaat 77580
acgaataact ccgcctccac ggtgaaaggt gataacggtt tttgtatctt agccagtgtt 77640
tacaatagct caagtgatca atacatacaa aattttatgg cgattacttt cgactccgca 77700
ccggaagttg gagtaactcg ttcagccgat atcacaagct tccctgttga atcaggtagt 77760
acagtgagtg ataacgtcaa aataaacaac aacactttta aattgacagg tgttattaca 77820
gaaacgcctg tacgtttgat gcgtgatcag ctttacagtg caggggttaa tggaacacgt 77880
atctcccaag caatcgagta tttggatcag atttttgatg ctcgtcaacc gatagttcta 77940
ttgacagaac accgtacttt cgagaacgtg atcctgaaag gttacactta tgaatatcgt 78000
tcagaatttg ctatgcagtt taacctggaa ttggaacaga ttcgtttggt cagtactgca 78060
```

```
acaactaacg cgatagctgt gaagaccgct ccgaacaaat ctactggcgg tgaggttaag  78120
agcaaggctc caactggtgg tgctaaaatc actaacccaa ttaaccaaaa tgctgcaaga  78180
gatactaata caccgtcgaa taacggaggg taatcgtggc aacttattct aaagcaacac  78240
gaagcacaac aaactctgga tataaggctg tcttcttgga agaccgttct aattactttg  78300
cctggtattt gaagacagaa gaatatccag accaaaccta cactgtaaca ttggatggtg  78360
tagattatga tatacgttta cgttggaaca ctcgtgatga agcctggcag tgccttatag  78420
gtttatcagg agacgaaccg agcgtaacgt ttaagataac caacggactt gacctgttga  78480
agccgtacaa gtatctcgaa ggtgttcccg atggacaact ctacatgatc gatacggtaa  78540
agattaacgg tcgtcctggt tacacaacta caggaattga aaaacgtttt gttttggttt  78600
acatagacaa tctatcgaac caagcgtaat agttaagggg agattgtatg gcagaaagag  78660
aatatacaaa agcccctgtt cccaatctga acagggcgta taaactgttg attggtacgg  78720
caacgaatac cgtgcagaaa aggacaagca actcatcctt taaatcaaca gtagatttgg  78780
atactaaatt gggaagcact acaaaatctt cttctaattt gtatctactt gaacatcatc  78840
aaattacttt caatatcaag aaagataata acaaagatcc taaccaagcg gagattactg  78900
tttacaacct gtcagatgac acagtaaact acatcaaccg aggcattcgt aacaacctgg  78960
cagtagcttt agcagttgga tacgaagggc aagaattggt tatgattttc aagggtacaa  79020
ttcagtgggt aagtgatacg tttgatagcg tcgatcgtaa aactgttctc cattgtctgg  79080
atggaggtat taacatctct gaagcccgta ccagtcgtag ctaccctaaa gggacgaaag  79140
taaaacgtgt tgttgcagat cttgttaagg atcttgggac aacagaaggg aacattcata  79200
tcgacaacga tcagaccctt tcttctgcga cagcgatgtg tggaaatact tcacattacc  79260
tggaacacat ttgtaagagt attgatcata acgtgtccat tcaagatgga tctgtttatg  79320
ttacgcctcg ttctcaaatg tccaatgcaa gaagtgccta catcagtcct gaaacagggc  79380
tgataggaag cccagaacca ttccacaacg atatcaaacc tgccaagaag gtgactaaag  79440
cttctaagaa agccaagaaa cctacagacg gtgtgaagtt caaatgtcag atgaatggtg  79500
caatcttacc tgaaaaaact atctggctca agagtcgtga ttacgatggg ccatttaagg  79560
tggtgtcagt atcgcaccat ggagacaagg aaggtagtga atgggttaca gaagttgaat  79620
gtgtatctgt gtctgcgatc atgacgaagg aaggtaaata atggatgctt tgaactttgt  79680
cacagcgatg cgtggcatga tgacagaaca actggcagag gtgcacacct cattaccagt  79740
acgagttaca ggtgttaact acggtgcaaa aacactgaca ctggaatcca ttgtgaagaa  79800
tacgcgatca gaagaagatt ctatcgacta tccaaccttc cacgatgttc cttttatggt  79860
taacggagga ggtacagggc gtatctcctt ccctattaaa tccggcgata ttggtgttgt  79920
tattttctct gaacgagatc cttcgaatgc aatgcaaact tctggagaag cagccacaac  79980
gactacatta atgcagcctt gcggtttata tccgatttgc tttattccta agatttccac  80040
aggcaccgat tcaacagaag cagtagattc cgagaaggtg gttatttcaa ataacaaaaa  80100
cacatatgca tctttcgatc cttctggcac catatcgata tggaatagcc aaggaatgaa  80160
gattgatatt actccttctg gaataacaat gacagacggt tccggcaccc tggatttgac  80220
aggtggtgtc atgactttca aaggcacgtc tgcaaacatt aacggactac agattgatca  80280
gaacggattg atgacagacg gtaatggtat tggcttccat acccacaccc atacggttcg  80340
caacattcag agcggaagct caagtgcgga atccttgaaa ccttcaggag cataataatg  80400
```

```
ggtatcccat atgatttaaa attgggatca gacaacgacc tcatcatgga tgatggggat  80460
cttgttttga caaccactcg taccgagatt gcagcgcaga cattagggat caccctcaag  80520
acatatcgtg gagaatggtt ccttaacacc acgttcggtg ttccttacct gcaagagatt  80580
atcggtgtag cacgaaagaa agatattgtg gaccgaatct tcctggcaga gattgccaag  80640
aatatttata tcgacacaat caattcttac aaatcttatt acgatcgtga ccaacgctat  80700
tataatatgg atgttgttgt cacagtaggc gcagacacag taacaacaag tttcaacacc  80760
caaccttctg aagaattcat ttatccagaa gctggcgatg acaatgcggc aatcacttgt  80820
gaagcataca ccattgttga atcttctaac cgtctgtacc gcttcattaa ctttgttggt  80880
ctgcctgaaa atacttattc tacttggtgg aatgagtggg cgactgaaac cgctgtcgaa  80940
cgtatgatgg ttagcgattc aggttcagtt ctttcaacaa ataataactt cggccttacg  81000
gctatgacag gagtataaga tggcagattt aacaactatc aaagttacag acttggcgca  81060
aaccacgtct gtttcagatg cagatttctt tgtaacggat caggcgggga taaccaagaa  81120
aacgtccctg cgtgttcttt tgaatggtgc tggggttact cgtaaccgtt taagtacccg  81180
tggcaccgtc accagtacct tagctttaga cttgggatca gcagagtatt tttatgctac  81240
cctctcttct gcttcttgta cgatcagctt tacaaacatt cccgttacca cagcaacagt  81300
tttaaacttt agtctggctt tgcgtcaagg tagcggggca aataaagtgg tatggccagc  81360
ctcggttaaa tggagttttg ggcgcacacc tgttttaagt tatcgtcaag gtgcgatcga  81420
tacttttgaa tttatcagtt tagacaacgg tgcttcttgg attggaagta tggtaatggc  81480
gggagtgatc taatgtctca aattaagcac aatattgata acactttcca gctaatcgac  81540
ggattggtac agttcttaga aagaaatact gggttgacaa ttgatcctac ggttcaacat  81600
tacgtgatca acccacaaaa cattctggct aacaaccgtc actttatcaa ctggacagca  81660
caggaaggtc agccaaacgg cgatgctaca acagaaggtc aatctgtgct tatcacaggt  81720
tttgcctatg catacttagc caccggagat agcaaatatc tggactccgc taagaaatat  81780
tggcaagcct acattgacgg attcttcggg gggcaaccta tccccgatcc tccgcaaaag  81840
tatcgtccta actggatcat caacgggaag gaaccccgtc tggcccacta cccattaacg  81900
gatgatgggt atccaactca cgggggcttc aaaggaagtc tgatgacttg gacaaacggg  81960
cgtaccgtga ttcctaaagg tgctccacac tggggagaat acttggataa agcttggttt  82020
gctttcaacg gtaacttagg atggaactct gttaatgcca cagtttatgc gaccaacagt  82080
gacggttcta ccaactggcg tgagtacgga gatcaatggg atgttgattg gattattgat  82140
cggttgggac gtaaagtgga ctgggatgga aacattctat cacaagggca cactcccgct  82200
gaatacggta ctgtccaact gaagaacacc acagtcaccg gatcatataa attcaactat  82260
gcaacatgta accctgtaga gcatggtggt tatctcatgg gacgtaacga gatgtggcat  82320
aaccgcccag tcaacgtacc tgtagagatg ggcttccaag ataacgcctc cgatgctgaa  82380
acttggtggt gtgatgcgaa ctatctgatg taccagatca ctggcgaaag gaagtattgg  82440
ttgtgttggc agtcttcatt actgctttgt caagactact ccaacattga tatgttcgat  82500
aagtttttcc gtaagtcaac tactgcgacc atcccgttca cagatggcat ttcttatgat  82560
tacagctacc catctacagc aatcccaact tactccaggg attcgttagg gtacacggtt  82620
attcgtcaga acgtggcagc acaaactaca ctggagcaac aggctgtctg gttccgtgtt  82680
ggggatagct ctaaactgcg tgttcagttc caaggtgttg atgatgcagg ggagggtatt  82740
gttttccgtc cagagttgga gttgagcaag acgaaaagtg agactgacac agttacatat  82800
```

```
cgttgtggac tgcctttagg tgcagccaac atgacgacaa tggatattcc tctatccagc  82860
ttcatgcgta ctgaaccagc taatggtggt gtatatatta ttgcagaccc acgaatgatc  82920
attgactggg gtgccaatac tgtggtacaa tacaaatatg caacagatat agctggaacc  82980
aatagcgacc agattgtttc tgcaaacatg gacgccgatg gcgggataac aatcggtttc  83040
tggttgacac caactaaaac agcaaactta aaatctatca cttaccgttc ctatactgat  83100
gatttcaata tcacaataac ggacgcgaat gggtggagat ggtgggcaat gctggagaaa  83160
actggtggac tttggtcaac taaaacgtta accgcagcaa gtttccagtt atcagcttgg  83220
caaccagatc attcagatac agatcccaag cctacggtta tagacctttc tgctgtagag  83280
cagattaact tggttctgga tacagaccct gcaaacggtt tgacaggcgg cattgacttc  83340
tattgtgtta acgatatacc ttctcgttac tcttctgctt ccggtgaaga ttacacgatg  83400
tatttcagga tcacagttca gtctgaacac ccgcacactg ctaaacttgg tgattgtacg  83460
atcattgact acaaactgaa tagcctgaac tacacaccag gaattattcc gttctcgaat  83520
attagtgacc ctaatacatc tttgtatgat gggtggcgtg ggattccata tcctggctac  83580
cagtatccgt ctctgtattg tttccaaggg cgtgatattg attggacaag actgaacaac  83640
agtattgact tcttgtacga ttcacaaatg tggttctaca ataagttctc tcctgtaatg  83700
cctggcccta tggcgcaagc ttatgtttgg gatcgttggg atgctttgaa gtatggtact  83760
aagaatgagt tcaccatgta tcactggaat gataaagctt gggatggata cgaggctcgt  83820
gcgttctatt gtgcttgtca tacagtttac gaactgaagc agcgtgggga agatattcca  83880
accaagcttt tgactgtttg taagaactgg atcaactatc tgaaatggtt ccaagataac  83940
aacgaaggaa gaacaccgac aatcttctac cctactggag aggtaactgc tcctatagac  84000
gactttacca gccacatgtc tgcattgttt atggcgggtt gttctatcat gggtatggca  84060
ggatatgaca cagagatccc taatcttaaa atcgtagcag atcgttgctt cgaactgatt  84120
caggaaaact acattgtctt aggtccgaac cacatcatga atggatgttg gagttctgca  84180
ccaagagcaa gcacagataa cggggtattc tttggcttcc acgctgggga acttttacgt  84240
ggttttggtt tatatgcttt atacaaaaaa ctgaatccgc aaaatgccct tccactctta  84300
gactcaagca atattccggc gcttaccgtc ttgacaataa aagacgtaac cgtggatgcc  84360
actgaataag gagcaaaatg aaacaggcaa catttactgt cacaagagac aaacgagtaa  84420
atgtgagttc gttcaactac aagactgtcg atggaacggc agtctccggc agagattatg  84480
tagcgaagtc gggaacctta gtgttccctg ctaacgccga ctctgcaaca attgtggttg  84540
atgtttacga acgaccaaaa aactcaatag atattaactt ctttttagaa gtttctggta  84600
tcagcgaaaa caacacgatg gttgaaacca agatcgagtg tgtcattacg acgagacaag  84660
agaacaccac tccgattaca tggacctcaa ccaaagctaa aatgttctct cctaagttct  84720
ggactatcga ctcccaagca acagagagtt gttccataat ttccagtggg gattccttta  84780
cggcgtactt tgttaaccgt acagcagcag gtttggcagg tgttctttgg cacacaacag  84840
acacctttga tcataagggc gtaggttttc ttcctcacca agatttaagt gaagagaagc  84900
tctggtttaa attagaactt agtgcaaaca tgccagggtt caatgatgct ccgttggtcc  84960
caactattac tttaacattg gttgataaga cgattcacta cattgatttg agctattatg  85020
ctttcaatgt atcagaagat ggcaaaacag cagatatccg cttagacttt agcaatatta  85080
agtctggacc gaacaatgat attgaagtgg acaccacaca ggtggacaat ttcttcttct  85140
```

```
ctttgatcac gacacgctac caagacataa cagaaattgt tcagatgaac aatatgcagt  85200
cgtcaatgaa attcactttg cttgaacctg acactgggtt tagtcagatg gacgttagca  85260
atttggtaca agcagcacac gatattcgta tgtgcacatc ttacgatgac atgtataatc  85320
ttacccctga acgtgttatt tccaacactt atgctttagg gtatcgtggt atgataaacc  85380
attacaacgg aatgtcgcac tactaccagt ttgaatggga cggcaatgat ggctggcaat  85440
taaacacttc cgtgtttctt aacccagcga ctgaagcgtg gttgaacagc ttccatgcaa  85500
tcgccaaagc ctccggctac acagttatga actctttgag ttttgaattg atgagcacag  85560
tctgccctgt tgagtgggtg cagcacgatt ggaacgatgc tttagctgct acaggttatg  85620
tgcctccgag ctatgtgttg tctcctacaa ttgatgaggg tatgcaatat cttcagaatg  85680
taattaacaa gatcgcctcc atttccacaa ctaacgacat tccggttgtt attcaaattg  85740
gggaaccgtg gtggtggtac aatacagcta ccaacctgcc ttgcatttat gattatacga  85800
caaaactggc tttcaataca gaaacaggtt tgtttgcaca agatgctggg acgattgata  85860
actataaaac aggaagccca tacgatcagt attacgagtt cttgtctcgt aaattgggtt  85920
tgagagttac caagtttgca acggacacac gcgctgcata cccaggcgct caagtgacat  85980
tacttccgtt cttaccttcg atcattggca acgggttaat ggagaaagta aacttcccta  86040
aagattacta cattccagaa gctttcgatt tctattgttc tgaatgttat gattggttgc  86100
ttcaaggtaa gatgattaaa gcctatgatg ccgtaacaat accgcacgag actttgggat  86160
tcccttacga agatattcac tacttggctg ggttcgtacc agatgccaca ttagcaccgt  86220
tgtacggctt tgatcctgat tcaaattacc gcacatattt gtggaaaatg atcatcggga  86280
acatagtcct gaacaatagc aagttcgaag gtcttaagca atatatatgg gcttacccac  86340
aaataatgca agactctatt actgtggtca actctcattc gcaagttttc tatatgggca  86400
atgttccttt aaacgtttac ctacaggata cagtttatgc ctaaagagaa tgggtttaag  86460
aagtttgttc gcggaatgtt ttgtacttac cctggaaacg gggtaagttc cactaaagta  86520
tggaacgccg taggtatgat gacaatgaca ggtatgttca tctttttagg aatagaaaaa  86580
gaaattcctg aatggatggg ctgggctttt gtttttatgg tcactccctc acgactaatg  86640
aaaaatctaa tagacctgcg ctggggtagg tcttccaccc ctgaacacaa caaagaggat  86700
gagtaatgga tgaatatggc ttaaccgatg cgggatttgt aatcccgaca ttcgatgatg  86760
tacttaacaa ctatatgact gcacttaaga acacttttgg tgccgatgca gcgacttcgg  86820
aggatactgt cttcggacag ttgttccgta ttattgctta taccgactac acattatggg  86880
aaggaatgca aggagtttat aataccaga cactggatgg tgctgaaggt atttaccttg  86940
atgaaatctt ctccaagcgt ggtttctatc gttctgccgc tgcacctggt tcaggttttg  87000
cttatgtgaa aagcaacaac aaagcccctt ggacttttga acttggcacg gatacgtatt  87060
ttaatgcaga caacgacatg aactattatg tcagcgcacc taccatgttg aatgctaaga  87120
tagcagcata tcaaatctcg cgtgcgaatg caacagctac aggagtggct aacataactt  87180
tctacgcaca aagtgcaaat gatggtggtt tgaatagtcg tgtactctcg ccagcctctt  87240
cgacattcat tacagatctt gcaaacttta ttcgagacaa cctctccact acggatcgtg  87300
atttaatcca tacagacgca agtaacgttt acgttggctt cgcagcagcg ggagatgtag  87360
aacctgttgg tttggtaaca ccaataaaat tctacgcttc tgttcctgtt gggacgaagt  87420
ggagtgaagt tccggtggta ggatcagaag cagggtacaa tccggtaggt gtggaatcca  87480
tttctggaat ctcttcaacc ttcacaggct accttgattc tggtaacttt tatgctttct  87540
```

```
cttcaggacg agatgtagag acagatgcag agttccgctc acgtttcaac gataaccttg  87600
atgaagcaaa cgcaggtaca cgcgcggcta tcattaaagc tttgttgcag actgacggcg  87660
taaccaaggt taagatttac gacaacccaa caatccacga tcaggaacat gcacctgcaa  87720
tgagtttcca gacaatcgtg tacggtggga gtgccgaaga agttgctaaa gtaatttacg  87780
acactaaacc aatcaatacc ttgacttatg gcacaactaa cattactgtc atgacggaag  87840
atggtggaca agagattatc cgcttctctc ctggtgctac tgcaacgtac tccttgaaac  87900
ttgtatacca gacaatcaac ggtacaacgt taagcggaac agagaaagaa aacattgttg  87960
aagcactgga taacctgcaa gcctacttcg aattgggttc ttctgtaact aacgaccaga  88020
ttaaaggcgt tatttatgca gcacttgctt ttgggcgctt gacttctctc cgtgtttatg  88080
ttaaacttaa taatgaagac gacagtaaat atacagaagg aaacattgtt cctgcctaca  88140
atattgtccc gtctttcgac cttgataaca tttcctacga gtatggagtc taaaaatggc  88200
agtgagtgtt gaccatgtaa cgacttggga gaatatcaat gaagacgtta aagatctgtt  88260
gattgaagat tttaaatctt cccctaacat tgtcaagctc ctctacatcg tatcaagtga  88320
aaagcaaaag atagatcagg caatgatcta tcttgctaaa caccgtttaa tatctacagc  88380
cacaggggat tatcttgatc tccttggtga agagatgggt attgaacgaa atggttctga  88440
tgatgaagag taccgcacaa ttttaaaaat cagggcttat cgtgttgcct cttcggggac  88500
tcgtggggac attattgata tcttcgcccg tttcacaggt acaaaacgag atacaattaa  88560
cacatacgtt gggttgaata aatcctttga tgtgttcttt tataacttgt gtcttcagtc  88620
tgatcaagct cttgagcaac ttttaagtgt gttcccaatt ataagcaact accgactggg  88680
agctaaagcc ggatcagctt ttggattcac ctcttattac gctaccaaag atcctcacgg  88740
tattggtggt ttgggttcct tgtacttgga atctacagga gatgaaactg gacgcatgtg  88800
tatgcttctg aaacaaatcg attaaggagt tccaatggcg aagccaattt actatcctga  88860
ttgggctgta gaaacagtta ccctcccagg aacacaaaac atgaacaaga ttcgacctaa  88920
agaaatcatt cgtaccgtgg gtatggatta tggtcaaatc atgacatgtg aagaaatgaa  88980
ctggatactc aacaataacg gattatggat tcgttacttg gttgatgaat tccttccaac  89040
attaccaaat acatatcttc ctctggtcgg tactaagata acaatggcag gggatgcaac  89100
aggcgaagta acctggaacg ggaatgcagc agtaacgctt tctattcaag ttgtagacaa  89160
cagtcacaac cacttatcct ctaacatcac agatgcaaca agcaccacag taacccctaa  89220
tgtattggtt aaacgtgacg gcggcggcgc tatttatgct ggagatgttt acgtaaacgg  89280
tacagctact tcagatcctg ctacaatatt ctttaaaaac tttgcagggc aaactaacgg  89340
agagatttct tccgagtaca ataatggcgg tcatctttat atataccgca ggaaccctac  89400
caatggtaac gtatcctgtg cagtacgttt gtatgatggc ggttatgttc tgattgataa  89460
tccacaatct aacagtggac aagatactgg gaacggtaat gctctggttc gtttagatta  89520
cttgaactca cgtttaagct ctttacagaa caccttgcaa acgaatatta actctgttca  89580
aaacaacctg aacaacgtta acaataactt gaactcacgt attgacagcg tgaacagtaa  89640
cttgcaaaac cagatcagta acaactataa ctatgcgaat ggtacttttg ttcgtgacat  89700
acgttatacc agccaaggcg tatattaccc accaggtaac gaggtgtctt ggacatatat  89760
ttgttcttcc ggctatgttc tttctggtat tattgttcag gaaacaggtc gtagttctgc  89820
ggataacatt ggtggtgttt acttcaaacg tctccagcga aacgtgaacg gaaactggta  89880
```

-continued

```
cgatattgga ggctaaatgc tctacactaa ttttaagaag tatatcccag aagatcccgc  89940
cctaagagaa ctcgtagaag tagagaacat tttgttccta ctttgcgacc agggtattga  90000
ttggtatgaa ttgcgcgatg gtttgctaca gaacgataaa atgaaagtcg tatttgatga  90060
gcaaaatcgt atagtttttt ggaacacaga ccctactctg ttgtgtcccg aaaacatgtc  90120
tcttgcacaa gttgatttcg agattacaag cttcgaagat atccgtgaca aggttttaga  90180
cttagaaact cttacactga aagataaaga gtacagtcgt gaacaaatga ttgtcaaggt  90240
ttctgctgaa ataaagaata agcaagaaac agccgttgcc cttatcactc ctttgcaata  90300
tgcaaaagac cttgatatag caacacccga agaacttgcg gaactgaagc aactccagat  90360
ttatgttgtg gaattgaacc gtgtgcctct tcaagaggga tatccttacg aggttaactg  90420
gcctacccta ccaacaaaat aagggatgca aatatggaat ttcaagaagt ctggggtctt  90480
gctaaggacg caatcatccc tctaatcggt ttaatctggt tcctgtttaa acaaaaaata  90540
gataagtttg gtgttgattt ggagaaggtc gaagacaagg cccgtgagtt ggaaaagaaa  90600
cttgttttcg tcgaatccac ttacgcaacg aaagctgaac ttactcaaat gctgaatcag  90660
attaactcta cattactggc gaataatact actcttgagc agaagattga aaaaatcatg  90720
gacctcaaga atgcaacgat ccagatgatg ttagaggata ttactaaacg tacacagagt  90780
aagggttaat tataaatgac actattccca acatatcccg ctacgtcctt ggaacagggc  90840
gtagatctgg taatcttctc ttctaaccag atacacgata tcatcaacgg aagcgcaaca  90900
gaaagtattg atacggaatc aggattgatt ccgactttac gtaaggcttt ggttgataac  90960
ttttacttca aaagtcctat tgcctgggcg caagggacta atgaaacagt attcaaccaa  91020
ctccgtttct atcagaacgg aatcttgagt ggatactact acgctccagc agcaacactg  91080
gtgaacccta tcccaatgca agggactcca gtcggggaca ataactgggt gctgtgggga  91140
atgcagactg aacaactgcc aagtgaagtt attccttggc tgtatacctc tgcaacaggt  91200
tatgaaaaag taatcagtcc tccttatgtg ttcgatagtg ctattgtgac tatcaacggc  91260
gttatccaga tcgtgggtga tgcattccgt attgagaaca gtcagatcat cttgtccgaa  91320
ccacttggac atgatcctgc aactggatta cctaatcagt tgtttgctta catcggtaag  91380
attgtagcaa gcgcagaaaa cgaccctaac ctcgaaaacc gaatttctaa cctggaaaca  91440
actactgaaa cattgaccga agatatgaac gctgttcctc ttcagacaat cgctcgtaaa  91500
tatggtttcc tgaactatga agtggcttac gcaaaatcag gacaagcttt aataggtctg  91560
aaagccctgt atgatgccac taaccaaata gcttacaccc tgccacctgg tttaactggg  91620
acatttgtta gcttatcaga tactggtgtt cttacccact cttctggtac tgttgacttg  91680
gcagcattag cagttgaacg tcagcaatat gtacatctgc ctaccagctt cggtaatgaa  91740
gttaccctga cactgaaaca ccagactatc ggcatgggtg caggtcgtta tcgttgggct  91800
ggccctttgc caaaaactct ctctgcgagt gacacccttg cctcctctgg cggcgtaggt  91860
ccgaatgctt gggtactgac aaacacagaa ggtctgttaa ctccacacgg tggtaagttt  91920
gatgatctgt ttgatgttgt ttacctgtcc gagtttgcaa acagtgcagt gtacgctact  91980
ccagaagcag ctttccaagc ggctctcgtg gcaacagcag caaccaagag caagatcctg  92040
aatgcttatg gttgtgatat gaccttcact acaagttctt ttgatattac tgggatcacc  92100
ctccttggtg gtgtcttccg tggacaacgt gactaccgtc tacaaaactg taaagtggaa  92160
ggtacaactt tccgcaactc ccgtgtaatg tactggggtg gcgatgtgcg tatctatgac  92220
tgcttgtggg atggtgcacc tcgtccagga caggttggta gcttggtatt ccagggcaac  92280
```

ccaattccag gtacttttga gattgacaac tgtacgttta aaaacggact ttacggtatc 92340
cttcaacaag gtactggcga accagttagt cgcggtgtct tccgtaactt gacgtttatg 92400
gatatgcagg gcgatgcaat cgaactgaac gtaatcaaca agcattacga tgaaggttgt 92460
gttattgaga acatctactt gtctcacatc gacggaacta acgcaccaat tcctctttct 92520
aactggggta tcggtatcgg tgtagcaggt aaaggtccat acggctatga cattccagat 92580
acgcagtatt gtaagaacat tacaatccgt aacgtatttg cgaaacgttg ccgccagatt 92640
gttcacgtag aagttggtcg taacatttct atccagaaca tccacggtga tcctgaccaa 92700
acagtttctg ttggtacagg tctggcaact ggtgctgttg taatgtacgg ctgtaaagac 92760
ttcacgatcg atggtgttta tggagatcct gttacggacg acaacacttt accaagtgca 92820
atccgtatga tctacctgga gtggggtact aacgcagttt taggcgaaga cggaaaacct 92880
gtggttcctg cacaaggtcg tccatcaaac ccttgcttca actactccgt gcgtaacatt 92940
catactccta atggacgtgt gttcgctggc gtatcagcgg gtccaggttt tgagaaccgt 93000
gttagcttcg ataacatccg ttgtaacgct ctgcaattat ttggtatcgc ttcttggttg 93060
tcaatggcaa acatcacttg taactctttc gagtgtgtgg gtcagcctga atctggtcca 93120
ggtactttct acgatggttt cttccgtaga gagaagtccg tactggagat ggtgaacgta 93180
aactgctatc caaatggaaa cacaatggta actggtcgtc ctcaatggag ccgttgccgt 93240
tactcggata tacatcgtat caactgtaac gttgaagcga atatgtatac gaacatcgca 93300
ggtggtattg gtgctctggt aggctctact ggtaaatctt actacatcga agcaatccca 93360
ggtcgtaaca ttgacgggat gcacttccca acagggaaag agttcgataa aggagatatt 93420
atcgttaaag cagataacac gttcttcctt gtaactacaa gtggtgcgta catcccagac 93480
attccagcct tcggtatccg agcgacaaat gttggtgata aatcgattgt gcagaacctg 93540
acacctaacg gtacagcgac aaatgcttct tggttatatc attacccact gtcagcaggt 93600
acacgtatcc gtatcccagg tgcgggtcca ggcggatctg atttggacac agtaatcact 93660
cgtgcccctt atcaggataa cgatacttgg accaacccag tgaaggtgga tattgcagat 93720
cctatccaaa cagcgacagc agcaggagta cgtatcacaa ctattcctaa tagcgcaagc 93780
aacgttgcgg ttggtaacac tgcggtaatt cgtcctactc cggtgattga tactccgacg 93840
acataagtga aagggggctt gtccccttt taactcccaa cgataaatga atgattaatc 93900
aggagtaaat aaatgctttt aacaagaccg aatagctcga ttgcagatat ggtcgaagct 93960
acgtaccgta aacgtcgaag ctttgcagcg ggatttactt tacgtaatgc ccgtgaagtt 94020
ctgcttttag atgatgacgg caactattat aaatggaaag gtgcttttcc gaaagttgtt 94080
cctgagaact ctactccggc aagcacaggc ggcattaact ccactggatg ggagagcgta 94140
ggcactgctg atgatatcgc agtaattaat gcccgttttg caataatgca gcaagagatc 94200
aataacatct cttctcaaat ccctgaagct gggaaatcag cctaccagat tgctctggat 94260
aatggtttcg taggcacaga acaacagtgg ttagcgtctc ttaaaggtga cactggcgca 94320
caattaaata ttaaaggctc tttgaacaac atcaaccagt tacctacaac aggtaatgct 94380
ttaggagatg gttggattgt cggagatgca atttacgctt gggacggcgc aacttggaaa 94440
atgatttctt ctctgggtcc agaagggaag tcagcgtatc aagtgtggtt gtcagtaggt 94500
aatactggta caatttacga ctatctggca tctttgaaag gagatcgagg ggatgttggt 94560
cctcaaggcc cacaaggggc agcaggtctt aatgcgaatg gttttgatta tcgtggggat 94620

```
cttgactcta ctgccaacct accagcagcc aacccaaata acgtaagcca agcttactct  94680
atcggaggct acctttatgt ttccaatggc gaagactggg ttaatatggg taacattgtt  94740
ggcccacaag gtccacaggg tgaagcaggt actgacggtc tggatggaac agatggcgat  94800
gaagggaagt ctgcttacca atcttggtta gatatcggta atacagggac ggaagtagat  94860
tttatcgcag cgatcaaagg cgagaaaggc gatcaaggga ttcaaggtga acaaggaaat  94920
caaggtgaag taggtccaca aggcccagta ggtgcaacag gctctggctt ggaaatctta  94980
gacgttctgt ctgatgaatc tcaactccca gaaacaggtg aagttggtga tgcttacatt  95040
atcgacaaca acctttatgt ttgggtagaa ggtgctacag actggatgaa cgtgggtagt  95100
cttggtggaa catccattac cgctaaaggt cacgtaccaa acggttctgc actaccaacc  95160
tacaacaact atggtgacgc ttatctgaca gaagatacca gtaaccttta tatttacact  95220
tacgacaaag atacgaacac cgcctctttt gttgatatgg gtagtataaa aggtgataaa  95280
ggtgacaaag gagataaggg tgatccaggt ccagcaggta ctaacggaac agatggaact  95340
aacggtacac cagggattga tggaacagat ggtaaggacg gggcgcaatg gtttgtagct  95400
gcaaccaacc caaccaatgc tgaaggtgtt attgacgact acgctttcaa cactgcaaca  95460
ggggctgtct ttaagaaaac cgctgctact gtttggacgc aagttggtac acttccaagc  95520
attcctgaag ctcctgaaga tggtttaatc tatggacgtt ctgatggaga ttggattgaa  95580
atcagtggca gcgatcctac ccaagagatt gcaccaacga aagtcagcgc aggttacatc  95640
gagttggaaa caactaatgt agcaagttca ggaacggctt ggactccttc tggggccacc  95700
aacatgtacg tggtgaacgt tacagacgca ttgacgatag gagcatggcc tggagtaaca  95760
ggaaccacaa aaccgaaagc tttctctgca atgatttacc ttttgcaaga cacaacggga  95820
cacaccgtga cactggatgc gtcttatgga gcacttaacg atacggaagt aggcacagca  95880
gcatctgctg taacaatcct tcagttaacg tattgtggtg tgggcgatat cgtggacatg  95940
gttgttgtaa cacgataaca gaagccccgc aaggggcttt tcttttatgg aggataacaa  96000
tgtttccaat cccagtaatg atgattatga cagatgctgg agtaatacca cttccagcag  96060
ggattgtcaa gaaagtaata actttagatt acccagataa cgcgggaaat tctaacagca  96120
gtctggccct tttgctcaac gatgggcgac tgttcacgca aggtgccaac ctttttgggg  96180
agatcgcaga tggaacgcgt agctctcgtt tcaatagctt ctacctggct tcaacggtag  96240
cttcggatgt gtttacagca gatcgttgct tcgttattaa actacaaagc ggtggatggc  96300
aatacgcagg actgacagca ggtttggtag gtgcaaatgc cgcaggagga tcagatgttt  96360
gtgcgacttc ttggacaagt ttcccatctt caattacagg aacaatcacc ttagccaact  96420
tgaaagaagt caagggaggt tacaataaca cgttgtggtt gatgacaaca ggagttcttt  96480
acggatcagg acaaaatact gttgggagtt taggttcaag taacacaaac caaatatcta  96540
ctccacgtca gataacaagc gttgctttgg cgtttgatgc aggatacaac caatgtactt  96600
acctcaataa tgtaggagca cttcgtgtgt gcggggcgag tagaggggtt gcagggaaca  96660
acagtacaac cacagccttc gttacagcta caatctcgac tactgaaaca gtgtttgtta  96720
aggattacat caacacagta tctcaaacga ttgttattgg agatacagca gcaggagcag  96780
gatcaacaaa ctacctgtat gttcgttcca atacggcaac aacgtataca aagcttgaga  96840
acttctcaac aggttttaca tcatgggtaa tacctccgag tagacattcc ttctttgtgg  96900
ggataaataa cactttgtgg gccattggta agaactacac agcgaatctt ggcttaggat  96960
acgcttctgc gagcacagac ccactacaag tcggtaaacc aatcaaacct gaaggtgtgg  97020
```

```
cctcttggaa ccttaacaag ctcacaagcg tacacacgct caatatggac gttactaatc  97080
agttgggcta ccaaggtact ttcattgtgt atgatggcaa cctcttctac tccggtgctt  97140
gggtagacgg aaaagcttct tacctgttca acagcggtct taactctaca tctttctcac  97200
ctataactac agatactgta acagggacta ccctggcaac aggattgtct acagattctt  97260
taggtatttg tattgttggt gggaccaaac agttaaccta ttcagtaagt ccttcaggag  97320
gtaagctctt caacgaagct tacacaacat ctgccccagc ttatatgacg atatcttcct  97380
ctggtttgat gacgtttgtt gctgaaggtg gttttgatgc agggatgaca gcattgaacg  97440
cagcaggaac aaccttatcc gacagttctg ggggatatgc ttctgtactg ggggtgtata  97500
ctccgagcct ttcagctatg gatgaaggaa caacgcagac attggtggca gaaataactc  97560
cagcaggggc agagaacctc cctggcatgg ttgttgagta tttctctaat gaccctacgg  97620
tagcaacagt tgaccccgtt acaggcgtta ttacagcggt tgctgatggg gattgtcgta  97680
tcggttgtag agcaacttat caaggtgtgg taactgccga agatagttct tatctcgcag  97740
tgaatgctgt ggtgattgtg atggactatg atttgacgca agaaactctt ccggcaggtg  97800
taagcgtaaa caggagtaac cgttatgcca gggcttctgg agatatcctt gtacctacag  97860
agagttctgc tcccgtagca cctttagaat atgttggtac aactccacaa ggtagacgtg  97920
ttgtagcagc caaccgtaca catatcttta tcaacaataa cttgacaaca gcttccccgt  97980
ggttgaagac gaacttgaca gtcacagcat caacaatcaa ctctcctgtt ggaactacgg  98040
ctaacactta caagttaaca ccttctacaa cttcaggaca acatatttta tcagcagtga  98100
atacagcttc tgatattaca gcaggtaagc actgggcggc atccgtattc ttgaagccag  98160
acgggatcac taaagtgaaa ctcaaattga cttcaggaga tgagattaac gaagggactt  98220
atgatcttgt agctggaaca tttacaggtg cagatgcaaa cataatcaat atggggaatg  98280
gttggtatcg tgtaattcta cacaaagtga cagttgccaa acaagcatct ataacctatg  98340
agattatagc tttaaatgca agtggatcag acactttcgc aggagatggt acggcaggtc  98400
ttattgcttg ggttccgcaa cttgagatgg gcgatatgac aaatccagtt tgggcgggga  98460
caccatttgt ttgttcttat gcacgagaca gttccagtgc tgctaccttc actattccta  98520
agaacggaca cgctggggtg gacatttacc acactgacgg tactgtgcaa cgagaggtct  98580
tcactggtac agctacaact tggatgttga cgttcaccgc cgcaagtgcg gattggggat  98640
cgaagttcat tacaggtttg aaatattacg actaataaaa aagggaaccc gcaaaggttc  98700
ccttttcttt tataaaactc tttataaatc aataaaatca gaacggaata tcgtcgtcga  98760
agtccattgg aggttcttct tgattttgtt gaggagcagg ttcttgctta ggctcctgct  98820
tcggttcttc cttcttaggc tctttcttgg cttcttcttt cttaggttgt tctgccgcac  98880
cacgaatggc attagctacc ttgtcagaaa gtgccagaac ttcacgagca ttttcaatca  98940
aatcttctac cgaaatagtc ttaccggaat gatctttaca ggcattcaga acagcgtgac  99000
caacagaagc ccccagatca taatcactga tatctacgcc acgttcttta gccacttcag  99060
ctttcagagt cacagtagca gactgaacca cacctgcaat atcaaacgct tcacctttaa  99120
caccattacg aatcaattcc agtgcaccgt ttacagcatg accagtctca agacctacgg  99180
tatcacgttt tttgaaggat tgtttgtttc cagtattacc tgaaacgcca gtcccaccag  99240
atttattttc tttcttctgg acaccttcag tagaaagaac agtgatgcga gattttttag  99300
tattgtagta agttttgtcg cctttggtat caactttgtc gatatcaata ctaacttcaa  99360
```

```
caccttttttc gatagtgatc caagtatcac catctttaac ctgaagattt tcgtaacctt  99420
ctttcagttc aatatcaccc aggctaatcc acgtcccttt tgcatcctgc ttggcaccct  99480
tttctttcag aacgagtgaa gcacggtgag tagaaacaat cgacttacca tcccattgga  99540
aggttttagg ctctgcgaat ttatccagtt taacgtagtc tacaacacca gttgcataag  99600
ttacagtttt gcctttacga tcagtttcag tattaattac ggacattatt atctcctcta  99660
tattcacatt gtttttgcac agaactcacg aagaagctct gcgttttctt tttctaaaag  99720
gtacttacct ttacctattc caactccaat ttctccattc ggaaaatgaa caaattgcac  99780
agaatgcata tcgagtttta ttgtaacagc atttccggct gtgtcaataa cttttcggat  99840
gttatcctgt aagctaataa attctttaac cgttatttca gtttcggata ggtcagagtc  99900
ttcgacacga gagaataact ttcggtgtcc acccttacct atcaggattt gaaagaagaa  99960
cgagttatcc agacctatta catctttttc aacaagtatt aaactgttca ggtattcgct 100020
gtattcagtt tcaacactta ctttcgaacg ttcagtcatt gattgtcatc ctatcataaa 100080
agattagtga aagtcaagct ttattaccaa ggaatatcgt catcagtatc ttcgaacttt 100140
ggtagagcct tatcttgcgt gcgacgctgc acatccaagt cacgtacaaa acgcatatgc 100200
gggaagcgat ccgcgatctt acggacgtgt ttcgcatcca ctttaacatc cttatgcacg 100260
aagcaaatat ttgttgcatc tgttaccaag aagtcaggat cgaagtaata ttctacacca 100320
tcaaacgaag ctttgcaaac agaaagatca aagtttttca ggatgttgct catgtagcat 100380
ggttccatga tcataaggtt gcaaacctga tcatcacgga taaactcaaa cacatgtttc 100440
agtccgatca tagactcata gttgtcaccc atttcctgct gacctaacac ggttacattg 100500
gtgcctttaa gatcctcttt gataaacgta attatctgat ctatgtttcg gtgtggctgg 100560
aatgatgtat agaagtccaa atctcgccct gcaatatcca acatatacca gtcacgaact 100620
gcacctcccg ccagaataga acgaggatca gcaatcttaa gaacagtaag gatctcacgg 100680
gcaagcgtaa cctggcttga tttagtcatg ggtacgctcc acagtaactt tgacaatatc 100740
tctgacgttg atttcatctt ccaggatttc aacaatacct tcttcataga gacggcaaca 100800
ttcttcccag acttcggctt cagtcattcc acctttaact ttatcagcaa cacctgtaac 100860
aacaccagca tcctgatcat caatcagaat tgaaacatta aaactaacta atttacgcat 100920
ttcttctcct tatacttcca agtggaaagt ttctttagat acgaagtcgt atccgccttg 100980
tttcagccaa tcatcataca cctcatcagc atgattttca atcataaagt ggcgagtagt 101040
aacttcatct ccaacaatac gaacgatctt ataacagatc ataataccgg aagtcattat 101100
tcgtcctcct ctaagtctat ttcattctga caatgtggac agaacccatc attatgcatg 101160
tgttgttcat aagacatgtc tttaccacaa gaccaacaac ggatatcccc atcatcccac 101220
tcacgatcct ccgcctcatc tgcgaactca tcgggtaggt aaggcatacc aaagcaatct 101280
aaatcgtaac gcatataccc tcctgtaaag ggggccgaag ccccatacca tcagtgacag 101340
gatgcccagg aactaccaac atcgtatcca gcagtaagct gaacatttag tttgtaatat 101400
tccccagctt tgataacagc aagagaagca agttctccgg cacgactgta agctgtaaac 101460
caaccacctt taggtgattc gtgaacgtta gcccaaatct gccctgtctc tttctcttta 101520
ttatgcttcc actcgttagc ttttgcaaga cattctgcat ctattttctt ctgctctttc 101580
tcatcatcca ctttaaccca gcctaaagat tctttagaga accatttaaa ttctaccagg 101640
ttacgagata cttcaagctg cgcttcatcg tggtaagcaa tcatttgctg aacgaagtct 101700
ttattcttcc agtcatcaac gaagaagtca acagctaaac cttcttcttc gatcatatcg 101760
```

tcataaatca ccattgcacg tttagcacag ataaccccgc cactttggaa taacgagttt 101820
aagatcgcat gtgcagatcg tgttggaact ttacgtccat caataccgag aacatactgc 101880
ttgccagtgt taacccagaa ggcatttaac ttctctttca gttgtgctaa cgggaaagcc 101940
gcttcccaga atgcatcaaa taccagttgt cctgtgtact tatcactacc aattgtctta 102000
gcaaccttgt ctgcctgtgc tccatatgta atcccgtatt taacagcttt agctggacta 102060
cgttcaaact tacgtccaat agtttctgtg atacgtcttg ccatcatggt atgaacatcg 102120
ttaggcttct ccaacaagag agcgttacag tattcatgag gctccggttc gtagcgccaa 102180
caataatgcg attcaatctt tgcttccaag gagtcaaagt cataaccgat ctggaagtaa 102240
cgcggtgttt ctaccccaaa caagttacgc atttcgtacc caaacaacga tgtaacgcga 102300
ggaacgttcg caacagagcg atgcttcata cgagatgttg cagcgtcaca cgtagccgct 102360
ggagtcgcta tacgaccatc ggcacgaact gctgccaaga aacctttatc atattcttga 102420
tcttcctcat cgtcttccca atctgcaccg ccacccaaaa tagagtttcg acgatgtttg 102480
tacgtcaggt actgcacaat ctgtgttgca tacgggaact tctcgcccaa tgcttcgaga 102540
ttaggacaaa tctctttctc ctgccccttc gtgaagcacg ggttggtcag cactttaaga 102600
ccacgacctt tccctttagc gagacgttca cggattctaa gttccagtgt ttcagcatca 102660
gcttgtaggt gttcgcaacg atcattacag aagttgcttt ccagagtctg tttgacataa 102720
gacagaatac ctttctctaa gtcgtcagga tctttcttga tcttcgaacc agatttaagc 102780
gtcaaatctt tgtctttata ttcagacgga acccaaccta aacctacaag ccagttttta 102840
atgtgtgtcg tatcattcag tgtagatgga atggtaggtt cacaaatagg ctcttcactt 102900
gagatcggta acttaaactc tttatctaaa acaagcagcc accaatcacc ttcacgttct 102960
tcaaggctac caccatgttt ctctgcaaac ctaatgatat ggtttgttgg ctcaccgttc 103020
ttcttgatct gaagtttcgg tggaataaaa tctttcagat aaccccttagt cgctggctta 103080
ggtggaagaa taggttctac caacaagcgt agacgttcca tttctttgtc taagaattcc 103140
aggttctgtt cggcttgttg catgttgaac ttaaagccac ggtgttcttg acgggtgatg 103200
atatccgcaa tacgttgctc caagtcgaac ggctcttgcc acttcttata atctccccat 103260
tcttccatga ggtaatgata tactgctgta gttgctttgt tgtcgtaaat acagtagtac 103320
aacatatctg ctgcgaacgt cttgaatcgt tccccttctg gaatctcttt acggaaatcg 103380
atcttaacat ccccgccagc ttttttagag agagcattca agttgtgtcc aggtttacca 103440
tcaaccttgc gatcagggtt caatacttta ctaagaatca aggtgtcaat aatcttaact 103500
ttcgaatcac cccaagtatt gtatttaacg ctgtaattca gcccgtagta aagcttaact 103560
gccaagtggt catagttgat gccgttgtgg gctacagcca tttctacgag gtattcaggc 103620
ttatctgcaa acttgcctgt atggttgaca aaatctggaa aatctgccag agggaagtgc 103680
gtgtattctt gtgccacata ctccttcagt acataagtgt acttaccatc agactcttca 103740
taaggacgac catcgaaaat gtacttagga ccatcgtgaa aagcaatgat ctctcctgtt 103800
tcgtggtttt ccagacaaat acaatgcata ccaaaagtat ctttcaatcg ataagggctt 103860
gccaggtaat caattgtgtc attgttcagt aatgcggttg cttcaatatc ccatgtaaac 103920
ttactcatta gtcctccata ttatataact caacctgaag ggtatcacat tcctcaatca 103980
aaagtcaaga ggggcttgcg ccccttctga atcaatacgc gccttctgca ccacctgcat 104040
tatcagggtt agcaaaatac tgtgctttgt cgtgcagtgt ggcagtttta atatcgtaat 104100
agaattgtcc agcaggacca gtttccgaga actcacggtt tttcaagata taacaatgag 104160
ttgtgttgcg ctcaacaggg tcttctgcgg ctttatctcg ttccagtgcc agtgtaatac 104220
ctgcaccttt tgccaagaaa ctactaccca ttgcatcatc ttcagttaag tgctcattac 104280
cattgttcgc agctttctta acgtgggaga tcacgatgat cgtaatgccg tattctttca 104340
tgatgcgctt caaccacgtt gccaactctt cttgctcctg aacactcatc cccgacaaca 104400
gatccgagta tgggtcaatt accaggatgg taatgccaaa gtagatgatc atctccagca 104460
ctttctcctt gattgaatca atgtctgcac cacgatcatc acagacaaag aagcgaggag 104520
aaccatcttc acgaacgtag aagttattaa tagcttcctt gttctcttcc aggatcgcag 104580
ccttttcttc cttagtctta cgatgcaaag gaatatgcag gaaggaagaa agaaggttac 104640
gtgagtattt cttatacgtt gcctccaggg atagaatccc caacacatgt tctggatgag 104700
ccacgataat gtgtttagtg atttcattca ccatcaatgt cttaccgata ctcgttttag 104760
ccagaataac tgtgatctct tcttctacca gaccaccacc caacatgttc gcagcagtac 104820
gcatgaacgg agggagggtg atcacttgtg catccagaca gtccattgca gcttcataaa 104880
gttcgttcga agcataaaca cccgctgggg tataaagttt tgcaccccaa taagccttca 104940
caaagtcttt tgctttatcc tgcaccaagt attcattagc atctttcagt tccatcttca 105000
tcaggtaaac tttattacga ggcaacacct tcacaatgtt ctcaaaagct tctttacctg 105060
ccttgtcatt atccatgcag acgatgatct tcttgaactt ctcaaagaaa gggtactgtg 105120
cctgtacctg tttgtacata ctggtttcac cagtcgtacc actaactacg gctggtaatt 105180
catatttcct gtcaagacct tctgccaaca tttgatatgc tgccaaggca tcatgttcac 105240
caccagtaat gattacagtg tgggaacgct caaggaaacg aacttgtcca aacaaatcta 105300
catctttacc tacttgacca atgggcttgg agaagtcttt aggatggata cgacgcttaa 105360
aacctaccag ttctttaccg atagttgttg gatacaaagt atgttccaca acaataccgg 105420
attcttcttg tttgtactgg taacgaacac cgtagaattt agaatattct tccttgatcc 105480
cacggtagcc tcgtgggtta gtgcctgttt cttctacaat cttacgatga atctctttat 105540
taaattccga acccacaata tcctcctctt cttctaaaac ttcaccattc tctcgtaacc 105600
attcaacgct ggggattgtg tactcacacg cgaagcattt tgctccttta tgctcaccgt 105660
tagaatccaa cccgtatacc attaaattgt tacgtgagcg atccttgcca ttcttcatac 105720
agcgtggaca accagtatgt ccttccctgc taagatcaac atcaaatcca tatttcgtta 105780
taatgtgtgt cacaatcctc tcctgttaaa atgattcgtt agtttccatc atgtactcgg 105840
cttctaatgc ctccatatgt tttttgaatt ggtatgcaat ttctgtcacg gtcacgttaa 105900
tgtcttccgc atcaagctgt tccagacctg catagaaacg gataccatca atcagtaagc 105960
cgccgtgata atcccaatca ctttcccgtg aatgtggatc aggttcttcg tagtaataat 106020
caacttccac cacaacatta aaaccacttt tcgtagtgta ctcaaaatca aaagtattca 106080
gcattatagc tcctcaaata ataatctacg gcgttcattc agcacatcaa tgtgataatg 106140
cttacgaaca tatttagcta aagccaatcc cttctcgatc cccacatcag gttcttggat 106200
caggtaatta acaatatctt cccattcact tcttgattct gcaaagaaca gtaaatcctt 106260
aaactcttct gtgaagtaat tctcacgagg agaacagacc aaaggcagac ccttggcacc 106320
agcctccaga atcttaaggt tacttttggc gttattaaac atattatcgg ttaaaggtgc 106380
aagcattatt tgatgaccat cgtaagattc catatagttt tcatatggtc tgacagcctc 106440
ataattgcag cttggagcca ctttttcacg tatgtcagtc cattgctgac tacttaacac 106500
ttcactatcc ctacggaagc cgcagatggt taaatccctt ccaaaattcg gcagcagagc 106560
caaatcttgt ttgtgtgttt cacttccagc ccatacgatt ggtgatttgg agtagcgatc 106620
acgagttaac gtaaactgat cctcgtcaaa cggtaaacca tttgggataa tatgcacgtt 106680
aggattgtac tgggacaatt ccacctggag agcaggggtt gttgtcgtta caagatcact 106740
gcgttcgagg aaccattgca agtcttctcg aatacctgca tcaaaaatgt cttccagcat 106800
atggccttgg ggaatgttta aagagtcatc caaatccatt accatcttaa agcccatgct 106860
cttaagggct atgaagcctt gtttcccttt cgtagggaca ccgttaaaga catatacgtt 106920
ctgtgacggt tgggccgaga actgccttgt gtaaggcagc attactcggt gataatcaca 106980
gacactatat tcttttccac cacgattgtc aagaataatt tgtcccataa acacctacag 107040
actttcgatc acttgacgac gcaattcgtt tgcatccttc aagttgtagt gagtacgaac 107100
atgttcagcc aagaacagtc cacgatcttc acggtagttt ggattacgaa gtagttttac 107160
aacttcatag tgccactctg ccttgctatc tgcgaaggtt actgcacggg catcgatcgg 107220
gttgtagtaa ggtaatacct tagaacaaac gattggaata cctttagcac cagcttctaa 107280
tactttcagg ttgctcttgc aatggttgaa gtcattatct actaacggag ctacagccat 107340
agcatgacca tcgtatgcag acatataatg attcaaagaa tctacagcag gtttatactg 107400
cgcattaggc aaactacggc ggatcttaac ccactcttgc cctgtcactg tgctgctcgc 107460
ttcataccct gcgatagaca acaggctatc atcaaaagtg tttgaaagca aacgtaaatc 107520
cggttcatga ctcgcacctc cagcccaaat gataggcgta cccgaagtac gatcatttga 107580
gagagtgaac tgatcatcgt cgaacggtag agcatttcgg atcacaacaa cattagagtt 107640
taagtgacga attttatatg ccaggtattc tgttgtcacg ataaccacat ctgccaattt 107700
aaccatttcc acaatggtgc gggtgtttgg cgcgtacaga tgcgccaggt agtgttctgg 107760
attcaattga tagaaatcat ccagatctac aacaatctta acaccttggc gcttaagttt 107820
ggctacttca tcagcaccct tcgagaagat gcggttaaag accagtacat cagtacgtgg 107880
cttgatctct atgttagaaa atggcatgac aatgcgatgg taatcacaac cactgttgaa 107940
tttgttgtca caaagtaggg ttggtttctt atttaacgcc atatccttca gcctcttcaa 108000
aagagatgtg tgttttgcca ttattaatat cctccaaaga cagtttgtat tcttcccaat 108060
tgatcccgat tgccgattct ttctcttctt ttgtcagatt agcaaaaggt aaagggttat 108120
caccgaaaac atcgtcgggg tgaatgtacg ccataatgcg catcggacaa ggtacgccct 108180
ggagtccttt attcaaacct gaagctttca gacgattagt ccattctgca tcttcgaaac 108240
catatccgtg tgtataagga cggaaataac ccatcgtctc aacagttgca cgagaataca 108300
ttgcaaactg acacatagcc aattcccaga agactacttc tcccgaacaa ccgatcacag 108360
tatctttgaa gtattctggc ataccgaaga agtcccaacc attctcgaca gcctgtttaa 108420
cgaagtattc ttcccaacca cgtttaactg gatagcaatc atcgtcgaaa ataaaccagt 108480
agtcaaaacc ttcatcgtag aactgtttca tcaattggtt gcgagcataa gctacacctt 108540
tacgatcggg gtcgtgaaac actttgaagt ctacaccagg tgcaaccatg tagtctttaa 108600
gtggacgaac acctacagtg ataacgccaa ccccaatttt aatattttcc atctttcccc 108660
ctaaatagtt ttccggtgat catgacaatg cataaggtgt gatattgccc gttgaggatc 108720
tttttgacct aaacggtaaa tgtggaagag atacatccca cgcatcaatc ctaacctttt 108780
tcctcgttca tgtaaagtgt ttgagaagat tatatcgaac tggatgctac gttcttcaaa 108840
agggatctcc ttccataatg atttcctgaa caatagaaag aaacctgcta agggagtgcc 108900
ttgtggaact tcttcaatct catctccata gtaatcacga gcaactttgg catgagaaat 108960
atggttcaga atgttaggat catcatcaat ctttccaccg agaagttgat aactactacc 109020
taaacgatta caagacgcac cgatcacatc aaacggtgga ttggttgcta ccaaatcttc 109080
caacatagaa ggttggtctg gcagtaagaa catggtatct atatcacgta aacagaccca 109140
actatcttca tgaagaacgg caatagcatc attaattgct ttgccgatat ctccagtcag 109200
atagggggta atataataaa tcatactaac cccttactta gaatccacta ccattccgcg 109260
tttaaccatt gcttgacgaa tctcaagcac acgatcccgt gcttccatat attccttgaa 109320
ggagtcttgg agatgatcca aagccacatc ccgcatttta atcagtttgt cgtttgttac 109380
gttctcaaga gaaagttccc ctgtattatt tatcccattc gttttcatca acaacccccct 109440 taatctgaac agcacaagct ttacaaatgc aactaccgtt gccctttgac agttcgatat 109500
acggctcatt accgtcttcg ccctttcttg aatcgtagat tacactattg aaacaaacaa 109560
cgcaaacact tttcaatatt gtatatttct ctactttctt ccgagtacgg aagtttacct 109620
caatgatatc tgccattagt gaatcacccc caaaatgttg ttttgtgtca taaccattga 109680
agattcaata gcatcgtgac ttcttgcaaa acgctcccac agaacagcat ctactttaag 109740
agctatgcaa ggataaatac tgtcgttgat caactccacg gaatatttat caacatcgct 109800
ttcgtcttcc atgaagaggg tagcgtaagc ttccaaacct ttacgaatgt agtacacatc 109860
ttcttcggtt aaaccgataa cgagataact cgcaacaaca acagtattat cttctcgcat 109920
attagctcct tgtcggtgag tagaactgat gttctttata acgatacact aagaccatat 109980
cttttgtcca gtgtgcacgg gtttttactt tcttaaaaaa tgtcgcacct tttgtcatgt 110040
cctgggcttc tctaagtgta gggaagtttg tatccaggta tataagtcgt tttgcgatag 110100
ctttagcttc tttccatcgc tcggcttcgg taacgttaaa cttcttcctg taagaaaatt 110160
gtcctcgttg gaagagaata tctttaatat tatcagggaa gtaatcatcc cctttcctgt 110220
tcaatactac gttacctaca gcatacattc cacgtttacc ctgattacga ctttcagcgt 110280
aaattgcaca agctaagaga ttttctttag tatcttgctt tgcacatttg tgaactactt 110340
tagcagtctt tacgtttgca gcttcggcgg ttgccgtgac aggtgtaaat gtaaaagcag 110400
ttaaggatag taacgcaact gttacaaagt tttttatcag caaattttgc ctccttttgg 110460
gtgaatgaac taccagtata acacatgaga ggcgtttttg caatgggggga tttctccccc 110520 aacaacattt cagttaaatc ttacgggcaa tcataccatt ctttctgacc accgaaggcc 110580
ataaccacat cacagatatc catacctgct ttaccaacac cgtaagcttt cagtttccat 110640
tcgccgtctt cacgaaccag ggaagctacg tggcagatcg tgttaccagc tacttcagga 110700
gccaggaagt cgaagtccag gatctcaacg ttacgctcgg catcaaaaat cttcagcata 110760
ccttcgctgg catggcccag acgtttctga cccgtttcat catcaatagt caggacaaaa 110820
gcaatctctt cggctttatc ggagatctta gccaaggtta catcgatctg ttccatttga 110880
ccagtaccgt cacgaacatc atcccctgcg aatacagaac gttctggatc aaacttgtta 110940
gcataacaaa ccagatgacg tgcagacagc atttcagggt tgccagaagc gttgtgtcgg 111000
catacaagtg cgcttacatc cagatccagt ttagagtttg atttccagga gaactccaga 111060
cgcagttctt tcagtgccgg agcaactttc ttcagggaaa tcttgtcagt ggaacctttt 111120
ttcagggaaa ttttatcgct cattatatgt ctcctctatt atttaagttt aatttcgtta 111180
actgttaact ctacctgcac caactctgcc gtatggtgta ttgaacacaa cattgcattg 111240
taattcattt ctaccgcatt gtatgggtgc ttggtgtctt cgtctcgccg caataccata 111300
taaacgatga ctgcttctgg gtcaagaccg tcttcatcgt aggcgctttt cagaacaaac 111360
aaatcccgat gtgtaagatt tgcaatgcga caagtctgaa tctctggttt gctatctttc 111420
ttaatggcga aatttaacat cttgtcctcc tgtcgtgatt tctggtttgt tgatacgcat 111480
tataacagct ttatttgctt tgtcaatcca ttcttcataa aaaggatact gatggatctc 111540
aacacggagt ttaagttctt ccaaagaaag agtcccaaag taatctttaa gacccttcat 111600
gatgaaagct tctctctcgc gcatcacttg caacactgtt tgagagatca gcgtgtcgat 111660
catttcttag caccaacctt ttcaacccac tcaccgaact cttcagacaa gagtttatcg 111720
taaagctgct cgtctgtcaa ggaaagatcg ttcagaccaa tgaatgctac gttgtcgtaa 111780
gcttcagcca aatctttcag gaaagagaaa cgagcactac caacacccac catgaaccag 111840
tagataggtt taccccttgtt cttttccagt acggagagta cacggctcgg atcatcgttc 111900
tcaccatctg tctggaagaa cacaactgcc ggagtaacgt ctgcaccagg cacagcaacg 111960
gctacagttt tttctacaac agcttctaca gtttcagttt tacccagtag acggttgaag 112020
aaacctttct taggaacttc tttggttaca ggagtttcta cagtttcata tttagtggtg 112080
ctaccgaagt aggaatcgta aatatcctgc ataacaggtg catagcttgt gccaccctgg 112140
actgttacac gaccattaat gcatttacca acgtaatcat catacacatc agcagttgct 112200
ggagtgattt cacgagagct attgttgaaa gcccacatat cgatctgcgc gttatcatcg 112260
aacagcatac caaacggaag cagcttaccc acaaactcac ttacagtacc gttacgatac 112320
aggctggaca tgctaccgga gatatccagt gcgcttgcaa cgcgcagaac gatcttttga 112380
tcttcgttga caattttctt tttcttcagt gaaatggtca gggtgtcttg acgtttcttc 112440
aggctaattt tattggacat attatttctc ctctgtaagt gtaatatcgg taactactaa 112500
acgaactgca accatcggca catctgggga tacggtatgg acactccctc ttgatgaact 112560
attcaaacaa acagcagtcg cgccgccgct tttaagaaat actaagtttg caaacgtatc 112620
caaaccattt tcttcatatg ctgaataata catgaaagtt tcaccaatcc ccaactcttc 112680
gaaacgaact gctacatctt ggggttttga atcttttatt ttaaaatcaa acattccctc 112740
ctcctttacc agttttgaag cccaaatcgt aagcttcttt gatgattttt tgtaactcgc 112800
ttgtaggcag tgttacaaga ggatcatctt cttcaatttc cattttgtcg tcttctgttt 112860
cagtaaggac attatgcact ttatgataag ggttgtcaac acgtttgaaa atattatttt 112920
cggtgctgta gaaataatcc tcttcttctc cgtttcccca accttgatta ggatcatcct 112980
cggatcgttt tgtagggact tctcctgtaa agtgttctgc taaaaccata gcaataccgt 113040
ctccacggtt tacagagaac ataagatcac aaacgtcgct ccaaggtata gtccattcaa 113100
aactttctct gttcccgtga gtgtcctgtt tactggagaa gacacgccca taactatcat 113160
aattgccgta catctcttca atgaccttcc cgtctttcag cagaaagaga taacaaggag 113220
atccatcaaa agatgtggag agggcagctt tgcccgactc cttacacaga aaactaaagc 113280
aacccattaa acaccttcct taaggttgtc aatggcaaca gttgtttcac tggactcgtc 113340
atactcttta tggagacgaa ggaaatcttc tggcccactc caatcatgat cttgagtctt 113400
ccatccatca atgaaggcat cttccatgat tgtgatcagt tcctggcgag ttaactgaat 113460
aatatcgggg ttcttaacaa cctccacacg gaaacctggt tcttcgtatt ctcccaaggt 113520
gataatagat accaactcat cagattcaca gagataataa cctttaagga agcaagaacc 113580

```
atcttcgtct gtgataactt cataaacttc accgcttgta agattgatga aaagagtcgg 113640
atctgttact gttaatttca agtttacgtt tgtgtgttta aacatcttct tcctccccta 113700
aaatatggaa cccgtaatta caatagtcct gaaatgtttc ttttgcaaga tcttcgatat 113760
cttcttgaga catatcgtct tcaatttcga tatccacaac ctcattgcat ccacaccaag 113820
cagtttcaat attcactcgt aaagttttca ttcttcctcc tcgttaaatt ctacgtctga 113880
aagaatctca aaaccaaaac tattacaagc ttcataagaa taatctttcc gtaaacttgc 113940
taagatgttt ggaggctgta cgctgcacat aggtgcgaat cgacgttcgt catcatagcg 114000
tacaccaaaa taattttcaa ttacatagat acggattctc atttaccaag ccccttctta 114060
acagcatcaa ccatcccatc ttcgagagat tgaacttcgt tgatgtaatc aacacgggca 114120
gcacgggctt ccgtattgat gcggttagtt tcttccaaca tcttaactaa gttttcctga 114180
tcgtgacgca gggtttcaat atccaacact tggcggttag ccagtgctgc tgcttcgatc 114240
tggttctgtg tggcaagatc gctacccagt ttgattgcca ggttgaactc gtccagaacg 114300
ttgttctgtg tttctgctgc tttcttctgg cgcagacttt caatatacat cgagaagttt 114360
gccgagtaag caggaatcac attgttcaca atattacgag cagaacgcat gaggctggca 114420
gatactttct gcatacccaa tacacgcggc cccatttgca cgcacagcaa gcgtaatgcc 114480
ttcaagtcag caatacgtat ctccaaaaga tcaagcgtgt cacggacgcg ttgacgggct 114540
tctacgtcat cttccggtgt ggcttcaaaa gtagccagtt cttgctcata agctgctgtg 114600
agtaattcca tatcacgatt caggcttgcg gcgtattgtc cgatcgcctg gtgcagcttc 114660
tccaggtaca ccagagagtc ttcttcttta cggatatcca tttgaagatt cttaacgagt 114720
tcttcgatac ggttgttcac gttatcgaac tcaccgaaga gatcttcttt catccccatc 114780
agtttcttga tgagtttacc tacaccttta ctctgcttaa tggaggcagg atcaagctgt 114840
ttggcttgtt taatcaaggc ggtaaggcgt tgactcattt cgtcaccttg attgctacgt 114900
tggtgtttca gcacttcagc gttcagagaa cggagagtta aacctgcttc tgcacctact 114960
tcttcaattt ctttacgaga cattgttggc agcgtaggca cagcttttgg cgctgctgga 115020
gcatacaccg gacttgcatc caagacactc ggagcgaaca cagacttgct tgcgtctgta 115080
gtagcagtca gtacgctcgt ttcagatttc ttttgaccac cagttgccgc tttcaaaaat 115140
ggacttgtca ttcttcattc tcctcttcta tttctcttgt gtaaggtgaa acaccatatt 115200
ctttagctac tttaacccaa tcttcccatt tatacaacca tatttttcct tctgttcctt 115260
ctctatcact cttcaaccaa atatgcggtt gtttccctgg agtcatacgg ttaggtttac 115320
gattataccc tctaacacat cttgtggcaa atctatctac caaaacaaga acatatttgt 115380
actcatggtt taacggttct ttggaagtag ctttaggatt ggctcccaac tctgctgcca 115440
gcttttgcca gtgtggtcca tgacgactga acttacccat acaaccgtcg atcgcatgag 115500
caatctcatg cttcattgtg tccactatca tatcccttgt ggagttttta tgcaagtgcc 115560
aatttacaac aacaatcttt tctcggtagt tgcaccaacc gaaagagtta ttcactttgt 115620
tcctaacgca agccgtatat ccagcttcac gtagcatgtt gtagtaaaca gggaaatcct 115680
ccttgatctc ctgcatcact tcccaccaca agagttttaa atctctctcg gtattcatgc 115740
attacacctt gaagttaaag cttgttgtgg tagtttcgaa atctggtgcc gttaagtgtg 115800
cactgaaatc agagatttga ttaataatga aactcttatg tgcacctaaa acaacaacac 115860
ttttaatatc ttctacagac atttcccaca tattggaaaa acggataaaa gtttctcctt 115920
cttctgcaac tgtgaagaac ataaggtttc cgccagcagt gtaacccact tctttaaaac 115980
```

ctttgatcgt atattgctca ccgctggtaa agaaaactgt cgccttattt acagtgcgct 116040
tacgctctgg aacacctttg gcacgtttac ctttaacctt tttaactttt ttggctgcaa 116100
gaacttcttt cttcttttc tgttcagcta cggcgtacat tacgctcatg aaatctttag 116160
gagacaacag gagataatcc tgctctcctg tcaattcaga aacatcatag tttacagcat 116220
ccacataatc ggaaaaacca ttacttttct ctgctacaaa gtgagggaaa ttatcccctg 116280
cgaaaaggtt agatctcttt acatccacat acgtatcttc cataaaagca gagaatcctt 116340
caaacccagg agatttttta agattgtcaa tatttactgc aatcttatac tcgtctgcca 116400
acgggcggaa aggttgctga aagcagctac gcatctctgc atactgaaga actccgttag 116460
taataccttc gaaaacaatt tcattacatt cttctcttat ttctttcact cggaagacgt 116520
tcttgttaac ttctaatgct tctggggaat aacccgtacc agataagaaa tacagatctc 116580
caactacagg taatggctga atatttttca tattttctcc tcatcttaag ttattaagta 116640
gtgaccacca atcaaaatct tctcttgact tctggtgtgg agtttcttct ttctgcgtat 116700
taacacaggt gtgtttgaaa tctccagaga agcagtaaat ctgctccccg tctttgtata 116760
gggatacttt actaccattg atcacgtttg tcaacacaaa aagtatgacg aacaaaccta 116820
ttgcaaaaca aatattttca aacacaaccc aaacaacttt cattacagaa atacctcgtc 116880
atctgtctca ttatcccaga agaatagatc ccaagtgtca gagttatccc atttagcata 116940
aggagaggtc cagaaaccat ataccttaat ttctgtaata atatcatcga catttgcact 117000
tgctgcttgt agttcgtaac gcagaactgg ggtgactgta ccctcacctg aaccacaaca 117060
agcttcaaca ttaggtggaa gatccatagg aggtgtctgt ttaacttcta cataagcata 117120
aggaaaaacc tcttgaatcg cagcttctac ctcttggatt gtgccagaaa gacaccaaac 117180
atattcctga acatcatcaa aatatacaga cataattcct cctatgttag taagaaacct 117240
cccgaaggag gttcattggt attaagcggt agcttcttct ttttcaggga agatgaaact 117300
tgcaatcacg cccagtgtca gagtaccaag cacgatatac atgctgatcg tcgggtcaat 117360
atgcgctggc aggaagctca cttttgcgtg cagcgtttct gcaaacgggt gatacatcag 117420
tttcacacca acaaacacca ggaccgcgat aactgctttc tccaggtgga ccagatactt 117480
cagggccaca ctaagaacaa agaacagagc acgtaagcct aagattgcac agagcatcga 117540
agagaataca agcagtggtt cttgtgtcac tgcaattaca gccggaaccg agtctactgc 117600
aaagatcaca tctaccattt ccatcacgaa cacacaaacc agagccggag ttgctacacg 117660
aacaccattc ttaatcgtga agaacttctc accatccatc tgatccgata ctgggaacag 117720
tttacgaacg acgcgggtag cccaatgttt agagtaatca actgctgcgt catcgtcttg 117780
tttaaacaac atcttcgccg cacaaaaaag aatcacaata ccgaagaaaa tattaacata 117840
ccatccgata cttagcagat aagtccctgc cgctacaaac acacctcgga agacaatcgc 117900
acctgcaata ccccagagta gaattttgtg ttgtaagtgt gtgctcttaa tcccgaaact 117960
ggagaacact gctacaaaca ctaccaagtt atctaccgag agcgacttct ctaacacata 118020
cccgctcaag aacaagtttg caaaagctgc gccgtgctgg aagtatacaa aaccatagta 118080
ggctaaagac acaccaatcc agaatactga ccaagccaca gcggatttga atgagatctc 118140
cttgttctca cggtgcccga aaaaatccac cgcaatagac agtactaaga tgcctaccag 118200
aaccactaca tcaataatgg ggaaaccaag ttgcattatt ttctcctttc tctttgcggg 118260
gaaccactcc ccgcctcatg tgatacatct tactctattc taaaaccttg tcaacactta 118320

```
ttttgaagaa ctggaagaaa agattccacg tagcactgca ataatgaacg cgacacacac 118380
tacagtccag aatgtcactg gaacagtgat atctgtatga cccatagctt caacaacata 118440
gttgtaagcc agtaacaata accacgctgg gatcaggccc aacagaaaag caacagcaaa 118500
cacaataacc actgcaagaa aacctgctaa aacgcccata atatttctcc tcttaaagtt 118560
tataaatagt cacatcgtga cctgttttta ctaaagtttc ttcaattatc acttcgatga 118620
tagcccaatt acctccggcg tgacccgctc cgatcatagg taaaccaatc ttacattttt 118680
ggtcacggag aagcaagtcg ttagccatag ctattagtgc atcataaagt gcatcataat 118740
ccaactgacg acctttagta ttgtatccat aacgatactg cccgtataga ttatatacca 118800
agggatctga ttgttcgtcg ggtactccta aactaaaaga acctaactta ccctgatctc 118860
ctgactttgt acctaaatca gcagcatacg cataaggaaa tgctcgttta atttgcggag 118920
caatgccttt acccatgtta cacatacagt tacaacaatg agctataacg ttcacttccc 118980
cattcttggc tgcatcgatc agattgccag taacaacctt caacattttt cctccttaaa 119040
ggatatgttg gttaaagtag cgattgagga acacaaagtt ttcagagtac ttctcaatct 119100
tatcgtaacc ttcaccaaga cacccaaaga acagtgcttc gacgtaatga tgcggcagac 119160
gggagagaat gattttaaac tcttccggtg cttgtcccat caaatacttg ataggacgaa 119220
ccaggcactg tgcatcacgt tcttcgttaa tcatcttaac gaaagcatct gtcgtgttaa 119280
tgtaattgaa gttcagttta gcttctgtat ctgcttgatt accagtatac tttgcaaaat 119340
acaggaagta aacatcattc gtcaccttgt tttcatccag gatctcaatc agtttatctt 119400
catgagttcc cgtgatgttc acatcgtcaa tgaaaatcag cttcttgttg ccccagaaat 119460
ccttgttgca atagaaggta tctccatcaa tcaacttctt acgactggct ttatccagga 119520
aaccataatc gttaatgtaa ctcaccttgc gatgaatggt atccaactct actgcacggc 119580
tacccttgtg attcaacagc aacaggttca agaagttgat gaactgattg gtcatcatcg 119640
ttgctgcgtt atgcacatga ttgtaaggtg aagggatcac cacaaactct tcttccggca 119700
tattcttgac taccaagtca tagaaagaga ctgctaatgt tttccccata cggcgtgccg 119760
cctggttgct accaaacttc agtttggaat aatcacgaat atcaaagcga gcagtttcca 119820
gattatcaaa tttgtgagca aagatttgag tttgattacg cattaacaag ttctccttta 119880
gcaagtttat ctaacaagtc gttagggttc ttaatatgac agaagttaaa tcctatgtca 119940
acacattttc catcatattc ttcactatca cctacgtgca acacttcctg ccctaccaaa 120000
gggattggag aataagtgat cgtgcgagca aagaatcgcg gatctggttt acaaagtaaa 120060
gcttcatccg agaaatgtgt gaactcaaaa caattccaac tttcaaactt acaggcacgt 120120
cgcaagatat ctcctgatat gaagttggta ttgctcttaa tgctcaaatc ataacgcccc 120180
gaaagataca gcaagtgcat cggtagatcc acagctacat gaggtggaaa cttaaggaac 120240
cattgttcac actcgaaacg aagctttgca gacttcaaag gtgttatccc aagttcgtaa 120300
ccaagtcttt cccaggcgta tgctgcacac tcggctgttc cctgaagtgc ggcattgtcc 120360
agttcctttt tgatcttttt gtaagctgct cttgcttcta cttccgtaat atccccgtat 120420
tttgcgatag tccacgctcg catatctgcg taattggggt ttgctgtgat cagtgtgttc 120480
catacatcaa aagaaatgtg tttgattgtc atattaagcc caccatgcgt ctaagttaag 120540
attactgtct actaccactt gttctacatg gtagcccttt atttcaacat tatgtgccag 120600
aagcatatca taagctttct tgaactgcaa cttatcttct tcggtataca gacgggcatt 120660
atagaaacga taatccacct cttctgcatt agaagagata cggaagaagc cagtgtcaat 120720
```

ctccggcata gaagccggag tcttgatgtg tacctctccg tagtgctctt tgcttaggtt 120780
catctgcatt acatgttcta catccttgaa catttgttcc agtttatagc gtaatacttt 120840
gaaaccagca gcttttaact ttgccacaca ttccaacatt agtcctgtgt caatgccacc 120900
ctgatactta gttaacatac gatcgcgttg tgattgtgtg tcacgatgta gatcgatagt 120960
tgtgcatttt gcaccgataa tcttcgctgc tcgcataagc tcttcactac ttacctcggc 121020
taaggtcaga tgaaagtgtg ctttccaaac tttgtctact ggtacaccaa aaacttcatt 121080
accagcgcga ggcatattaa cgatcagttg ttgcattgtt agtctccttt agaagggcag 121140
tcgttgaagt tcgtcaccgc cgatatccag tagattagca atatcccgat cagaaagcaa 121200
ctcttttctt tgcaaaatat caatcagggt acaaataacc tcacgagtgt ctcgatcact 121260
atccataatc agcttcccag ccgtccctac ttcgtttttc actgcaaaat acgtaaccat 121320
attatctcct gtattaatct gcttgccaaa taccattctt cttgctccat aatctctgat 121380
tatcagaacc tctgaatggt tttctgttg gttgatttaa atcatattta ccatccatga 121440
ttgtatccac aacatccttg atgtgggaag gaatgtcttc aaacaaatat cctgtataaa 121500
ccatcacatc cttatcttcc ccgtacactt ccttaattcg gagtatcaac ctataaacct 121560
catcaatatt ctgtgggtct aaaggttctc cccctaagat tgttacacct ttaatgaaag 121620
gtcgtgccag atctgctaac acacgttcta catctgcttc tgtgaaagct gtgccataag 121680
agtatgacca ggctttctga ttgaaacatc ctctgcatcc gtggctacat ccactaaccc 121740
ataaagagca tctcacccct tctccgttaa gcatgtctgt tgcttcatag cctgaacaat 121800
tcaaagatgt ttctcccttt gtaacacttc ctgcattttc cctttgttgt aagggcgcga 121860
gttaggggcg gatagatacc cagaaacacg acgaataacg gagatagttt cttcttcatt 121920
attcccgcac gaagggcatt caaaaccttt tgctgtagct ttaaactccc catgaaagtt 121980
gcatttgaaa cattgatcca ctggttgatt gatgccaaag taatggatgc gctcataagc 122040
ataatcgacc aaagcttcta aagcttccaa gttgttcttc aggttgggag tctctacata 122100
actaatattc ccgccattac tgatttgagc aaaacctgtt tcgtagtccc acttctcaaa 122160
aggatttgta acctcccaaa caggttgatg gaacgagttg gtcaggtagt cccgtacatg 122220
cagattagga taatttttat ttaaagctgt ggcaaacttg tagcacaacg attccgcagg 122280
agtgccatac aaactgaaag gcagattaga caattcttta aactctgtac aagtgtcttt 122340
catgtattgc agaatagctt tgcccatctc tttcttattt gcttcttcag agtataagat 122400
ctccaaagct tcggataatc ctacataccc aatactgatt gaagcatacc caccctcaaa 122460
caaaacgcca atctcatcgt cagcattgag acgtgctaaa gccccttcca taaacaggat 122520
agggttttct gatgcgcgtg tacggcgaag gcgttccacc cgaagcatat gagcatcgta 122580
agccagacgc atatgttcgt caagtagatc agagaaacaa tatccttctg tttttgcttt 122640
agctgcaatc aatggtaagt ttattgacac aactcctaaa ttaaaacgtc catcgtactt 122700
ctctccttgt tctgtagcgt aataagacag gaacgaacgg caccccatac tggtaacatt 122760
tcctttcgta gagcctgtca cttccttgtt aagaggtaca gaaatgaagt caggatagat 122820
tcgatctgca caacactcta aagcttgttt tttcagatcg taattaggat ctccagttgc 122880
catgttaaca ccttcctcca ggaagaacac aactttaggg aacacaggtg tgacatgatc 122940
tttccctaac ccttcactgt gtaccttaag atagttctta gtgatcatcc tcccaaaaac 123000
tgttgtgtct aatcccatac tgatagtgat gaaaggagat tgtccattga cgctcatcag 123060
tgtattcacc tggtacaaca atgtctgcat agcatcatat acagccttat ctgttgctgc 123120
taaagcttcg ttacagtctg ggtatccgta acgtagctct gtttctctta aattcttaag 123180
gtatgtagct tcaacatact gacttaaccc ttggtcgata tgagcacaag tttgtccccc 123240
gtactggctt gaagcaacag cttgaatgat ttgcgtcaat actgtggtgg ctacaccaat 123300
ggacttaggt ttctcaatat acgcagcacc gattttaaag ccattctcca acatgtcttg 123360
atagtttacc agacaacaat tcgtaagagg ggacaataga taatcaagat cgtggatatg 123420
cccaaaacct tctgtatgcc attctgcgag gttttttggt aatatctgag tcattgccat 123480
gtgcttactt aaaatccccg ccagtaagtc cctatgtgtg ttaacgaggt gggagggttt 123540
gtttgcgttc tctcgtgtat atgtgtcaca agttttatcc aaaaaagaaa atacgtcctg 123600
atataaatta tgcatatgtg ttccttattt aatagattga gattctattc taccatttat 123660
ccatagaaag actttgttca ggatcaaaaa aggcgcactt agcgccttct tatttattat 123720
ttagaaagga actgtcgtcc catcagctta ccacctttaa cggcagtacc atcatgacct 123780
tggtaatccc aagaaccgtc aatgttagct aagaagttat cacggtgtcc attctcttca 123840
atcaccaccg cgagaagcag gttgctgtcg atctcggaaa caacagactc aacaatacct 123900
tctgcaatat tacgcgcata ttggatatac actttctcgc ctgtaacctg cacactgtcc 123960
acattcttaa acatgtaggt ttgttgtgtg gtgtagagaa tacgtacaat tggcttctta 124020
cctacaggag gtttttggcg agttttgcga taacgtggct tcggtgcata taccggagca 124080
accacctcat cttgaacaac ctccatttta gctacacggg gaacaatcag gtatttcacc 124140
agatcccaat catgaggatg gttctcatct actctccaac ccatatcatc ggctgggcct 124200
gtgaaagttt gcccgttacg gcagacgatc ttcacgtaag gattaccctc tggagggaag 124260
ccagggttcg gaaggtattc ttccacatat tcttcaactt caaaagtatt ctcttccact 124320
tcttctcctt cttttgttaa ttcagcaatg atatcttcca atgatttctc ggtattgtca 124380
atacctaaat gcttcaaaaa cagtttgata aattcgtcaa cacctatttc taatccttgt 124440
ggactgttgt gaccatcaat ccccgactta gaactataga aagagtagtg ttcagacaga 124500
ccacgactgt acatcagaaa atgttcagca tctttccaat acccttcacc agtcaccagg 124560
gtgaaaatct ttaaaagaga ttccatttga cttgtggaaa tctttctggt agatacgcac 124620
acttcgtgaa tagatcgccc tgccacttta gctaaaataa gatctaacat ttcttctcca 124680
tctatgattt ctggttttgt ccctaagcgt ggaatatttt cataggagat agaatccacc 124740
cctaaaactt cagagaaaat aacaacgtca cgcccaccat gcccttcttc ccaagctttt 124800
tggagttgat cggcagtcca accattacca taaagcgcgg ctacagccgt atataaacgg 124860
gagttcccat catacagacg acttgctgcc atacgcagcg tatccttcat acagtagtag 124920
ataggcttcg aatcacacca ggctgtctcc aaaagcagat caatgaaatg ttcggtagtg 124980
gtaacagaag taacacctgc tggcagataa tcctcggagt gtgtagcatc aataccatta 125040
gatggatcaa agaacaaaaa ccctgtctct gcgcctacat cattacgaaa atcttcttcg 125100
ttgtcccacg gaccttgctg aatctgctcg caaagatcat agatcttggt aaactctgca 125160
tctgtcaggt cttctgtgtg gacataatat ttaaccaatt cttccatcga cttattcata 125220
aataaacccc tctctgtggt taagagcaat agatgctcgt ggttctgcta tgcctgtagc 125280
atacatgtac ggatgacctt tcggagaatt cctcattccg aatgacccta attctaaccc 125340
atatttgtct tccacgtcaa accctatttc agtttttact atacgtgttt ccagactata 125400
ataggtccaa agaaaattac acatatcctt tgcatatgct ataggtccat gtttcggata 125460
aaactcaatc aattccagtt tcagaaagat gttaaaatga ctttcatcaa gaacatcttc 125520
tgtgcggtaa catggggtca atgccatata agggtgttct gctacaaact caaaaccatc 125580
tttctccatc tggaggaagg attgttctgc gctggcaaca tagaatctcc cattaggatg 125640
ccccaaaggg caatcctctt taccttctgg tagtgtgtat gcaagaatat ctgcatctac 125700
caggtaaggt acttgaatca tttgtgcata gcgtccgtaa tagtggatcg cattggcaat 125760
gacttcccca ttcatgatct tcctcctgtg cggaaagcac gtttggtaag gtctgacata 125820
gtgatcaaat cttgcaacgt catcccagga aactgtgtct ccagcacacc ttcaacagca 125880
cccacaatat cagacaattc aaccaattgc ataagtctgc aatcctgttc gacagcatca 125940
aaaagttcat aaacttcttc ctgaatcttt tcaatactgc cgtaaggttg tttctcaatg 126000
tctattaaat gataacccgc catattaata ctcctcacat cgaatctgct tgatcttacg 126060
agccaatgct gcaaccatct catcttcttc agtcatttta ggagatgtgt ctccccctaa 126120
ttgctgcatg gttaagatct catgcactgt ctcattccac tgcaaacatt taatacaacg 126180
tgtgtgagca acatacagaa ggttacgttc agattcttcc agtcctaccc actcgcgtgt 126240
cttcttatca tagttcgaag ggaagtcatt tgcaacgata acttggtccc attccaaacc 126300
tttcgatttg tgtgctgtgg tcagcgtcac ctttgctgta ggtgagttac ggtgcatacg 126360
gagtgtgtac gcaatgttgt tagctttacc tgaaacaaca atattcagta gacgtttagc 126420
gtctggatct gattctgcac aatccacaaa ctcctgccag tctgcatacg ggagaacagt 126480
ctcatgcttc actttatcaa tatctccgcg acgcaatgca ttcacactgt ccaccatagc 126540
aataaaatct ttggtgtcaa cgttaatatt gatatcttct ccgttcgcaa tacgatccat 126600
tgcatccata agcaacgtca ggtttttacg gaagatgatt gtgtacggtt tggagaagtc 126660
cactatatcc gagtggaagc tacctgtcac cgtgttatac cctttcccta ccaatggatg 126720
ggccagggga gttttatcac taaggatcgc attagcaata tctgccactt taggaccaaa 126780
acggaaacat gctgtcaatg gtaattctac accatattga gccgtctctt tcatcatgtt 126840
ctgactacct cggaactgat aaatactctg gaactcatca cctacaacca caatacgact 126900
ggccttttct gcgttacgca ggatagacag gaacgcaggg ttaacatcct ggaactcatc 126960
accaaagatg atatcataac ctaaatcttc gcccgatagt tcgaaaagtt tcacataggt 127020
gtcatgagtc atgatcgttt cagagttagg atcaatacgc tcacgccaca gttgttttgc 127080
atatttaacg acttctgcga tcagcttatt ctcattcaca ttcttacgtt tcaggtcaga 127140
aatgtgcatt ttagggaagt gtttcaaaga gatatgctca tcatctgaaa actcgtattt 127200
agccaaagtt tgtttaacca ttaaaccgat catagcacga gtgaccaaag tctttccgtt 127260
tttatcgata aggttttgaa tcttaaactt cttggcgatc tcactacctg ttcccgccac 127320
attcacatac ttcccttcag gacgtgagag tttgtgacgt aaattttgcg gaagcttctg 127380
atagcagatt gagtgcagag ttcgacactc tacattactc ggcatcttac gacgcgcttc 127440
ttctgccatg cttttgttga acgccaggta caggatgctc ttgtctgtgc catttgccag 127500
catgtatagg gtagatgttt tccccgaacc agattttgct tgaatagtta caaaacggtt 127560
ttccccgaaa gcacgctcaa tagcaaattg ctcttcggtt ggagtgaaac tcaaattatt 127620
agacactaaa tcctccttag taaaaactct tgacaatatt cattaaatga aaggcccgac 127680
tcgcatacgg ctctctcaag tttggtggga gatgggaacg tatataacgt tcctgtttct 127740
cccatgacca ttttgttttg acttttggta ttgtatcacc tgcattgtta ttttcaactc 127800

-continued

```
ttatttgcac tgtccagttg gaagggaagt gttcaccacc tttcttgaac ggtatgtagt 127860
gccctaaagt aaactctttc ttgttcttta gtctcccagc aagattaagg ttgacaatca 127920
tgttacggaa tacaaaatat tgataaagat tgtcaagagt atatacagcg tagtatgccc 127980
taaacgcgct atccctgctc atacctttga tatccatacg gcaccagttt aggtttgtag 128040
gatcataatc atgagcatca atccactcct ccctttcttc aaactctgcg ttaaccgcag 128100
attgtccagc agtggcaacg aataaggaat ctacgtcaaa gaacatacta cctcctgtta 128160
tttcacatcg tgcagtgcat tacctacttt caggacgatc acatcattaa tagcaccttc 128220
tccgttcaga tcgctgaaca caggggtgac aaaggtaatg atataatatg catcaacttg 128280
aatcacggca atcttcccat caagctttac atctcgtctg aatttgaagc catatagctt 128340
ctctgttaaa gggagatcac cctctttcaa caaagccaaa tcaaagatac gatacttttc 128400
tgacccgaca taaatgtagg taagcttgtc ttcttcatag tggtacagca tagcttgctt 128460
gtcttgcaag acgcttgcac caaatacatc caccgcaata atgttcttca tagattctcc 128520
tcccagttcc aatacccatc cacaaacggt ggattacgtc tatcgtattc ccttcgcgcc 128580
catgccacgg ctgcaacgag cacatctccg tgacatttct ggggcgagca aaagcagacc 128640
acatcttttc cttccaactc caacaaatct tcaagactta tcttaccaga acgaatctga 128700
tcccacaacc attctttata acgttgaatt gtagatcctc tcggctcatc atcttttaat 128760
ttgaaggggt tggcaaactt agacgctttc aacccgaagt ggggcatagc gcgtccaatg 128820
taaactgctc catctggaat aactttacct aaatggtaga agttcaagac tttcatatta 128880
ccccaaacac atacgtgcga tcaagctttg cgttaacttt tctgccgctt tataatcgta 128940
atcgacttcc tctaccccac cgtcttcatc acggaagact ttcccttcca ggaatccggc 129000
atcaatcagt ccaatataca gatcatactg ccaacaggag ttaccaaaag gtcgtttacc 129060
gctgaagcta tcctcttctt cccataacgt ggaaagaagt tggcggaaga actcacgcac 129120
agagacttta cctaaatctt gatgttcgaa catcacatct aaagcgtctg catcaccttt 129180
atctacaaac gggacgtaat gttcaccatc aatagtgact tgcaatacca tctttctcac 129240
ttttcctcct ttttgtattc aatgaacata tctgcatagt aagctttacg ttcttcaaat 129300
ttagcagggt ttatcacaat gaacaacact tttcggttat cttgtggttc tttgaccgta 129360
atgtagattt ctttggtgca ataaaaacct gttgctttat aagcgtcgcc ccaattatct 129420
actccacgat ctatacgatc aaacttacag ttatactttt tatcatccac ctggtagaca 129480
gcttcaccac cgtaccaagt gaagaattgg ctaccttcca ccccaatctt gaaaccgtca 129540
cgggcggctg tagcattggt ggcaatcatc aacatcagga cacaaagtag ctttttcatt 129600
tagaattcct cttcagtctt ctgtcggttt ttgaagaata ctacatcata tacatctccg 129660
taaccatcat ttacagagaa catgataaaa cgatcatctt ctgctgttgg tgcgcgatgt 129720
tcaagttcaa aactttcaat aaaaccgcgc gaatttacgt agtagatttc gtcctcacca 129780
gagaacatcc agtccctgtc tatcagatag aaagataaac tcacaggcga caactcatcc 129840
ttcacagaat cattgtacag catgtgggct gcaactgcca aacttaaagt cgtattgtac 129900
tgcattacac ctcctcgtca gactcatctg ctttagagaa tacaacatta aacgtttcac 129960
cgcaaccatt atttacgaaa tacatgataa agttttcatc ttcatctaca gggccacggt 130020
attccagttc gtagctatac agagaactat tgcttgtggc tccctgcgga taccagaaat 130080
agatctcatc gaaagattta acccacttca aacctgtacg atcctcaaac actaatgagg 130140
aaggattgtc agcatctttg acagcttctt cataatcctg gtgaaacttg actgctgttg 130200
```

ataatgtgct cattatgcct cctcgtaatg tttgcaaaca acgtgtctcc acgtcttctt 130260
gtaatgttct cgcttcgtca tagcttcttg ataagaggga atacgctgta acagaagtct 130320
ccattcgcag tctacgccca tacgtccgta caaagcataa cgaacattat ttttcttgtc 130380
ttgcatactc cctccgatca gttaattaaa ctttttccca agtgccaaat gcacattcag 130440
ggtaaatccc cacctgcatg ttaccattgt catctttgaa tgtaaagctg ttgttctctt 130500
tattcaaagt ggtggagtag gttttaccga tcgtcacaca acctgcactg tgtcccagtt 130560
gagtcagtga cagacatttc attttttgtt tcttcgtagc catttaaatc tccttttgtt 130620
tagtgagatt gcattctatc agaatacaac ctcgtgatca agacttattt gcagattaag 130680
attattctcg gattgggcta acagtcagat gcgctttcaa gattttccac acacgatctt 130740
gagagaaggt atcttgcgga gaagtgatcc ctgtatcaaa cataactgct aaaccgccat 130800
ctactttctg ccagatagga ggctcaccag aagcgtcagc accgccatag acaaagaaag 130860
tgccttctgg aatatcccgc aggaagtaaa gcttaggcgg cttctctgtg taagagatgg 130920
tattcaatgt tcctaatgta tttgccaggt tgctatctga cccactctct tggtagtcac 130980
ggattgcttg caagttgata atagagtgga accaatcttc agcagtttcc aggctacgtg 131040
gtgcagggta gtaatccagg aagttgctat caccccaacc gtaagttgta actgggccat 131100
gattacgtgg ataggcagaa tacaggttta aggtgccatc ctggttctgt gtcatgtatt 131160
gagcatcgtc acgaagcaca ctaagatcca taaccatcgc atagtctaac aatttcattc 131220
tttatctcct aagtttaaac agtttaagaa gtcacgaagg ataatcattt gttctgtaga 131280
caatgagagt acaccttcac cataaatatc accagcccat tcagcagtaa gatctaatac 131340
gccagtccca gggaaccaat ccacagtgat cctattacca ttcgagtcgg gcagtatacc 131400
attaattaac ataacacctc ctctatatta tgttcttgat cttacgatca tctaacgata 131460
agaacaagat ctaagtttct gttcttcaaa caatctaacg atagaaacta taattactac 131520
cctctaccct aacgggaggg taacacttat acctcgctcc cgctcggcac ttcgtgggta 131580
gggtagcata tctgaaaaca aaagtcaaca gttatttttt ggttaacaga taaatcagtt 131640
gttcacttgc ttctggtgca tagagtgcct tagtgtcaga gtcaaagaag tgagtgactc 131700
ctgtagcctt agatactgtg atagatagac gtgcaagctg gatcagttta tccatttcag 131760
caatctttgc acggaatact gtacgtgtag cgtcaaaagc tgcatgtggc atgtacttgc 131820
gatttagagc actgcgtttg aatctacgga agtctgcaat aatccggtta cgttctttat 131880
tcaagtgttg taccagtgca gtgtatacat gtggttcttt gttagccatt gttaatctcc 131940
tcttcataag ttggtagttc atgatatgcg atcacaggtg ccaagtcaaa ataaaaatga 132000
ccattgataa cagctaccgt gccattgcgt gttttgttaa cttcacagaa tcccttcttg 132060
ccgtttgcca tgattacaaa ccactctccg ataggaacat cctcggtgcc agatacttta 132120
atccatccac tcattttact tccccttgt aatcagacac tacaccaggt cttactttttg 132180 ccttaagatg tttcaactct gccataggag ttgccacttg tatagggtta acttcaacct 132240
cgttgatagt atactcataa cccgcatact tcccgatgga gtgcaggtat ttgatagcat 132300
gttcaggtga atctgcttca acatacccca aatcttttgt agtgcggcct tcacagtcgc 132360
cttctgtagt tacgtgataa agtgtcataa aacctccttc ttgttggctg cttcaatcat 132420
agcgttaaga gtctccatac cgctttcaac tgcttgagca atctcttgga acacagactt 132480
cttaaagatg tataaagacc ctgcctgtaa gcgttgcaca caacataaga tcgcttggtg 132540

```
atccatcagg aagtcgccgt aggctgaatc aatcttacct gtaattgggt tctctcgtga 132600
acgaggatca tactctaaag taatgtgtgt cacgcctggc aaggtaacaa actggcagcg 132660
aatattaaca cgcggtgcga ttgacacgct aaacagattg ttggacattt aaacctcctc 132720
gtagtaaggc agagccttga tcaattgttc tgaaatctca ttctgcaccc atgtagtccc 132780
gttgtcaagc gaaacataac ctttttttatc gacaaactta cgtagacaac cagtgaactt 132840
gtttttgtag atcatttctt ctttcctttc ttcagtttgt tatgaccttt acctttgtaa 132900
agcttgtgat tacgagcaga cggtttattt tggttatcga tacgggatac cggagtttgc 132960
cacattgtat ctccagtggc gaaagatgcc gccacaagaa gttccaagtg atggtagtcc 133020
agttcaggca tctttgtttc acgcatttcg cgttctacat tagacaatag ctcttcttcc 133080
tcaatcacag accaaccctc ttcttgccaa gcctcctctc tgaaccaagt ttccatgtta 133140
taaccgtgtt cgtcgagaat aacaccatcc cgcatctcaa accattcacc accacaaaaa 133200
tggcggtgct caacacgtct accttccttc attgcttctt tagcttcggt ccaagtcagt 133260
ttgatgtttt gcatttgttt tctcctctca tttggtatga gctaatcata acagaacaaa 133320
aaagcttgtc aatacttgat ctgaaatatt tttagtgtac aatagcccta cattattaag 133380
agaggtgaac aatgaacatt acattagcaa ctaagaacat ttcacaaact atcaacggtt 133440
ttggtgttat cgtggctttg cacgggaata atgagaagtg gttagcatct ttcgaagaag 133500
atgaaaagca caatgttatc ctgaacgctc ctatcaaggt gatgcacatc gttggtgaga 133560
gtaaggtact tacttcttct cgttcagagg aacaaattac aaatgaatta gtaaaactgc 133620
ttgacaacgt tcttcggatg tttgataatg cacccatcga cacaaaacgt gtcttaatgt 133680
gagaggagaa atacaatggc ttaccctgac tacatcgacg aacgtgctac tggcttcttc 133740
cgtaacttct tggttggtcg ttctcacggg gatggtggtt ccagttataa aacaagctgg 133800
gatagtcaat gtggcgctaa ggccaccaaa actttgaaaa tgccaggtcg tccattgtgc 133860
gcgtattgcg gaaatgaagc cttatccctt cagcctggta ttgagcatgg ggattatgat 133920
attaaaggtt acacttgtgt ctgcaaaggc gcaatggacg aggcggattg ggtgaaagaa 133980
aaggcagaga tggaggaacg tcacagacga gaagtttatg aaatggaaaa acgtatgcct 134040
gttccagatc ttcaagttaa gaaagatatt gttgcaaaaa tgatggaaaa agttcagaaa 134100
gcagagactg aacaagaact aaaccgtgcg atcgagaact tacgtaattt taaagaagaa 134160
aaagagttgc gcgagattat gtggtaaggt atactacttc catcaactaa gagaggagaa 134220
caaaatgtac tattcacaag acgaagtggc aaacatcaaa ttaacagttg gcgatcttat 134280
tgtatcccct aactatcact gggataacac ggacatggtt gaagtagtaa cccatgtcgg 134340
ggttgaaggc gttgttctct acactctggg tggaggtgtt gttggggaaa tggaacgtta 134400
tacgacaacg aagaaactgg tgagttctta tcgtatgttc ttacacaaag gttcggaaga 134460
gtatgcagcc ttcttattga aattggacgc agaacgagga gaaacaaaat gaaacttatc 134520
catgatgaat tacagtttga cgtagaagat ctgcaagatt tggacgatac gttctccgcg 134580
attatctgtg ctggattgta tgcgttcaag gcacgtattg tggaacgagg ggatatcctt 134640
atcccatcta agatttgggc taaatatgta tcagattacc gtaaactaac agaagagcag 134700
gagcgggaag ctacagtgga gtggttatcc attattgatc aaatgatcga aggttttaaa 134760
cctgaatcag ttatgaccaa aacagataaa atggaaggtc gttgcctgtt tgctgaatac 134820
tttcataact tgtggagcta actatgtctg aattttttac agtggttttc ttagggattt 134880
atctggttat taatgctgtt ggcttaatca tgtctctaat agagaatatg ggaattaagt 134940
```

gggcttgtac attcggtata gctcttatgc ttagtcctgt ttggatttac atctgcaagg 135000
cagttcaact aattagttaa ggaggaaata tgtttagtaa agaaatgaga gatgtgatcg 135060
ctactctggt agttgatcac ggtattgagg ttgagcgcca ggtttggaaa gatgaggcac 135120
ctttctttga cttagcatca cgagcgaaaa gtcacatgca tctcctggaa gacggtaatg 135180
agtttgttct ccgtatgcgt tatgatcgag aatttcgaat tcctcttgac actgaaccgg 135240
atggtgtagt attgtggttg gcagaacatt tcgcatacga tgcactacac ggacggggtt 135300
tcggtagtga acgttgggat gctgtttgtc gtaaacacca tattgaacca gactacggga 135360
gtatgtaatg ttaagcgtta agcctaagat gatcagtgaa gaccagaaag atttcattta 135420
caaatgtgga cgaatctgga gagagtatac caagggtaac gaggtcgtgg tggttactga 135480
acaccagatt gaaatctctg atcttttcgg tgattatttg caagtgatca aattaggcat 135540
tgacagaggt ttggttgaag tgctaacctt atctcaagtt gaggcacacc acttagataa 135600
aactattgtg gaattgtagg aggtaatatg ttagatctta ttatcaaagc aagtttgaca 135660
ggttgtttgc taagtgcgtt gtctgcacct atcataggcg aatttcattc tcaattaggg 135720
atgtttatcg ctttaagcgt ggctactctg ttcttggttg tagctgcatt atgtatgttg 135780
ttggaataag aggagatcac catgaaaaag attattttag ccgtagccct gctgtctgca 135840
agtttcgtag catctgctgc accgtttgtg gctgcacaat ccacaagtac cggagaagtt 135900
gcagtcaccg ctaaaggtca gttcgcttat actgatcctg atggcaagtt cttttcttgt 135960
acggatgtaa ccccgtctgt ggatgtggac aattctaatc gcccatacgt ggctatcggc 136020
gctgtgtgtg gcaacaactt catcatcatg aagcagtata aggatgatcg cggtggtagc 136080
ctcctgatcc gtcaagatgt tgaacgtaag aagaaagctg tggtgatgga agctatcatc 136140
actaaaggtg aagggatcta aaataagtat tgacaagacg tattagacaa gagataatac 136200
gtctattcca acagaagagg agaaagtaaa tgaaatacac agtttatggg gatgttgcaa 136260
ttgttaataa agacttcggt gtagaggttg ataaactccc cgctggcgtt tggactgtca 136320
attgtgatcc acatggtaac tattctctta gtcgtgctga taagttcacg attcctgatc 136380
gcctgtacgg ggaaaccaaa gaacgtgcag cccacgttat ccgtaccttc gctcgtcgta 136440
gtaaagaagg taaaaacaca ggtgttctgt tgtcgggtac aaaaggcagt ggcaagacaa 136500
tgctggcaaa actgatcagt aacactctgt tggaagcaga agacctggga atcccaacta 136560
ttctggtaac gcagccatac tctgatgcca acttcctgga gttcatgagt aagatctctg 136620
aacgcgcagt agtactgttc gatgagttcg acaaagtgta ttccaagaag gaagatcagg 136680
aagcactgct gactctgctg gatggcacag gtagcggtaa caaactgttc atgctgacaa 136740
agaacagcgg atacatctcg gaatacttcg tcaaccgtcc gagccgtatc ttctatagct 136800
tcaactacga caaactgtct attgaaacta tgctggacta cctggacaag aatctgaaga 136860
atcgcaaaca tgttgaaagc ttccaacgtt tgtgggatgt tagcactgaa ctgtctttcg 136920
atgttattca agggatcgta gaagagttaa acttctatcc gaaaatgacg ttcaagacct 136980
gtctggagat gatgggtatc tctctgggta acgatgcacg ctggacgatt agctctattg 137040
ttgtcaacgg taaagctatc aagcctaact gggtcaacaa ctggcatgag ttcactccta 137100
ccaagttctt gtctggcgca tgtgaactga acatctacct ggaagcggtg aaagacgaag 137160
aactggagcc tctcgaagat agcagttacg tcatcctgga tgatgatggt gatccacgca 137220
tcgacctgaa agctactgcc gaaggtctga agtgtgacct gattgaaggt ggtaagattg 137280

-continued

```
tagtagtgag cgataaacct ggagatacgt tccgtgtggt tctggaacca accactacac 137340
gatctgcaac actgagcagt gtgttctgat aaagatgccc cgcaaggggc atttctcaca 137400
tatggaggaa attatgttag ttgatgttca aatcatgcgt aacgaaaaaa tggatttctt 137460
tgaagcagta gagaaacatc tgattcgatg ggactatgaa tttgttcctg ctggatgtgg 137520
accagtagag catttagcgg aagacgatga tgtatacatg atcattcgtc aagtgtacca 137580
gacagaccag tgtgaagaaa ctcctgaact gattctgttt gaatgtgcag accttgcaaa 137640
atactttgat tacgttgttg ctaacagcga cgagttggct tatactgaat ccagatacag 137700
taaacgtcta cttatcttag attacatgaa agagaacaaa cacaaactca tcgacgcaga 137760
cgcggtttat ggctactggt ggatggacta acaaaggaga aattatggca cgtttagcag 137820
atcatgaaat ctttaaacct attctgaacc actatgatga aattaaagca gtgttggatt 137880
gttatagaga ggatgaagaa cgtttggaag tcaatcttaa gatagttctg atgaaagctt 137940
ttcaagacgg gcaagctgaa gtcttaagag gtatgaaaaa tgcgaataac tgatgaatat 138000
gtattcttct tttcacataa agatgtgttt agcaattggt acattgcgcc atttacagag 138060
acggaaccag ggtacagtga cactttctgc tgtgtagagc aatacatgat gtggcgtaag 138120
gctttgctgt tcaaggatca ggtaatcgca gcagctatcc tttatcactc aatgaagcgt 138180
gacgacgaga aggcacaggc atactacaag cgcatgggtc gagcggtgtc tggttttaat 138240
aatgatgtgt gggaagagca ccgagagcgt atcgtaatgc gaggcttatg cttgaagtat 138300
acacagaacc ctgatcttta ctctgatttg cgactctacc aattcaaaac gttcgttgag 138360
gcgagtcctt atgataaggt ttacggaatt ggaatgggta tgtatgaacc aggggtgcta 138420
aaccctgcca actggaaagg gcagaatctt ttaggacaat accacaacaa tctgattaaa 138480
atcttgttcc cagccaaaat accataaagg cgatattcgt gatattttga aaaaattcgt 138540
ttttaaaaag aatacgtcaa ctttgtgcca cagaaataag gctcctacaa caccgtagag 138600
agccttttct ctttagctac accaacactc atcttttaga gtttacctcg ttagacgagc 138660
attcaggtag gttgtaggct gcgtagcatc ttcaggaaag attatctcaa atcttacaag 138720
caaactatct caaaaatccc tacaattatt taaacttttt atgagtttac aaaagtgaga 138780
atccaaaacc aaattctaaa gtttacgtac attatctcaa atgggtagac cagatcgcaa 138840
agcaaaaaac cgagaaaaat tttttaaaaa gtcgcgcgca ccaggtattt aaagtttttt 138900
tgcttttaca aaagtgaaag ttgaaaagca aattctaaag tttgcgtgaa aattaccgaa 138960
atgagaatta ttctcactta aaatcgaaat acgaatgaga atgagaatga ttctcattca 139020
actactaaat gcgaatgagt cttatttgca aatgagaatt tttctcattt ccagaatgac 139080
gggcaggtcc ggtgattgtc tcgcgctccc gtgtcccctc gccatgtaat aagaataaca 139140
gatccaacca ggaaagcaag cgattatttt tatctttaca tttctttaca aatatatagc 139200
gcccagcctc ccggcgatcg accttccaac cagtgcccct ggtatgttag ccccgccttt 139260
acgccgtggg gtggcgcttc ctcttctgta tgtaaaacag tataagcccg atccctgggc 139320
ttgtcaagat tattttttat cttcttgcca ggataggaca cctaaccaaa aatacatatc 139380
ccccgcgccc ctggcggtat attgctttcc ccgccgccac tgcaagccca taaataacca 139440
tcagcgaacg aatcaaaatg atctatctct tccactttat gatcgcccag ggtgagaact 139500
gtttcaacct ttaagcccgt tgcgcttgct acttggtgga ccgtgccgcc ttgccagccc 139560
aacgagtgca taaggtgtaa tgtagtagtt gtcatggtgt cgcccttctt tgttgtgcgc 139620
cctggttggc gcggtagaaa gatgatagcc ctttccttta tacgtagcaa gcaaaaagaa 139680
```

```
aataaaaaag attgaaaagt ggttgacgtt ccgcacctgg tagcgtagta ttcatcttgt 139740
cgaggggggc gaggcacaac gacaataaat aaaaggaggg cgcaatgcag gacgggcaaa 139800
ggtgaggatc tccataatcc accgtcaacc aacaaaaaac atcattcatc acctggagtt 139860
aagatcatgg caacattgca catagtagca aaagcaggac aaatcagcgt agtggtaaac 139920
ggtactaatg aaatgagtgt acccgatgac gaatatatca cggtgctttc ctttcttgat 139980
tcactggtag aaatgggcgt tataacagaa gatcagcacg ctattgctaa tcgccgtgtc 140040
ttacatatcg tagggcttga ataaaaagta ttgacaacag gcaacaacct gataagatgt 140100
atcacgtaga gcggcggaat ggtccaccgc tcacaactaa gagagattat catcatggca 140160
tcatatagcg caacaatgat cgtaactggc accactggta aacctatgag cggtggcgga 140220
tctttcgcta atatcaatat tgacgggcgt ttatccctgg acgcagcgat cgccattgca 140280
cgggaaacat ttaagaaaga atgtaatttc aacaaacaag attatctcgg cttcgctatt 140340
gaaaaaaccg cgcgttttgt caattataaa agcccgaaaa tggttgatac tacattaaca 140400
gcaagacaag taaacttttt gctgtaaggg ggctaacgtg cattttctta aggtatgcgg 140460
gaagatcata gcctttcgta acgaggaatt ttataacctt gctcgttatg ttatgatcta 140520
ccctggcaag gtatataaaa acagtccgac aagttacact atttacaatg tgctatcagg 140580
taaaaccacg gagatcataa aagcaggggt gagagattat cgcacatctt tctacccttg 140640
ccgtgattcc gccagtttat tttttgtgtg tgaaatgatt gttaaaaggg gtgtataatg 140700
gggcgcgaat atgtgatcca gtcctgggta aaacatgacg ctaatgatcc gcgtattata 140760
ccggatgaca tgatcgatca tgctcctggc tatagtggcg agcaaatagg taacagatcg 140820
gcgcgtagtc atgggaatac caaaacacgc agcgatcgcc ctggttggct ggcgaatggt 140880
aacgctgaca ttgcaagcgc cgcagatgat agcgacggcg cgaaagataa tccgctgtac 140940
aaggtagatc cggcttttcg tgtcctggat gaatacccca gcaagatagc ggcgcttgat 141000
gccgcgctcg aaagtaagcg catcacctgg acggcgtaca gtactgcaaa aagcgtatta 141060
gatggtaagc tgatccaggc tgaaaggaaa ttggccaaaa ttgcagccat agcccaggag 141120
gaagaccaag aagaggaaga cgatcacgcg gttgagtgcc tcgcctttga tcacttcctc 141180
ccagtttttg aggcatcgca ggaagagaag aaagaagccg aaaaaaatta tctttatttt 141240
gatgatttag gttgacaggt aaaacgtgat cacttatagt taactcatcg ggcggcaacg 141300
gtgccgctca caactgaaag gatagaaaaa tgtttactac ttccctattt tttgcaatca 141360
attttattcc tggtttccgt gctgcacttg aaatcattct ttggacactg taaggaaaac 141420
atgatgatca agaaagaaaa tagtttgaca gttggaacgc ttaacgctat tatcttggtt 141480
gttccatttt ggatcaccgt ggcagttatc acaacaatca ttttcaagta aggggcacac 141540
tatgagtaag gttatccgtc acgaaaaact aagccctaca ttatctatta gtgaatgcaa 141600
tgatggttat tggctatacg atgaaacgcg cggcatgaat ttagctatgc aagcgaaaac 141660
cgaacaaacg gcatatgtgc aagccctgga atactaccag cgacgactac aggaagtcga 141720
aaacgactat aaaagcctga aatcaaaggt tgatcacttt atcagccagg tagcagatga 141780
cgacgatgat cactactgcg aacgatgcgg atcatatagt taaaaatatc tttgacaacg 141840
tttaaaatta gtgtaagatg tatcacatag ggcggcggaa tggtccaccg ctcaaaacag 141900
aagagagatt atcatgaaac acttatcatc tatcaccaac cataatgaaa ttttcgttaa 141960
tgaaaaaggt ttcgcctgga ttcagttaaa agagatgaaa aataaccgtc gtgtaacggt 142020
```

tgttcgtaaa atcaagagta aacctttag caatttttca gtggacaccg tgcggatcaa 142080
gaatgaagaa tacttgatcg atagtcaaat cacttggagc ttaacggcat cagccgccgc 142140
gccatatttc gcaaactaag aaaaaaacgt ttgacactgt tttaaattct gatatagttt 142200
atcacgtagg gcggcaatgg tgccgccaac aataaaaggt taacatcatg gctatcattg 142260
caaaaactga gattataggt ttagattcga tcctcctggc ttatgaggaa actttaaaaa 142320
tgtatgtagt gacctatggt gattatgtgc gtgaatacga atacattgat cttgctttcg 142380
aatgttacat tcgccaggtc aataaagcct ataacgatta tcgttaaaag ttttagtctt 142440
atactattga caatgagtga tagtataagc ataataactt ttatcgggaa tacttcccac 142500
taaccaaaaa gagagagtaa catcatggct attaatatta atgtttccgc ttatgctacc 142560
ctggctaata ctgctaaaat tgaactatcc agcattgagg ctgtgcacat tagcgcccgt 142620
cgctggtttc aacagtccta cggcaataca tatttttctt taagtgtaga cgttgagatc 142680
tgcggtaaat tgattgaagt ggttaacgtg ccgtttcaat atggttatgg tgatcatttc 142740
gataccgtcg ccctggaaga atttagtaag gttatcaacc tggaaggcaa ggaattttca 142800
cgcggcgcgt atctttcccg cttttgccgt gacaatggga tcactgtata cagtcatgca 142860
agcgatgtta aacgtaaaaa agatttataa aaagcattga cagcacgagt aaaaagagta 142920
aactgtatta catagggcgc gggaatagtt cccgccccac tgaaaaaaga gattaacatc 142980
atggcaaaat caaaaatgtt cttaggtcac gctaacaaaa ctcattggaa tgtaagcctt 143040
tggattaata acgatgaatc attgtatcgg ttggccctgg attttattgc cgctaatact 143100
aatcgtaatg atgcggcccg tcatatgatg ctatttttag aacaaactgg acaagataaa 143160
actccagacg gtttcaagta tagcactacc gcgatccgcg ccgctatggt tggaatgtaa 143220
aggagacata aaaatgaaac atcgttcgac ctatctcaca aaacgtttta gcttagatca 143280
taaattgggc tattacggaa gaaatagaaa ataatttgac aaagttttaa attagtgtaa 143340
gatgtatcac ataggggcga caagcgcccc gcctaacaga agagagaaaa atcatggcta 143400
tcaatattgt tcgcgtatcc ggcaccgttg gcacttccca ggttattgca gttgtaacaa 143460
gcaaaaagat taatgatgta tgtgagatct tgaataagtg ggctattgct aattttggag 143520
aatatgcgag cgttgagtac atcgaagctt atcaggtgcc aaccatcagc ctgaccgatc 143580
tcaacgttga tcgcctgtta tgcctggatg aattaatctg aaaaagattg ttgacaccgg 143640
aaagaaaaag agtaaactgt attacgtagg gcggcaatgg tgccgctcac aacaaagaga 143700
gattatcccg atggctaata tccgcacact gttaaaaaac gcaagtcaag ttttattttc 143760
cgatcacgat catttcaata aagacgttac aggcgtaaaa aatatcaaag atgtaaaaag 143820
tgttatgggt atctattgca atatgaaacg tgttggaacg ttcggcgata aagtattata 143880
tcaggcgggg gattacaatt ttactttgac aattatttca taaaaccgct tgcaatcttg 143940
ataaaataaa gtaaactgta ttacatcaag gcggcggaat ggtccaccgc ctaacaaaga 144000
gaagaggaaa acatcatgat tacttttact acccgtgaag ccgctcgcaa cgttgcccgt 144060
aaagttaacg ccgctaatct gggcgcaagt gtcaaggcac ctgtaaaaga tgaatccggc 144120
gcttggatct tccctggtct gcgtcacgct gataatctgg gcaccttaag ccgtaaaaaa 144180
taatttgact tttcgttata acgccctata atgggcgtta tagagaagag aaaccaatta 144240
ccacaaagag agaaagaaaa tggcaatccg taaaattaaa gttatttgca ttgaatcaac 144300
tggtggcgct tttgtagttg gtcagaaata taatgcggtt ttaatgggca tggattggaa 144360
ggttaaaggt ctggatggtt acgaatacgg cactactcac ggattgcgtg gtcgaatcgg 144420
atacgtgagc ttcgacaaca aagaaaaatt tgttttcgat attgttgtga gtaaatagca 144480
tgaattgcta aagactaatc tgcgaattgc cgtattatca actaatcgaa atgaaacaca 144540
taaagagaaa aacattatga tcactttcgc tattgtcgcc gttgtcgctg gtcaagttta 144600
cgtaaacgat acattcacca cagaagacaa agcagcggga gacattaccg ccgcttataa 144660
cgagtgcaag gaagtaggaa ggatgttagc gccttgcttg cttatgagtg aacgccagga 144720
cgggatcacg gtgtttacta accttgaaac agggtatcaa atgatagtag aaaaatgatt 144780
gacaagtttt aaaaatccgg taagatgtaa caagtagggc ggcaatggtg ccgccaacaa 144840
cagaagagag acaccatgaa agcacaaaat gcaattaagc tttatattct ggcctcaatc 144900
gattatagtg agtatggcat cacagaagat aaagagaaga tcgcggaatt gatgcgccgc 144960
tttaagtctg agtactggta tcccgataat caaaaacgtt acgatcataa cattatcaga 145020
gcaatagcat catggttaca aggtttaccg tcagatatta atatcgcttt cgagtattgg 145080
gaagtagatc ggttgttaac atcctggggg tacattaacg agcgtagtag cgaaaacaag 145140
atccagaaag aaagggaaaa ctattggtta tatattgcag gtgtgatcct tacactttcc 145200
cacgaataaa aagtttttaa aagtagttga caggcatcaa gcaataaagt aaatttaaac 145260
acgtagggcg gcaatggtgc cgctcacaac taaaaagagg aaacatcatg aatacatcta 145320
atcgcgccga aaaaatccaa tcttccaaaa cacgcgtagc gtggaatgag gaagtgatcc 145380
gcaagggcga caagcgcaac aaaactaagc gcgaccgcac cgagaaacgt gcgtggatgg 145440
acctggaaga ctaaaacaaa tcaagggcgc aaatagcgcc ctttcttata tctaacgaga 145500
ggataacagc acatgacctt aaacgagatt aaaacagcct acaacgcagc gaacaaagtg 145560
gcagcacgtt accgcgacga atacggtttt attgcgcaag gcgtgatcct gggcgtttct 145620
aacgatggtt tgatttacat tgatgcttat cataaccaag ttaaaccgga aaacgttatc 145680
agtataaaat atctttaaaa gtggttgaca ccataaccgg acctgttaaa ctgtattaca 145740
tcaggcgggg aatagttccc caccatacaa aaaggtaaat attatgatca ccgcaaaaca 145800
agaaaaaatc attatcgacg ttgcagccgt tgccgctatt gctattattg gatcttatta 145860
tgatacccgt ttcccatcgg ctatgcatga gatcgccgcc gtggttagtg tcgctgtact 145920
gttttacgcg ggtaaacgtt atttgtcacc aattgcaaat aaacttgctt tttggaagaa 145980
ataaggtaaa gtgtattacg tagggcggca atggtgccgc gcccgtttga ggatcaaatc 146040
atggttaaag ctaacacggt gctactgttt tccctggtta atgatgccgc ttacttgtcc 146100
aacatgacgc aagatgatag cacattaacg gcaacgttta ccgatggact taaccgagtg 146160
atcatcgttt cactgaaaac agggagtaaa ggcttttact cgttggctta tcattgggta 146220
acagaaagcg acgagacaag ccaggactat agcgccccat tccctgaatc aatggcgcgg 146280
gagatcatcg ccgccgttgt aaatgatggt ctgtttactg cataaaaata atttagaaaa 146340
aggcttgcaa tcattttggg atagtgtata tttaagtcat agggcggcgg gaatagttct 146400
caaagcaagc gagaggataa cacaatgaac aaatacacag tagaatacac ggtacaaaat 146460
ccggcagtat ccgaagggcg taagactacg atcgccgttg gtgttatcgc tttcgttatc 146520
actatcttat caatcatctt ataaggtgca caccatgaaa acagtaaacg ttatcaggtc 146580
atcaaacatc attaaagaga tcgcccttgc cactggcatt gagatcgagg aagtaatcgc 146640
gctcaatctt acagaaaacg atctgcgcaa ctatgaagcg gaaagcgtga aagcaagcgg 146700
cgcggtcctg gcatataatc cggctaacaa gtaaggggct aacatgaatc cgaaagatat 146760

-continued gcaagcatgg aaagggtacg acgatctaag tgccttgcgc aataagtcaa gccgtaacct 146820
tagacggttg gaagcaaaga aaaagaaaaa tattaagggg gtgcaccatg cataacaata 146880
tcattgcaga tcgtgccgct actattcgcc caggagatcg ggcgcgttta caggttggcg 146940
tttatccgtt cccgttttat gatttctgta aggtaacggc tatcgaaaac aatccgtttg 147000
atcctgacac cgtgatcatc tggtacgaag gaaggggaaa cagatatgag gatatcatag 147060
ggcgtgatga atccgtaaac atcctacgct actaatcgcc agctaacagc ctaaaaggtg 147120
taaggcaatg caatccccta cctgatttaa ttagtgcgcc ctggcttatg ctggggcgtt 147180
ttacgttgta gaaaataatt ttaaaaaata tgcttgacgc ctggaacgtt ggcgagtata 147240
gtttatctca tagggcggcg gaacggtcca ccgcaaaaca gaagagaaaa catcatgact 147300
acttacaaga aaacgaaaga actggtaaaa ggcgacctgg ttaaaaacat ccttaacggg 147360
aagtattatc cggtagtatc agttgaacgt tggaatagcg ggtacatcgt taaacttgat 147420
agccgtgacg atgggtgtga gttttacgct gaatacagcg atcgccacac cgtgcaataa 147480
aaatagttga cagatatccc gaaagggatt atctttatca gacaggggcg ataaacgccc 147540
cataacaaga aaggtaacaa catgaaaaag attgattctt cccgcgtatt gtgtgaaatc 147600
gatgttatca tcggtaacgg caccggacac cataaactga tcaagggtaa ggcttatcgc 147660
ctggcaacgc tcaaagcaga tatgcgccta acagcaagtc agatcaaaaa gtttttttcgc 147720 ccgttgttga caacagcaaa gtaagcgcgt agtattcatc ttgtagggcg gggcaataag 147780
gcaacgccca ttaatgaggg tagcatcatg ttagagaaaa ttttcacggt agtaatcatt 147840
ggtctgactt tatcggttgg agtggttgca actatggcta acatgatcct atcttcccac 147900
ggtattggat aaggtgaatc aaatgatcac gaataagaca ggtaaaacag aatttttacg 147960
cggcttgcag atcggcaagc ctgagatctg gcattgcagc aagtccgcac ataacgaaat 148020
gaaagacttt accgctacgt tacaacgtgt taaaatatct attacacaga aaaaagtctt 148080
gttagtagta gaaaacgaga tcccgcaaac tattattatt gtcgagcgta cagcatgaaa 148140
acagaaatca ttattgaaat catcaacggt tataaagaag cctttatttt tgctgaatca 148200
gccagggatc acgaaggtaa ttttattgat aacttagacg attatgattt ttcagatcaa 148260
gcccatcagc ggatcattca tgacgtagcg gcgttttgtg atgccaatga tgccgctatc 148320
ttggaagcga tgagcgacgg cgcaacagcc aaccagatcg ggaatgattt acattttacc 148380
cgtaatggtc acggcgtagg cttttgggat cgccctgaaa tatacaccac taacacagcc 148440
aaccgcttaa ccaatgcagc taagtttatg ccgaacgtgt cggcttacat tggtgaagat 148500
aatttgattt atattgaata aaaagtattg acacagatcg ccagtgtgat aatatttacc 148560
acgtagggcg gcaatggtgc cgctcaccga aaaaggtaaa catcatgaaa actatcagct 148620
acctggaatc gaataacatg ttttttgctc ccgttgatga aatcatcgaa gccttaaaca 148680
acgaagaggg gatcaatggt ttatcttaca ctgaactttt acaaatggtt gcagcaaatg 148740
aagagcttgc ttactatgtt gaaaattttg atgaagctgt aatctttaca aaataatcct 148800
tgatctaatc tcttagataa cttatattta atgcgtaggg cggcaatggt gccgccgata 148860
atgaggaaat taaaatggaa actatcgcta ttgttaccgt agaaaaactg gttgttgggg 148920
atgtattcgc gttaatggtg cctaacagca gcaaactggg cgcttatgaa gtgatggatc 148980
ataaaaatga atcatttggc gatggttgca caatggcggt aaaatcctta aaggatggaa 149040
tcactcgcca ggctaactgg cacaaaggga atcaagtcgg tttaatatcc gctaatttct 149100
tgccagaaaa gcaaacatta gaccaactat caggcggtaa gacgttagcc gaactactgg 149160

```
aaacagccat ctaatcaaca aaggggcggc aacgccccac atcagaaagg aaaagattat 149220
gagtattgca acagtattaa acgccgttaa aaccgctgaa tcatccggct tacatgttga 149280
gcttatagat caaccaggtg gcgatctcct tgtccaggtt tacccgccga aagtagggga 149340
tgattattat tggtgctatt ctgatacgtt cgaacaagta gacacgaaag cgatcacagc 149400
ttttatttta aaagccgttg aagaaaataa ctttcatcat aacatcaatc aataaaccat 149460
aagcggggcg gcaacgcccc cattaaacgc aataggaaga ggatagacac atgaaaaaga 149520
tgatcgcagt agttgccctg gttgttggta ttaacgcgcc tgtaatggcg aaagagctgg 149580
caaaacacgt tgacctaacg gatatccatg ccgtcaatcg gatcggggtt acttatcgtt 149640
tatgccttgc cgctaaaact tttaaggacg gcacaacaga gtattacgga ttcgagggta 149700
tccgctgcgg tgagcttgca cgcgacctta aggaagatcc agaccttgaa accatgcaga 149760
tgaccgtaaa cggtaaagct tacgtaaacc gccaacaatg agaaaggtaa tcatgacaat 149820
ggggatcata gtagcaacgc tggcgctaat ccccttcctg attagatatg tgatagtaga 149880
tctggtttta gttgttagtg acctgctatc ttccatcggc acactgtttt aagggtacat 149940
catgaacgtg gaacaagtta gaaaggtatt agcagcgtta cgctatcaca accatagcaa 150000
ggtgaagaat gatcctgatt atgttgattc aagcctggaa gaagacacct tgcaagctat 150060
aagccatatg caagaattgc ttaaacgtat gacagagaag aacagatctg attatatagg 150120
tgacgagatc taatctttac aaaacagggc ttgtttttgt cctgtttttt gttatgctta 150180
ttgaacgggc ggcactggca acgggggagg taatcaccgg acgaccccgc tatatattga 150240
tagctaacac ctatcaaaca acaaaacatc aaagagataa actatcgaat ctttgcaatt 150300
ctacctattg acaccggatc acccttatat tattatttat cacgtagggc gggaatgttt 150360
cccgtctaat ataggaataa catcatgacc gaacaaatta aaagcactaa accgaacgtt 150420
aacggcaatg tttcacactt tatcggtgat aatgagagag gtacacccta cgccgccgta 150480
accgttcaac ctgacggtaa ttattggttt accgtttacg gatcttattc ctttggacgt 150540
ccggcacatg ataagatctt gcaagcggtt aagcctaccg gaaagaatat cacggcagaa 150600
aaattttata aaaaataact tgctttatag ctcctgttaa cttatagtta ttgcgtaggg 150660
cgagcaatac agcaagccca caaagaggaa aagaagatga gcaaatcagc aattaaagca 150720
gttgaaaaag cgcaagaagt gatcgcaacg tccaccactg gcgcaaaggt taatctcgtt 150780
ggttatctga cagatgaaac tatccgtaaa aattggcgca acgctgatct actggcttgc 150840
ttattgatta atagcgtcgc taatgctttc cagtgtgaaa cagccgaaag cctggaggaa 150900
aacttgttcg acaatatgga tcaagccatt gaaacctata ttcaatcaaa cttggatagc 150960
tggaacgcta agacatggcc cgacagttta cgcgatacaa ctgatcaact gatccgcctt 151020
gccctgatgg ttgaacgcga taacgtttac aacagcacaa agtaagattg tacaaggggc 151080
gcactaagcg ccctttaacg taaagaaatg taaataatgc gctatcacct attgacaggg 151140
gatcggcgtt atattatatt taactcactg gcagcaaaca acgaaacgaa acaaaggaca 151200
acaacatgaa cattaaatca aataatccgg cttactcctt cgataacgct ttttgccacg 151260
gtagcgccgc gaaaggcttc gaaattgatg gtaagctggt tattgtgaac gttgacgggg 151320
aagaggttgc agtatatccg gtaaacgatg ttaaaagccg tttacaatgc cgcatggatg 151380
ttaccgcgta tcagcttgat ccgatccgtg tagttgccct ggtcctggaa gaagagatca 151440
aagcaatgca tcatagtaac aagtttattg gtgacgcgca ggacaatatg aaagtatgcc 151500
```

-continued

```
gcagtaaagt taatgaagcc ttgaaagaat gcggttttaa ggatctgatg attaaacgtg 151560

atgaaaaatt ccgctttcgt aatgacctgg cgaaccggat ctactcaata tatgaagcgt 151620

tataattgac aacaaaacaa gggcgcacaa agcgcccttt ctttttgccc gaacaatgtt 151680

gatagcttcc gcctatgaaa aaccgacaca gaacaaaact gaatagatcg cggtatcgag 151740

ctaatcaacc attaaacgaa taaccataca ccccagggca acaggctgtt agagagctat 151800

ttagagcggt taaaatcgat caacaaccaa caacaaacga ctgaaaaaga ctgttttctt 151860

cctttccagt gcaatgataa ccattatcat ctacccttgc gtatctatgc aatataagtg 151920

cataactata atgttgataa tagttcgcaa caactaacca accaacaacc taaaacaata 151980

agcaaactaa tcataatcaa aggaataata gaaagatgat tgataacgac aaacaatcaa 152040

accatgatga atactaagca agataacgat aacacgacaa aacaaccaac taactaacga 152100

taacaaatga aaccattaaa ataataacta ttgccgaaat agtgaagact gtaataattg 152160

caaaatgaat cattccaagc ctcatcatta gcacgctacg ccggacacgt agcgagctaa 152220

taataagcca actacacccc cacaatcata actatcggtg atagttattt cttgtgatta 152280

tgtagcttgc aattattgca agcgtattac gcttacacta attacgctgg cttattatta 152340

gcattgtatg taagaatagt taagcgtaat ataatactca atgttattgt tgcatgatgt 152400

aatcattagc agggttaagg attatgcggg gggcaaggcg agcgaatagc gataccttgc 152460

acactgtaca gatatacaga aaataatctt ttgcggggga gacatgacac gaccgaaggg 152520

cggggatgtt g                                                      152531
```

COMPOSITIONS AND METHODS FOR INHIBITING THE PROLIFERATION OF PATHOGENIC *ESCHERICHIA COLI*

BACKGROUND OF THE INVENTION

Field of the Invention

The present invention relates to compositions and methods for inhibiting the proliferation of pathogenic *Escherichia coli*, more specifically, a composition containing a Myoviridae bacteriophage and a method of using the same.

Discussion of the Related Art

*Escherichia coli* is a Gram-negative, facultative anaerobic, rod-shaped, coliform bacterium of the genus *Escherichia*. It is serologically subdivided according to whether it contains a somatic (O), flagellar (H) or capsular (K) antigen, and these antigens are known to be associated with the pathogenicity of *Escherichia coli*. Pathogenic *Escherichia coli* refers to *Escherichia coli* that has acquired a small number of the virulence factors capable of being expressed in *Escherichia coli*, and, depending on the onset characteristics and the kind of toxin, there are five types of pathogenic *Escherichia coli*, namely enterohemorrhagic *Escherichia coli*, enterotoxigenic *Escherichia coli*, enteroinvasive *Escherichia coli*, enteropathogenic *Escherichia coli*, and enteroaggregative *Escherichia coli*.

Pathogenic *Escherichia coli* causes various diseases, such as food poisoning, acute pancreatitis, urinary tract infection, septicemia and cancer. Among pathogenic *Escherichia coli*-associated cancer, colorectal cancer is one of the most common cancers, accounting for approximately 10% of all cancer cases and approximately 8% of all cancer deaths. Also, colorectal cancer is very common globally and develops through accumulation of colonic epithelial cell mutations that promote transition of normal mucosa to adenocarcinoma. As one of major causes leading to colorectal cancer occurrence, colonic polyp refers to a condition in which the colonic mucosa grows abnormally and becomes a wart-shaped bump that protrudes into the intestine. It is often divided into neoplastic polyps that are likely to develop into cancer and non-neoplastic polyps that are unlikely to develop into cancers. Among various types of polyp, adenomatous polyps are more likely to develop cancer over time. Although diarrhea caused by pathogenic *Escherichia coli* is a notable disease, colonization of some pathogenic *Escherichia coli* is related to promotion of colorectal cancer development by promotion of the formation of adenomatous polyps.

Generally, vaccines and antibiotics are used for the prevention and treatment of infectious diseases of pathogenic *Escherichia coli*. Here, the effectiveness of antibiotics has been continuously decreasing due to the increase of antibiotic-resistant pathogenic *Escherichia coli*, and the development of effective methods other than currently prescribed antibiotics is required.

Recently, the use of bacteriophages as a countermeasure against bacterial infectious diseases has attracted considerable attention. Bacteriophages are very small microorganisms infecting bacteria, and are usually simply called “phages.” Once a bacteriophage infects a bacterial cell, the bacteriophage is proliferated inside the bacterial cell. After proliferation, the progeny of the bacteriophage destroys the bacterial cell wall and escapes from the host bacteria, suggesting that the bacteriophage has the ability to kill bacteria. The manner in which the bacteriophage infects bacteria is characterized by the very high specificity thereof, and thus the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria, but does not affect commensal bacteria in animals including human being. Conventional antibiotics, which have been widely used for bacterial treatment, incidentally influence many kinds of bacteria. This causes problems such as the disturbance of normal microflora. On the other hand, the use of bacteriophages does not disturb normal microflora, because the target bacterium is selectively killed. Hence, the bacteriophage may be utilized safely, which thus greatly lessens the probability of adverse actions in use compared to any other antibiotics.

Owing to the unique ability of bacteriophages to kill bacteria, bacteriophages have attracted attention as a potentially effective countermeasure against bacterial infections since their discovery, and there has been a lot of research related thereto.

Bacteriophages tend to be highly specific for bacteria. Because of this specificity, bacteriophages frequently exhibit an antibacterial effect only for certain strains of bacteria, even though the bacteria belong to the same species. In addition, the antibacterial strength of bacteriophages may depend on the type of target bacterial strain. Therefore, it is necessary to collect many kinds of bacteriophages that are useful in order to get effective control of specific bacteria. Hence, in order to develop the effective bacteriophage utilization method in response to pathogenic *Escherichia coli*, many kinds of bacteriophages that exhibit antibacterial action against pathogenic *Escherichia coli* must be acquired. Furthermore, the resulting bacteriophages need to be screened as to whether or not they are superior to others from the aspect of antibacterial strength and spectrum.

SUMMARY OF THE INVENTION

Accordingly, the present invention has been made keeping in mind the problems encountered in the related art and is intended to solve such problems.

In one embodiment, a composition for preventing or treating an infection or disease caused by a pathogenic *Escherichia coli* includes: a Myoviridae bacteriophage having an ability to lyse the pathogenic *Escherichia coli*, and a pharmaceutically acceptable carrier.

In another embodiment, the Myoviridae bacteriophage includes a sequence as set forth in SEQ ID NO: 1.

In another embodiment, the Myoviridae bacteriophage has a concentration of $1\times10^{1}$ pfu/ml to $1\times10^{30}$ pfu/ml or $1\times10^{1}$ pfu/g to $1\times10^{30}$ pfu/g.

In another embodiment, the Myoviridae bacteriophage has a concentration of $1\times10^{4}$ pfu/ml to $1\times10^{15}$ pfu/ml or $1\times10^{4}$ pfu/g to $1\times10^{15}$ pfu/g.

In another embodiment, the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, or mineral oil.

In another embodiment, the composition further includes one or more selected from the group consisting of a lubricant, a wetting agent, a sweetener, a flavor, an emulsifier, a suspending agent, and a preservative.

In another embodiment, the pathogenic *Escherichia coli* is enterohemorrhagic *Escherichia coli*, enterotoxigenic *Escherichia coli*, enteroinvasive *Escherichia coli*, enteropathogenic *Escherichia coli*, enteroaggregative *Escherichia coli*, or carcinogenic *Escherichia coli*.

In another embodiment, the infection or disease is food poisoning, gastroenteritis, diarrhea, urinary tract infections, neonatal meningitis, hemolytic-uremic syndrome, peritonitis, mastitis, septicemia, Gram-negative pneumonia, shigellosis, dysentery, or cancer.

In another embodiment, the composition is a solution, suspension, emulsion in oil, water-soluble medium, extract, powder, granule, tablet, or capsule.

In another embodiment, the composition further includes a second bacteriophage having an ability to lyse a pathogenic *Escherichia coli* or a non-*Escherichia coli* bacterial species.

In another embodiment, the Myoviridae bacteriophage has a latent period of 20-70 minutes and a burst size of 80-200 PFU/infected cell.

In another embodiment, the latent period is 35-40 minutes and the burst size of 110-120 PFU/infected cell.

In one embodiment, a method for preventing or treating an infection or disease caused by a pathogenic *Escherichia coli* includes administering to a subject a Myoviridae bacteriophage; and lysing the pathogenic *Escherichia coli* by the Myoviridae bacteriophage.

In another embodiment, the Myoviridae bacteriophage includes a sequence as set forth in SEQ ID NO: 1.

In another embodiment, the Myoviridae bacteriophage has a concentration of $1\times10^{1}$ pfu/ml to $1\times10^{30}$ pfu/ml or $1\times10^{1}$ pfu/g to $1\times10^{30}$ pfu/g.

In another embodiment, the Myoviridae bacteriophage has a concentration of $1\times10^{4}$ pfu/ml to $1\times10^{15}$ pfu/ml or $1\times10^{4}$ pfu/g to $1\times10^{15}$ pfu/g.

It is to be understood that both the foregoing general description and the following detailed description are exemplary and explanatory and are intended to provide further explanation of the invention as claimed

ADVANTAGEOUS EFFECTS OF INVENTION

The compositions and methods for inhibiting the proliferation of pathogenic *Escherichia coli*, of the present application have high specificity against pathogenic *Escherichia coli*, compared with conventional compositions and methods based on antibiotics. The compositions can be used for preventing or treating pathogenic *Escherichia coli* infections without affecting other useful commensal bacteria and have fewer side effects. In general, when antibiotics are used, commensal bacteria are also damaged, thus entailing various side effects owing to the use thereof. Meanwhile, each antibacterial property of the bacteriophages such as antibacterial strength and spectrum (host range) are different in the case of bacteriophages exhibiting antibacterial activity against the same bacterial species and bacteriophages are usually effective only on some bacterial strains within the same bacterial species. Thus, the compositions and methods of the present application provide different effects in its industrial applications.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
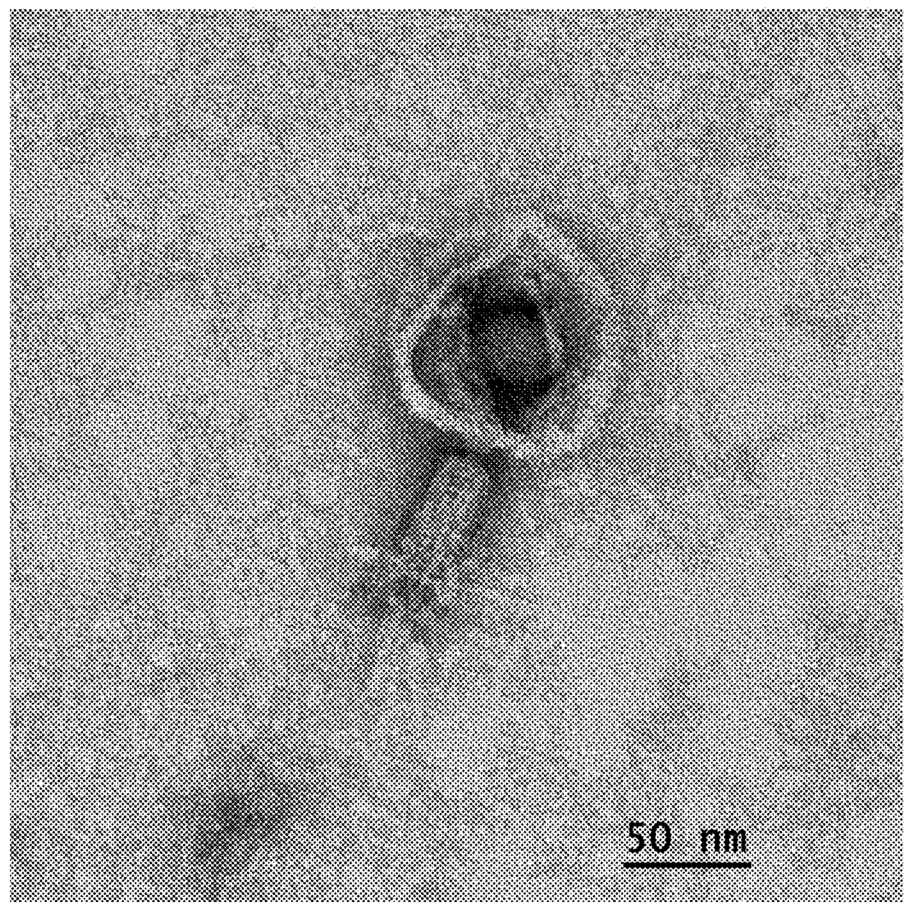
FIG. 1 is an electron micrograph showing the morphology of the bacteriophage Esc-COP-15.

Reference will now be made in detail to embodiments of the present invention, example of which is illustrated in the accompanying drawings.

In accordance with one aspect of the present invention, the present invention provides a Myoviridae bacteriophage, named as Esc-COP-15, which has the ability to specifically kill *Escherichia coli* and has a genome including a sequence as set forth in SEQ ID NO: 1. The present invention also provides a method for preventing and treating infections or diseases caused by pathogenic *Escherichia coli* using a composition including the same as an active ingredient.

The bacteriophage Esc-COP-15 was isolated by the present inventors and then deposited at Korea Collection for Type Cultures, Korea Research Institute of Bioscience and Biotechnology on Nov. 15, 2019 (Accession number: KCTC 14027BP).

The latent period and burst size of the bacteriophage Esc-COP-15 are 20-70 minutes and 80-200 PFU/infected cell, respectively, preferably 35-40 minutes and 110-120 PFU/infected cell, respectively, but are not limited thereto.

Also, the present invention provides a composition applicable for the prevention or treatment of infections or diseases caused by pathogenic *Escherichia coli*, which include the bacteriophage Esc-COP-15 as an active ingredient.

Because the bacteriophage Esc-COP-15 included in the composition of the present invention kills pathogenic *Escherichia coli* effectively, it is considered effective in the prevention of pathogenic *Escherichia coli* infections or treatment of diseases caused by pathogenic *Escherichia coli*. Therefore, the composition of the present invention is capable of being utilized for the prevention and treatment of diseases caused by pathogenic *Escherichia coli*.

The diseases caused by pathogenic *Escherichia coli* in the present invention include food poisoning, gastroenteritis, diarrhea, urinary tract infections, neonatal meningitis, hemolytic-uremic syndrome, peritonitis, mastitis, septicemia, Gram-negative pneumonia, shigellosis, dysentery and cancer, but are not limited thereto.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Esc-COP-15 is included as an active ingredient. The bacteriophage Esc-COP-15 is included at a concentration of $1\times10^{1}$ pfu/ml to $1\times10^{30}$ pfu/ml or $1\times10^{1}$ pfu/g to $1\times10^{30}$ pfu/g, and preferably at a concentration of $1\times10^{4}$ pfu/ml to $1\times10^{15}$ pfu/ml or $1\times10^{4}$ pfu/g to $1\times10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. Then, the formulation may be in the form of a solution, suspension, or emulsion in oil or a water-soluble medium, extract, powder, granule, tablet, or capsule. A dispersing agent or stabilizer may be additionally included.

In order to improve the effectiveness of above purpose, bacteriophages that have antibacterial activity against non-*Escherichia coli* bacterial species may be further included in the composition of the present invention. In addition, other kinds of bacteriophages that have antibacterial activity against *Escherichia coli* may be further included in the composition of the present invention. These bacteriophages may be additionally included so as to maximize antibacterial effects, because each antibacterial property of the bacteriophages such as antibacterial strength and spectrum (host range) are different in the case of bacteriophages exhibiting antibacterial activity against the same bacterial species.

In this description, the terms "prevention" and "prevent" indicate (i) to block pathogenic *Escherichia coli* infections; and (ii) to inhibit the progression of diseases caused by pathogenic *Escherichia coli* infections.

In this description, the terms "treatment" and "treat" indicate all actions that (i) suppress diseases caused by pathogenic *Escherichia coli*; and (ii) alleviate the pathological condition of the diseases caused by pathogenic *Escherichia coli*.

In this description, the term "pathogenic *Escherichia coli*" indicates enterohemorrhagic *Escherichia coli*, enterotoxigenic *Escherichia coli*, enteroinvasive *Escherichia coli*, enteropathogenic *Escherichia coli*, enteroaggregative *Escherichia coli* and carcinogenic *Escherichia coli*, but are not limited thereto.

In this description, the terms "diseases caused by pathogenic *Escherichia coli*" and "pathogenic *Escherichia coli* infections" indicate food poisoning, gastroenteritis, diarrhea, urinary tract infections, neonatal meningitis, hemolytic-uremic syndrome, peritonitis, mastitis, septicemia, Gram-negative pneumonia, shigellosis, dysentery and cancer, but are not limited thereto.

In this description, the term "Latent period" indicates the time taken by a bacteriophage particle to reproduce inside an infected host cell.

In this description, the term "Burst size" indicates the number of bacteriophages produced per infected bacterium.

In this description, the terms "isolate", "isolating", and "isolated" indicate actions which isolate bacteriophages from nature by applying diverse experimental techniques and which secure characteristics that can distinguish the target bacteriophage from others, and further include the action of proliferating the target bacteriophage using bioengineering techniques so that the target bacteriophage is industrially applicable.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing *Escherichia coli*

Samples were collected from environmental or clinical samples to isolate the bacteriophage capable of killing *Escherichia coli*. Here, the *Escherichia coli* strains used for the bacteriophage isolation had been previously isolated and identified as *Escherichia coli* by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Escherichia coli* at a ratio of 1/1000, followed by shaking culture at 37° C. for 3 to 4 hours. Upon completion of the culture, centrifugation was performed at 8,000 rpm for 20 minutes and a supernatant was recovered. The recovered supernatant was inoculated with *Escherichia coli* at a ratio of 1/1000, followed by shaking culture at 37° C. for 3 to 4 hours. When the sample contained the bacteriophage, the above procedure was repeated a total of 5 times in order to sufficiently increase the number (titer) of the bacteriophage. After repeating the procedure 5 times, the culture solution was subjected to centrifugation at 8,000 rpm for 20 minutes. After the centrifugation, the recovered supernatant was filtered using a 0.45 μm filter. The obtained filtrate was used in a typical spot assay for examining whether or not a bacteriophage capable of killing *Escherichia coli* was included therein.

The spot assay was performed as follows: TSB culture medium was inoculated with *Escherichia coli* at a ratio of 1/1000, followed by shaking culture at 37° C. overnight. 2 ml ($OD_{600}$ of 1.5) of the culture solution of *Escherichia coli* prepared above was spread on TSA (casein digest, 15 g/L; soybean digest, 5 g/L; NaCl, 5 g/L; agar, 15 g/L) plate. The plate was left on a clean bench for about 30 minutes to dry the spread solution. After drying, 10 μl of the prepared filtrate was spotted onto the plate culture medium on which *Escherichia coli* was spread and then left to dry for about 30 minutes. After drying, the plate culture medium that was subjected to spotting was incubated at 37° C. for one day, and then examined for the formation of clear zones at the positions where the filtrate was dropped. In the case of the filtrate generated a clear zone, it is judged that the bacteriophage capable of killing *Escherichia coli* is included therein. Through the above examination, the filtrate containing the bacteriophage having the ability to kill *Escherichia coli* could be obtained.

The pure bacteriophage was isolated from the filtrate confirmed above to have the bacteriophage capable of killing *Escherichia coli*. A conventional plaque assay was used to isolate the pure bacteriophage. In detail, a plaque formed in the course of the plaque assay was recovered using a sterilized tip, which was then added to the culture solution of *Escherichia coli*, followed by culturing at 37° C. for 4 to 5 hours. After the culturing, centrifugation was performed at 8,000 rpm for 20 minutes to obtain a supernatant. The *Escherichia coli* culture solution was added to the obtained supernatant at a volume ratio of 1/50, followed by culturing at 37° C. for 4 to 5 hours. In order to increase the number of bacteriophages, the above procedure was repeated at least 5 times. Then, centrifugation was performed at 8,000 rpm for 20 minutes in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, a solution containing the pure bacteriophage was obtained. The procedure for isolating the pure bacteriophage was generally repeated until the generated plaques became similar to each other in size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Myoviridae bacteriophage.

The solution containing the pure bacteriophage confirmed above was subjected to the following purification process. The *Escherichia coli* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times in order to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM MgSO4, 0.1% gelatin, pH 8.0). The resulting material was referred to as a bacteriophage suspension or bacteriophage solution.

As a result, the pure bacteriophage purified above was collected, was named the bacteriophage Esc-COP-15, and then deposited at Korea Collection for Type Culture, Korea Research Institute of Bioscience and Biotechnology on Nov. 15, 2019 (Accession number: KCTC 14027BP).

Example 2: Separation and Sequence Analysis of Genome of Bacteriophage Esc-COP-15

The genome of the bacteriophage Esc-COP-15 was separated as follows. The genome was separated from the bacteriophage suspension obtained using the same method as in Example 1. First, in order to remove DNA and RNA of *Escherichia coli* included in the suspension, 200 U of each of DNase I and RNase A was added to 10 ml of the bacteriophage suspension and then left at 37° C. for 30 minutes. After being left for 30 minutes, in order to stop the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After reaction for 1 hour, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes in order to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the genome of the bacteriophage Esc-COP-15.

Information on the sequence of the genome of the bacteriophage Esc-COP-15 obtained above was secured by performing next-generation sequencing analysis using Illumina Mi-Seq equipment from the National Instrumentation Center for Environmental Management, Seoul National University. The finally analyzed genome of the bacteriophage Esc-COP-15 had a size of 152,531 bp, and the sequence of whole genome was expressed by SEQ ID NO: 1.

The homology (similarity) of the bacteriophage Esc-COP-15 genomic sequence obtained above with previously reported bacteriophage genomic sequences was investigated using BLAST investigation, the genomic sequence of the bacteriophage Esc-COP-15 was found to have a relatively high homology with the sequence of the *Escherichia* bacteriophage ESCO13 (Genbank Accession No. KX552041.2) (identity: 79%). However, the number of open reading frames (ORFs) on the bacteriophage Esc-COP-15 genome is 292, whereas *Escherichia* bacteriophage ESCO13 has 282 open reading frames, unlike the bacteriophage Esc-COP-9.

Based upon this result, it is concluded that the bacteriophage Esc-COP-15 must be a novel bacteriophage different from conventionally reported bacteriophages. Further, since the antibacterial strength and spectrum of bacteriophages typically depend on the type of bacteriophage, it is considered that the bacteriophage Esc-COP-15 can provide antibacterial activity different from that of any other bacteriophages reported previously.

Example 3: Analysis of the Major Structural Proteins of Bacteriophage Esc-COP-15

Figure 2:
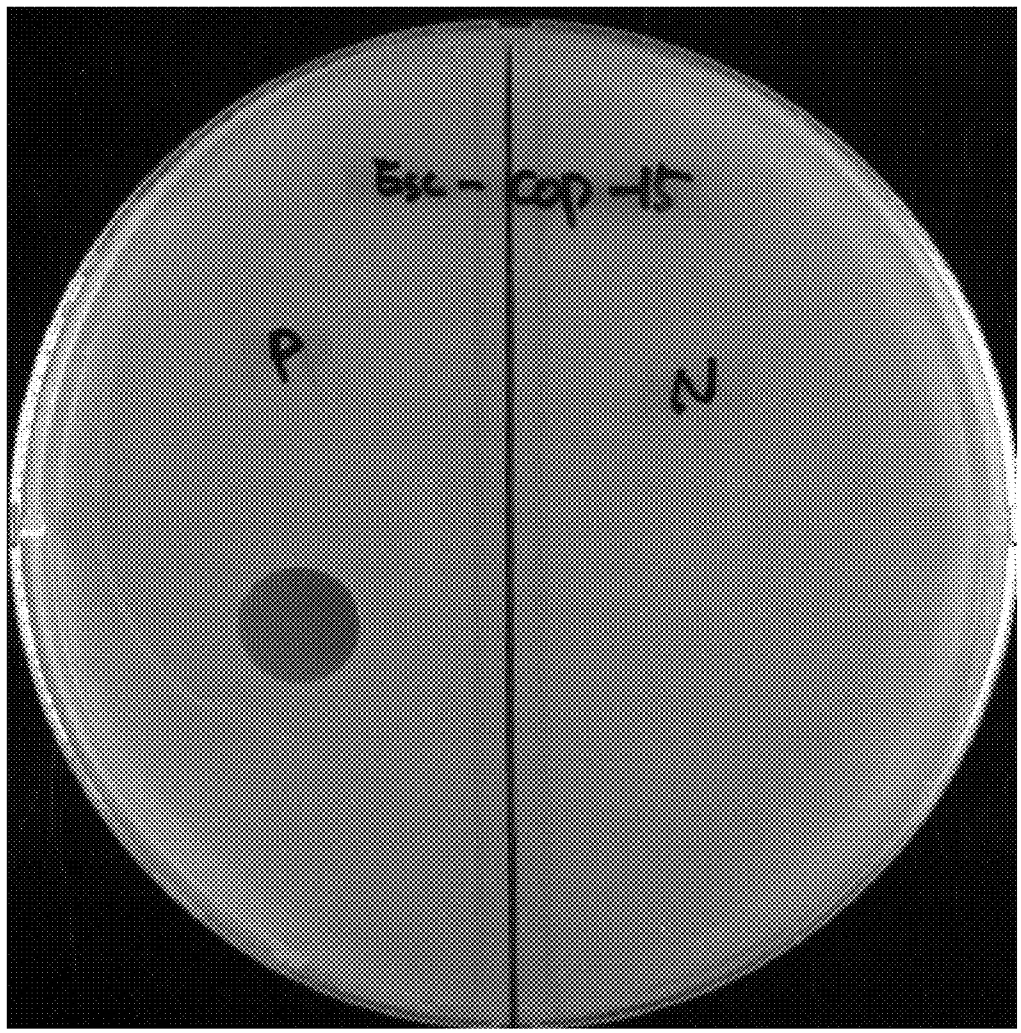
FIG. 2 is a result of the analysis for major structural proteins of bacteriophage Esc-COP-15.

One-dimensional electrophoresis was performed to analyze the major structural proteins of the bacteriophage Esc-COP-15. To obtain the proteins consisting the outer wall of the bacteriophage Esc-COP-15, 200 μl of the bacteriophage suspension prepared in Example 1 was mixed with 800 μl of acetone, which was vortexed vigorously. The mixture stood at −20° C. for 10 minutes. Centrifugation was performed at 13,000 rpm at 4° C. for 20 minutes to eliminate supernatant, followed by air drying. The precipitate was resuspended in 50 μl of electrophoresis sample buffer (5×), which was then boiled for 5 minutes. The prepared sample was analyzed by one-dimensional electrophoresis. As a result, as shown in FIG. 2, the major structural proteins in the sizes of approximately 13 kDa, 35 kDa, 100 kDa, and 157 kDa were confirmed.

Example 4: Investigation of Ability of Bacteriophage Esc-COP-15 to Kill Pathogenic *Escherichia coli*

Figure 3:
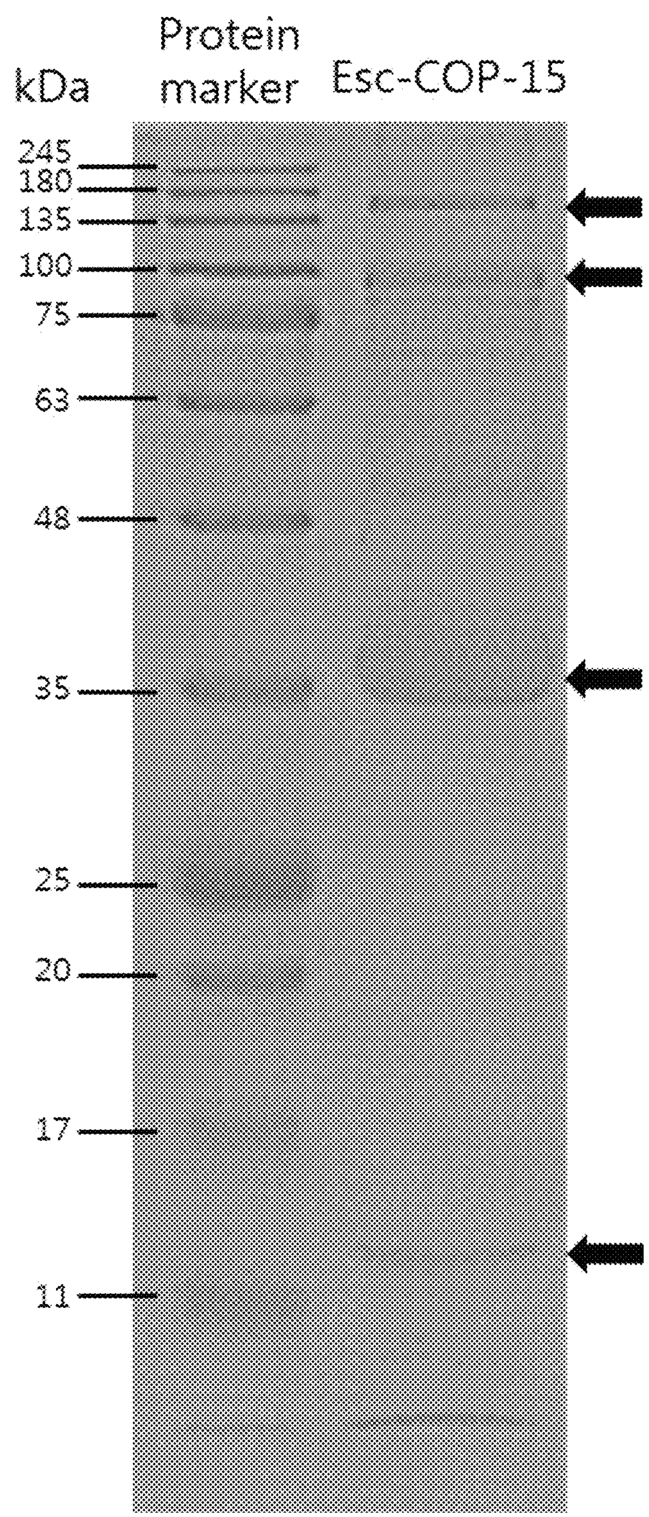
FIG. 3 is a photograph showing the results of an experiment on the ability of the bacteriophage Esc-COP-15 to kill *Escherichia coli*. The clear zone is a plaque formed by lysis of the target bacteria.

The ability of bacteriophage Esc-COP-15 to kill pathogenic *Escherichia coli* was investigated. In order to investigate the killing ability, the formation of clear zones was observed using the spot assay in the same manner as described in Example 1. A total of 6 strains that had been identified as pks positive *Escherichia coli* strains that are positive carriers of the pks genomic island were used as pathogenic *Escherichia coli* for the investigation of killing ability. The bacteriophage Esc-COP-15 had the ability to lyse and kill a total of 5 strains among 6 strains of pathogenic *Escherichia coli* as the experimental target. The experimental result thereof is presented in Table 1 and the representative result is shown in FIG. 3.

TABLE 1

Test of antibacterial activity of bacteriophage Esc-COP-15

| Tested Escherichia coli strain | Test result |
|---|---|
| *Escherichia coli* CCARM 1G930 | + |
| *Escherichia coli* CCARM 1G931 | + |
| *Escherichia coli* CCARM 1G933 | + |
| *Escherichia coli* CCARM 1G934 | + |
| *Escherichia coli* CCARM 1G938 | + |
| *Escherichia coli* CCARM 1G939 | − |

* +: clear lytic activity, no lytic activity;
CCARM: Culture Collection of Antimicrobial Resistant Microbes (Seoul, Korea)

Meanwhile, the ability of the bacteriophage Esc-COP-15 to kill *Bordetella bronchiseptica, Enterococcus faecalis, Enterococcus faecium, Streptococcus mitis, Streptococcus uberis* and *Pseudomonas aeruginosa* was also investigated in a separate experiment. As a result, the bacteriophage Esc-COP-15 did not have the ability to kill these bacteria.

Therefore, it is confirmed that the bacteriophage Esc-COP-15 has strong ability to kill pathogenic *Escherichia coli* and a broad antibacterial spectrum against pathogenic *Escherichia coli*, suggesting that the bacteriophage Esc-COP-15 can be used as an active ingredient of the composition for preventing and treating pathogenic *Escherichia coli* infections.

Example 5: Growth Characteristic of Bacteriophage Esc-COP-15

Figure 4:
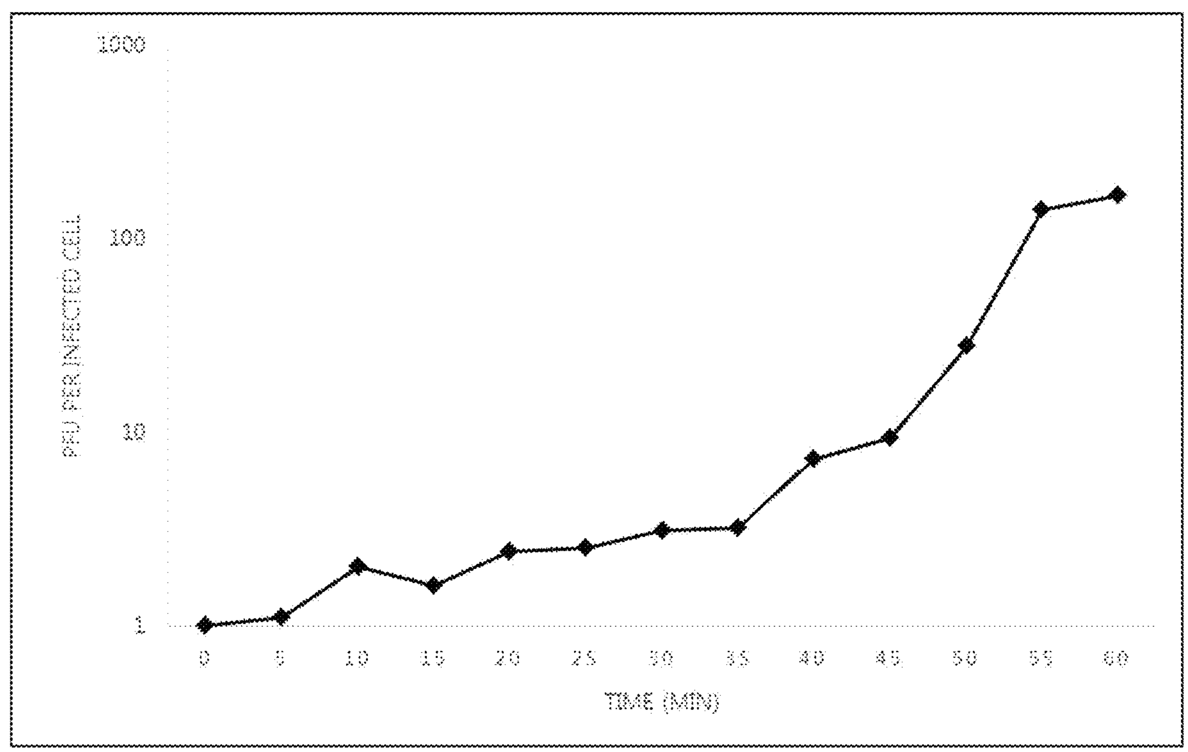
FIG. 4 is the one-step growth curve of bacteriophage Esc-COP-15.

The growth characteristics of bacteriophage Esc-COP-15 was analyzed by one-step growth curve analysis. One-step growth curve analysis of bacteriophage Esc-COP-15 was performed as follows: 50 ml of TSB (Tryptic soy broth, Difco) culture medium was inoculated with *Escherichia coli* at a ratio of 1/1000 and followed by shaking culture until exponential phase ($OD_{600}$=0.3~0.4). Upon completion of the culture, centrifugation was performed at 8,000 rpm for 5 min and a bacterial cell pellet was recovered. The recovered pellet was suspended in 50 ml of TSB. The resulting material may be referred to as a bacterial suspension. The bacteriophage Esc-COP-15 was mixed with the bacterial suspension at a multiplicity of infection (MOI) of 0.1 and incubated at room temperature for 10 min, and then centrifuged at 12,000 rpm for 30 seconds. After supernatants were removed, the pellets containing bacteriophage-infected bacterial cells were suspended in 50 ml of TSB and incubated at 37° C. with shaking. Aliquots were taken at 5 min intervals for 60 min, and the titers in the aliquots were immediately determined by the conventional plaque assay (FIG. 4).

The latent period of bacteriophage Esc-COP-15 was estimated to be approximately 35±5 min with average burst size of about 110±10 pfu/infected cell.

Example 6: Experimental Example Regarding Prevention of Pathogenic *Escherichia coli* Infection Using Bacteriophage Esc-COP-15

100 μl of a bacteriophage Esc-COP-15 suspension ($1\times10^8$ pfu/ml) was added to a tube containing 9 ml of a TSB culture medium. To another tube containing 9 ml of a TSB culture medium, only the same amount of TSB culture medium was further added. A pathogenic *Escherichia coli* (pks positive strain CCARM 1G930) culture solution was then added to each tube so that absorbance reached about 0.5 at 600 nm. After pathogenic *Escherichia coli* was added, the tubes were transferred to an incubator at 37° C., followed by shaking culture, during which the growth of pathogenic *Escherichia coli* was observed. As presented in Table 2, it was observed that the growth of pathogenic *Escherichia coli* was inhibited in the tube to which the bacteriophage Esc-COP-15 suspension was added, while the growth of pathogenic *Escherichia coli* was not inhibited in the tube to which the bacteriophage suspension was not added.

TABLE 2

Test for bacterial growth inhibition of bacteriophage Esc-COP-15

| | $OD_{600}$ | | |
|---|---|---|---|
| Classification | 0 minutes after initiation of cultivation | 30 minutes after initiation of cultivation | 60 minutes after initiation of cultivation |
| Bacteriophage suspension was not added | 0.6 | 0.8 | 1.4 |
| Bacteriophage suspension was added | 0.6 | 0.4 | 0.1 |

The above results indicate that the bacteriophage Esc-COP-15 of the present invention not only inhibits the growth of pathogenic *Escherichia coli* but also has the ability to kill pathogenic *Escherichia coli*. Therefore, it is concluded that the bacteriophage Esc-COP-15 can be used as an active ingredient of the composition for preventing a pathogenic *Escherichia coli* infection.

Example 7: Preventive Effect of Bacteriophage Esc-COP-15 on the Infections of *Escherichia coli* in Animal Model Preventive effect of the bacteriophage Esc-COP-15 on weaning pigs affected by *Escherichia coli* was investigated. 4 weaning pigs at 25 days of age were grouped together; total 2 groups of pigs were raised in each pig pen (1.1 m×1.0 m). Heating system was furnished and the surrounding environment was controlled. The temperature and the humidity of the pig pen were controlled consistently and the floor was cleaned every day. From the $1^{st}$ day of the experiment, pigs of the experimental group (adding the bacteriophage) were fed with feeds adding the bacteriophage Esc-COP-15 at $1\times10^8$ pfu/g according to the conventional feed supply procedure, while pigs of the control group (without adding the bacteriophage) were fed with the same feed without adding the bacteriophage Esc-COP-15 according to the conventional procedure. From the $7^{th}$ day of the experiment, the feeds of both groups were contaminated with $1\times10^8$ cfu/g of pathogenic *Escherichia coli* for 2 days and thereafter provided twice a day respectively for the experimental and the control groups so as to bring about the infections of pathogenic *Escherichia coli*. The administered pathogenic *Escherichia coli* suspension was prepared as follows: Pathogenic *Escherichia coli* (strain CCARM 1G931) was cultured at 37° C. for 18 hours using a TSB culture medium, after which the bacteria were isolated and adjusted to $10^9$ CFU/ml using physiological saline (pH 7.2). From the next day after providing contaminated feeds for 2 days (the $9^{th}$ day of the experiment), pigs of the experimental group (adding the bacteriophage) were fed again with the feeds adding the bacteriophage Esc-COP-15 at $1\times10^8$ pfu/g without contaminating pathogenic *Escherichia coli* according to the conventional feed supply procedure as before, while pigs of the control group (without adding the bacteriophage) were fed with the same feed without adding the bacteriophage according to the conventional procedure. From the $9^{th}$ day of the experiment, diarrhea was examined in all test animals on a daily basis. The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3). The results are shown in Table 3.

TABLE 3

Fecal Consistency score

| | Fecal Consistency score | | | | | |
|---|---|---|---|---|---|---|
| | D9 | D10 | D11 | D12 | D13 | D14 |
| Control group (bacteriophage suspension was not administered) | 2.0 | 2.0 | 1.5 | 1.25 | 1.0 | 0.75 |
| Experimental group (bacteriophage suspension was administered) | 0.75 | 0.5 | 0.25 | 0 | 0 | 0 |

From the above results, it is confirmed that the bacteriophage Esc-COP-15 of the present invention could be very effective to suppress the infections of pathogenic *Escherichia coli.*

Example 8: Example of Treatment of Infectious Diseases of Pathogenic *Escherichia coli* Using Bacteriophage Esc-COP-15

The therapeutic effect of the bacteriophage Esc-COP-15 on diseases caused by pathogenic *Escherichia coli* was evaluated as follows: 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of a pathogenic *Escherichia coli* suspension was administered to all mice through intraperitoneal injection. The administered pathogenic *Escherichia coli* suspension was prepared as follows: Pathogenic *Escherichia coli* (strain CCARM 1G931) was cultured at 37° C. for 18 hours using a TSB culture medium, after which the bacteria were isolated and adjusted to $10^9$ CFU/ml using physiological saline (pH 7.2). At 2 hr after administration of pathogenic *Escherichia coli,* $10^9$ pfu of bacteriophage Esc-COP-15 was administered through intraperitoneal injection to mice in the experimental group (administered with the bacteriophage suspension). 0.1 ml of saline was administered through intraperitoneal injection to mice in the control group (not administered with the bacteriophage suspension). Both the control and experimental groups were equally fed with feed and drinking water. Whether or not the mice survived was observed daily starting from the administration of pathogenic *Escherichia coli* until the end of the test. The results are shown in Table 4 below.

TABLE 4

Survival rate

| | Survival rate (%) | | | | | |
|---|---|---|---|---|---|---|
| | D2 | D3 | D4 | D5 | D6 | D7 |
| Control group (not administered with bacteriophage suspension) | 100 | 70 | 40 | 10 | 10 | 10 |
| Experimental group (administered with bacteriophage suspension through intraperitoneal injection) | 100 | 90 | 80 | 80 | 80 | 80 |

As is apparent from the above results, it can be concluded that the bacteriophage Esc-COP-15 of the present invention is very effective in the treatment of diseases caused by pathogenic *Escherichia coli.*

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Accession Number
Name of Depositary Authority: KCTC
Accession number: KCTC 14027BP
Accession date: Nov. 15, 2019

What is claimed is:

1. A composition for preventing or treating an infection or disease caused by a pathogenic *Escherichia coli* comprising:

a Myoviridae bacteriophage Esc-COP-15 having an ability to lyse the pathogenic *Escherichia coli* and a genome represented by a sequence as set forth in SEQ ID NO: 1; and a pharmaceutically acceptable carrier, wherein the Myoviridae bacteriophage Esc-COP-15 has a latent period of 20-70 minutes and a burst size of 80-200 plaque-forming units (PFU)/infected cell and is deposited in the Korean Collection for Type Cultures (KCTC) under accession number KCTC 14027BP; and wherein the Myoviridae bacteriophage Esc-COP-15 has a concentration of $1\times10^4$ pfu/ml to $1\times10^{15}$ pfu/ml or $1\times10^4$ pfu/g to $1\times10^{15}$ pfu/g.

2. The composition of claim 1, wherein the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, or mineral oil.

3. The composition of claim 1 further comprising:

one or more selected from the group consisting of a lubricant, a wetting agent, a sweetener, a flavor, an emulsifier, a suspending agent, and a preservative.

4. The composition of claim 1, wherein the pathogenic *Escherichia coli* is enterohemorrhagic *Escherichia coli*, enterotoxigenic *Escherichia coli*, enteroinvasive *Escherichia coli*, enteropathogenic *Escherichia coli*, enteroaggregative *Escherichia coli*, or carcinogenic *Escherichia coli*.

5. The composition of claim 1, wherein the infection or disease is food poisoning, gastroenteritis, diarrhea, urinary tract infections, neonatal meningitis, hemolytic-uremic syndrome, peritonitis, mastitis, septicemia, Gram-negative pneumonia, shigellosis, dysentery, or cancer.

6. The composition of claim 1, wherein the composition is a solution, suspension, emulsion in oil, water-soluble medium, extract, powder, granule, tablet, or capsule.

7. The composition of claim 1 further comprising:

a second bacteriophage having an ability to lyse a pathogenic *Escherichia coli* or a non-*Escherichia coli* bacterial species.

* * * * *